US009925219B2

(12) United States Patent
Kauper et al.

(10) Patent No.: US 9,925,219 B2
(45) Date of Patent: Mar. 27, 2018

(54) ENCAPSULATED CELL THERAPY CARTRIDGE

(71) Applicant: Neurotech USA, Inc., Cumberland, RI (US)

(72) Inventors: Konrad A. Kauper, Sutton, MA (US); John Fraser Mills, Wakefield, RI (US); Megan Billings, West Warwick, RI (US); Michael R. Rivera, Johnston, RI (US); Alline Monteiro Alcantara Lelis, Fall River, MA (US)

(73) Assignee: Neurotech USA, Inc., Cumberland, RI (US)

( * ) Notice: Subject to any disclaimer, the term of this patent is extended or adjusted under 35 U.S.C. 154(b) by 31 days.

(21) Appl. No.: 14/483,118

(22) Filed: Sep. 10, 2014

(65) Prior Publication Data

US 2015/0073381 A1    Mar. 12, 2015

Related U.S. Application Data

(60) Provisional application No. 61/876,638, filed on Sep. 11, 2013.

(51) Int. Cl.
| | |
|---|---|
| *A61K 35/12* | (2015.01) |
| *A61M 37/00* | (2006.01) |
| *A61K 9/00* | (2006.01) |
| *A61K 38/17* | (2006.01) |
| *C12N 5/00* | (2006.01) |
| *A61F 9/00* | (2006.01) |

(52) U.S. Cl.
CPC ............... *A61K 35/12* (2013.01); *A61F 9/00* (2013.01); *A61K 9/0051* (2013.01); *A61K 38/179* (2013.01); *C12N 5/0012* (2013.01); *C12N 2510/02* (2013.01)

(58) Field of Classification Search
CPC ......... A61F 9/00; A61K 35/12; A61K 38/179; A61K 9/0051; C12N 2510/02; C12N 5/0012
USPC ...................... 435/174, 70.1, 325; 604/93.01
See application file for complete search history.

(56) References Cited

U.S. PATENT DOCUMENTS

| | | | |
|---|---|---|---|
| 4,892,538 A | 1/1990 | Aebischer et al. | |
| 4,968,733 A | 11/1990 | Muller et al. | |
| 4,976,859 A | 12/1990 | Wechs | |
| 5,156,844 A | 10/1992 | Aebischer et al. | |
| 5,158,881 A | 10/1992 | Aebischer et al. | |
| 5,283,138 A | 2/1994 | Ferrando | |
| 5,284,761 A | 2/1994 | Aebischer et al. | |
| 5,550,050 A | 8/1996 | Holland et al. | |
| 5,639,275 A | 6/1997 | Baetge et al. | |
| 5,653,975 A | 6/1997 | Baetge et al. | |
| 5,653,688 A | 8/1997 | Mills et al. | |
| 5,713,887 A | 2/1998 | Mills et al. | |
| 5,738,673 A | 4/1998 | Mills et al. | |
| 5,904,144 A | 5/1999 | Hammang et al. | |
| 5,932,460 A | 8/1999 | Mills et al. | |
| 6,123,700 A | 9/2000 | Mills et al. | |
| 6,361,771 B1 | 3/2002 | Tao et al. | |
| 6,653,687 B1 | 11/2003 | Yamazaki | |
| 2007/0154524 A1 | 7/2007 | Kauper et al. | |
| 2011/0111008 A1* | 5/2011 | Tao ...................... | A61K 9/0051 424/428 |
| 2012/0141573 A1 | 6/2012 | Ling et al. | |

FOREIGN PATENT DOCUMENTS

| | | |
|---|---|---|
| WO | WO 1996/002646 A2 | 2/1996 |
| WO | WO 2012/075184 A2 | 6/2012 |
| WO | W2013/181424 A1 * | 12/2013 |
| WO | WO 2013/181424 A1 | 12/2013 |

OTHER PUBLICATIONS

Aebischer et al., Transplantation in humans of encapsulated xenogeneic cells without immunosuppression, *Transplantation*, 58: 1275-1277 (1994).
Baetge et al., Complete nucleotide and deduced amino acid sequence of bovine phenylethanolamine N-methyltransferase. Partial amino acid homology with rat tyrosine hydroxylase, *Proc. Natl. Acad. Sci. USA*, 83: 5454-5458 (1986).
Dunn et al., ARPE-19, A Human Retinal Pigment Epithelial Cell Line with Differentiated Properties, *Exp. Eye Res.*, 62: 155-169 (1996).
Dunn et al., Use of the ARPE-19 Cell Line as a Model of RPE Polarity: Basolateral Secretion of FGF5, *Invest. Ophthalmol. Vis. Sci.*, 39: 2744-2749 (1998).
Finnemann et al., Phagocytosis of rod outer segments by retinal pigment epithelial cells requires $\alpha v \beta 5$ integrin for binding but not for internalization, *Proc. Natl. Acad. Sci. USA*, 94: 12932-12937 (1997).
Handa et al., The Advanced Glycation Endproduct Pentosidine Induces the Expression of PDGF-B in Human Retinal Pigment Epithelial Cells, *Exp. Eye. Res.*, 66: 411-419 (1998).
Holtkamp et al., Polarized secretion of IL-6 and IL-8 by human retinal pigment epithelial cells. *Clin. Exp. Immunol.*, 112: 34-43 (1997).
Maidji et al., Accessory Human Cytomegalovirus Glycoprotein US9 in the Unique Short Component of the Viral Genome Promotes Cell-to-Cell Transmission of Virus in Polarized Epithelial Cells, *J. Virol.*, 70: 8402-8410 (1996).
Southern, Mammalian Cell Transformation with SV40 Hybrid Plasmid Vectors, In Vitro, 18: 315 (1981).

(Continued)

*Primary Examiner* — Janet L Epps-Smith

(74) *Attorney, Agent, or Firm* — Cooley LLP; Ivor R. Elrifi; Christina K. Stock

(57) ABSTRACT

The invention provides multi-chamber encapsulated cell therapy cartridge devices that are capable of delivering biologically active molecules as well as methods of using these devices.

48 Claims, 25 Drawing Sheets

(56) References Cited

OTHER PUBLICATIONS

Southern and Berg, Transformation of Mammalian Cells to Antibiotic Resistance with a Bacterial Gene Under Control of the SV 40 Early Region Promoter, *J. Mol. Appl. Genet.*, 1: 327-341 (1982).
International Search Report issued in International Application No. PCT/US2014/055028 dated Jan. 8, 2015.

* cited by examiner

SEQUENCE LISTING

```
<160> NUMBER OF SEQ ID NOS: 32

<210> SEQ ID NO 1
<211> LENGTH: 1401
<212> TYPE: DNA
<213> ORGANISM: Artificial Sequence
<220> FEATURE:
<223> OTHER INFORMATION: 834 molecule nucleic acid sequence

<400> SEQUENCE: 1
atggtcagct actgggacac cggggtcctg ctgtgcgcgc tgctcagctg tctgcttctc    60
acaggatcta gttcaggttc gcgaagtgat acaggtagac ctttcgtaga gatgtacagt   120
gaaatccccg aaattataca catgactgaa ggaagggagc tcgtcattcc ctgccgggtt   180
acgtcaccta acatcactgt tactttaaaa aagtttccac ttgacacttt gatccctgat   240
ggaaaacgca taatctggga cagtagaaag ggcttcatca tatcaaatgc aacgtacaaa   300
gaaatagggc ttctgacctg tgaagcaaca gtcaatgggc atttgtataa gacaaactat   360
ctcacacatc gacaaaccaa tacaatcatc gatgtggttc tgagtccgtc tcatggaatt   420
gaactatctg ttggagaaaa gcttgtctta aattgtacag caagaactga actaaatgtg   480
gggattgact tcaactggga ataccttcct tcgaagcatc agcataagaa acttgtaaac   540
cgagacctaa aaacccagtc tgggagtgag atgaagaaat ttttgagcac cttaactata   600
gatggtgtaa cccggagtga ccaaggattg tacacctgtg cagcatccag tgggctgatg   660
accaagaaga acagcacatt tgtcagggtc catgaaaaag aattcgagcc caaatcttgt   720
gacaaaactc acacatgccc accgtgccca gcacctgaac tcctgggggg accgtcagtc   780
ttcctcttcc ccccaaaacc caaggacacc ctcatgatct cccggacccc tgaggtcaca   840
tgcgtggtgg tggacgtgag ccacgaagac cctgaggtca agttcaactg gtacgtggac   900
ggcgtggagg tgcataatgc caagacaaag ccgcgggagg agcagtacaa cagcacgtac   960
cgtgtggtca gcgtcctcac cgtcctgcac caggactggc tgaatggcaa ggagtacaag  1020
tgcaaggtct ccaacaaagc cctcccagcc cccatcgaga aaccatctc caaagccaaa  1080 gggcagcccc gagaaccaca ggtgtacacc ctgcccccat cccgggatga gctgaccaag  1140
aaccaggtca gcctgacctg cctggtcaaa ggcttctatc ccagcgacat cgccgtggag  1200
tgggagagca atgggcagcc ggagaacaac tacaagacca cgcctcccgt gctggactcc  1260
gacggctcct tcttcctcta cagcaagctc accgtggaca agagcaggtg gcagcagggg  1320
aacgtcttct catgctccgt gatgcatgag gctctgcaca accactacac gcagaagagc  1380
ctctccctgt ctccgggtaa a                                              1401
```

<210> SEQ ID NO 2
<211> LENGTH: 467
<212> TYPE: PRT
<213> ORGANISM: Artificial Sequence
<220> FEATURE:
<223> OTHER INFORMATION: 834 molecule amino acid sequence

<400> SEQUENCE: 2

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Arg Ser Asp Thr Gly
                20                  25                  30

Arg Pro Phe Val Glu Met Tyr Ser Glu Ile Pro Glu Ile Ile His Met
            35                  40                  45

Thr Glu Gly Arg Glu Leu Val Ile Pro Cys Arg Val Thr Ser Pro Asn
        50                  55                  60

Ile Thr Val Thr Leu Lys Lys Phe Pro Leu Asp Thr Leu Ile Pro Asp
65                  70                  75                  80

Gly Lys Arg Ile Ile Trp Asp Ser Arg Lys Gly Phe Ile Ile Ser Asn
                85                  90                  95

Ala Thr Tyr Lys Glu Ile Gly Leu Leu Thr Cys Glu Ala Thr Val Asn
            100                 105                 110

Gly His Leu Tyr Lys Thr Asn Tyr Leu Thr His Arg Gln Thr Asn Thr
        115                 120                 125

Ile Ile Asp Val Val Leu Ser Pro Ser His Gly Ile Glu Leu Ser Val
130                 135                 140

Gly Glu Lys Leu Val Leu Asn Cys Thr Ala Arg Thr Glu Leu Asn Val
145                 150                 155                 160

Gly Ile Asp Phe Asn Trp Glu Tyr Pro Ser Ser Lys His Gln His Lys
                165                 170                 175

Lys Leu Val Asn Arg Asp Leu Lys Thr Gln Ser Gly Ser Glu Met Lys
            180                 185                 190

Lys Phe Leu Ser Thr Leu Thr Ile Asp Gly Val Thr Arg Ser Asp Gln
        195                 200                 205

Gly Leu Tyr Thr Cys Ala Ala Ser Ser Gly Leu Met Thr Lys Lys Asn
    210                 215                 220

Ser Thr Phe Val Arg Val His Glu Lys Glu Phe Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365
```

| | | | | | | | | | | | |
|---|---|---|---|---|---|---|---|---|---|---|---|
|Tyr|Thr|Leu|Pro|Pro|Ser|Arg|Asp|Glu|Leu|Thr|Lys|Asn|Gln|Val|Ser|
| |370| | | |375| | | |380| | | | | | |

Leu Thr Cys Leu Val Lys Gly Phe Tyr Pro Ser Asp Ile Ala Val Glu
385             390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
    450                 455                 460

Pro Gly Lys
465

<210> SEQ ID NO 3
<211> LENGTH: 1707
<212> TYPE: DNA
<213> ORGANISM: Artificial Sequence
<220> FEATURE:
<223> OTHER INFORMATION: 838 molecule nucleic acid sequence

<400> SEQUENCE: 3

```
atggagagca aggtgctgct ggccgtcgcc ctgtggctct gcgtggagac ccgggccgcc    60
tctgtgggtt tgcctagtgt ttctcttgat ctgcccaggc tcagcataca aaagacata   120
cttacaatta aggctaatac aactcttcaa attacttgca ggggacagag ggacttggac   180
tggctttggc ccaataatca gagtggcagt gagcaaaggg tggaggtgac tgagtgcagc   240
gatggcctct tctgtaagac actcacaatt ccaaaagtga tcggaaatga cactggagcc   300
tacaagtgct tctaccggga aactgacttg gcctcggtca tttatgtcta tgttcaagat   360
tacagatctc catttattgc ttctgttagt gaccaacatg gagtcgtgta cattactgag   420
aacaaaaaca aaactgtggt gattccatgt ctcgggtcca tttcaaatct caacgtgtca   480
ctttgtgcaa gatacccaga aaagagattt gttcctgatg gtaacagaat ttcctgggac   540
agcaagaagg gctttactat tcccagctac atgatcagct atgctggcat ggtcttctgt   600
gaagcaaaaa ttaatgatga agttaccag tctattatgt acatagttgt cgttgtaggg   660
tataggattt atgatgtggt tctgagtccg tctcatggaa ttgaactatc tgttggagaa   720
aagcttgtct taaattgtac agcaagaact gaactaaatg tggggattga cttcaactgg   780
gaataccctt cttcgaagca tcagcataag aaacttgtaa accgagacct aaaaacccag   840
tctgggagtg agatgaagaa attttttgagc accttaacta tagatggtgt aacccggagt   900
gaccaaggat tgtacacctg tgcagcatcc agtgggctga tgaccaagaa gaacagcaca   960
tttgtcaggg tccatgaaaa accttttgtt gcttttggaa gtggcgaatt cgagcccaaa  1020
tcttgtgaca aaactcacac atgcccaccg tgcccagcac ctgaactcct ggggggaccg  1080
tcagtcttcc tcttcccccc aaaacccaag gacaccctca tgatctcccg gacccctgag  1140
gtcacatgcg tggtggtgga cgtgagccac gaagaccctg aggtcaagtt caactggtac  1200
gtggacggcg tggaggtgca taatgccaag acaaagccgc gggaggagca gtacaacagc  1260
acgtaccgtg tggtcagcgt cctcaccgtc ctgcaccagg actggctgaa tggcaaggag  1320
tacaagtgca aggtctccaa caaagccctc ccagccccca tcgagaaaac catctccaaa  1380
gccaaagggc agccccgaga accacaggtg tacaccctgc ccccatcccg ggatgagctg  1440
```

-continued

```
accaagaacc aggtcagcct gacctgcctg gtcaaaggct tctatcccag cgacatcgcc      1500
gtggagtggg agagcaatgg gcagccggag aacaactaca agaccacgcc tcccgtgctg      1560
gactccgacg gctccttctt cctctacagc aagctcaccg tggacaagag caggtggcag      1620
caggggaacg tcttctcatg ctccgtgatg catgaggctc tgcacaacca ctacacgcag      1680
aagagcctct ccctgtctcc gggtaaa                                          1707
```

<210> SEQ ID NO 4
<211> LENGTH: 569
<212> TYPE: PRT
<213> ORGANISM: Artificial Sequence
<220> FEATURE:
<223> OTHER INFORMATION: 838 molecule amino acid sequence

<400> SEQUENCE: 4

```
Met Glu Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320
```

Phe Val Arg Val His Glu Lys Pro Phe Val Ala Phe Gly Ser Gly Glu
                325                 330                 335
Phe Glu Pro Lys Ser Cys Asp Lys Thr His Thr Cys Pro Pro Cys Pro
            340                 345                 350
Ala Pro Glu Leu Leu Gly Gly Pro Ser Val Phe Leu Phe Pro Pro Lys
            355                 360                 365
Pro Lys Asp Thr Leu Met Ile Ser Arg Thr Pro Glu Val Thr Cys Val
        370                 375                 380
Val Val Asp Val Ser His Glu Asp Pro Glu Val Lys Phe Asn Trp Tyr
385                 390                 395                 400
Val Asp Gly Val Glu Val His Asn Ala Lys Thr Lys Pro Arg Glu Glu
                405                 410                 415
Gln Tyr Asn Ser Thr Tyr Arg Val Val Ser Val Leu Thr Val Leu His
            420                 425                 430
Gln Asp Trp Leu Asn Gly Lys Glu Tyr Lys Cys Lys Val Ser Asn Lys
        435                 440                 445
Ala Leu Pro Ala Pro Ile Glu Lys Thr Ile Ser Lys Ala Lys Gly Gln
    450                 455                 460
Pro Arg Glu Pro Gln Val Tyr Thr Leu Pro Pro Ser Arg Asp Glu Leu
465                 470                 475                 480
Thr Lys Asn Gln Val Ser Leu Thr Cys Leu Val Lys Gly Phe Tyr Pro
                485                 490                 495
Ser Asp Ile Ala Val Glu Trp Glu Ser Asn Gly Gln Pro Glu Asn Asn
            500                 505                 510
Tyr Lys Thr Thr Pro Pro Val Leu Asp Ser Asp Gly Ser Phe Phe Leu
        515                 520                 525
Tyr Ser Lys Leu Thr Val Asp Lys Ser Arg Trp Gln Gln Gly Asn Val
    530                 535                 540
Phe Ser Cys Ser Val Met His Glu Ala Leu His Asn His Tyr Thr Gln
545                 550                 555                 560
Lys Ser Leu Ser Leu Ser Pro Gly Lys
                565

<210> SEQ ID NO 5
<211> LENGTH: 858
<212> TYPE: DNA
<213> ORGANISM: Artificial Sequence
<220> FEATURE:
<223> OTHER INFORMATION: 876 molecule nucleic acid sequence

<400> SEQUENCE: 5
atggacatgc gggtgccagc tcagctgctg ggactgctgc tgctgtggct gcccggcacc      60
agatgcgaca tccagctgac ccagtccccc tccagcctgt ccgcctctgt gggcgacaga     120
gtgaccatca cctgttccgc ctcccaggac atcagcaact acctgaactg gtatcagcag     180
aagcccggca aggcccccaa ggtgctgatc tacttcacca gcagcctgca ctccggcgtg     240
ccctcccggt tctccggctc cggctccggc accgacttca ccctgaccat ctccagcctg     300
cagcccgagg acttcgccac ctactactgc cagcagtaca gcaccgtgcc ctggaccttc     360
ggccagggca ccaaggtgga aatcaaggga ggtggaggaa gcgtggagg aggtagcgga     420 ggcggcggca gcgaggtgca gctggtggaa tccggcggag actggtgca gcctggcggc     480 tccctgagac tgtcttgcgc cgcctccggc tacgacttca cccactacgg catgaactgg     540
gtccgacagg cccctggcaa gggactggaa tgggtgggct ggatcaacac ctacaccggc     600

```
gagcccacct acgccgccga cttcaagcgg cggttcacct tcagcctgga caccagcaag    660
agcaccgcct acctgcagat gaactccctg cgggccgagg acaccgccgt gtactactgc    720
gccaagtacc cctactacta cggcaccagc cactggtact cgacgtgtg gggccagggc    780 accctggtca ccgtctcctc acaccatcac caccaccaca ccctggtcac cgtctcctca    840
caccatcacc accaccac                                                  858
```

<210> SEQ ID NO 6
<211> LENGTH: 273
<212> TYPE: PRT
<213> ORGANISM: Artificial Sequence
<220> FEATURE:
<223> OTHER INFORMATION: 876 molecule amino acid sequence

<400> SEQUENCE: 6

```
Met Asp Met Arg Val Pro Ala Gln Leu Leu Gly Leu Leu Leu Leu Trp
1               5                   10                  15

Leu Pro Gly Thr Arg Cys Asp Ile Gln Leu Thr Gln Ser Pro Ser Ser
            20                  25                  30

Leu Ser Ala Ser Val Gly Asp Arg Val Thr Ile Thr Cys Ser Ala Ser
        35                  40                  45

Gln Asp Ile Ser Asn Tyr Leu Asn Trp Tyr Gln Gln Lys Pro Gly Lys
    50                  55                  60

Ala Pro Lys Val Leu Ile Tyr Phe Thr Ser Ser Leu His Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Ser Thr Val Pro Trp Thr Phe Gly Gln Gly Thr Lys Val Glu Ile
        115                 120                 125

Lys Gly Gly Gly Gly Ser Gly Gly Gly Gly Ser Gly Gly Gly Gly Ser
    130                 135                 140

Glu Val Gln Leu Val Glu Ser Gly Gly Gly Leu Val Gln Pro Gly Gly
145                 150                 155                 160

Ser Leu Arg Leu Ser Cys Ala Ala Ser Gly Tyr Asp Phe Thr His Tyr
                165                 170                 175

Gly Met Asn Trp Val Arg Gln Ala Pro Gly Lys Gly Leu Glu Trp Val
            180                 185                 190

Gly Trp Ile Asn Thr Tyr Thr Gly Glu Pro Thr Tyr Ala Ala Asp Phe
        195                 200                 205

Lys Arg Arg Phe Thr Phe Ser Leu Asp Thr Ser Lys Ser Thr Ala Tyr
    210                 215                 220

Leu Gln Met Asn Ser Leu Arg Ala Glu Asp Thr Ala Val Tyr Tyr Cys
225                 230                 235                 240

Ala Lys Tyr Pro Tyr Tyr Tyr Gly Thr Ser His Trp Tyr Phe Asp Val
                245                 250                 255

Trp Gly Gln Gly Thr Leu Val Thr Val Ser Ser His His His His His
            260                 265                 270

His
```

<210> SEQ ID NO 7
<211> LENGTH: 1371
<212> TYPE: DNA
<213> ORGANISM: Artificial Sequence
<220> FEATURE:

<223> OTHER INFORMATION: 873 molecule nucleic acid sequence

<400> SEQUENCE: 7

| | | | | | |
|---|---|---|---|---|---|
| atggtcagct | actgggacac | cggggtcctg | ctgtgcgcgc | tgctcagctg | tctgcttctc | 60 |
| acaggatcta | gttcaggtag | tgatacaggt | agacctttcg | tagagatgta | cagtgaaatc | 120 |
| cccgaaatta | tacacatgac | tgaaggaagg | gagctcgtca | ttccctgccg | ggttacgtca | 180 |
| cctaacatca | ctgttacttt | aaaaaagttt | ccacttgaca | ctttgatccc | tgatggaaaa | 240 |
| cgcataatct | gggacagtag | aaagggcttc | atcatatcaa | atgcaacgta | caaagaaata | 300 |
| gggcttctga | cctgtgaagc | aacagtcaat | gggcatttgt | ataagacaaa | ctatctcaca | 360 |
| catcgacaaa | ccaatacaat | catcgatgtg | gttctgagtc | cgtctcatgg | aattgaacta | 420 |
| tctgttggag | aaaagcttgt | cttaaattgt | acagcaagaa | ctgaactaaa | tgtggggatt | 480 |
| gacttcaact | gggaataccc | ttcttcgaag | catcagcata | agaaacttgt | aaaccgagac | 540 |
| ctaaaaccc | agtctgggag | tgagatgaag | aaatttttga | gcaccttaac | tatagatggt | 600 |
| gtaacccgga | gtgaccaagg | attgtacacc | tgtgcagcat | ccagtgggct | gatgaccaag | 660 |
| aagaacagca | catttgtcag | ggtccatgaa | aaagacaaaa | ctcacacatg | cccaccgtgc | 720 |
| ccagcacctg | aactcctggg | gggaccgtca | gtcttcctct | tccccccaaa | acccaaggac | 780 |
| accctcatga | tctcccggac | ccctgaggtc | acatgcgtgg | tggtggacgt | gagccacgaa | 840 |
| gaccctgagg | tcaagttcaa | ctggtacgtg | gacggcgtgg | aggtgcataa | tgccaagaca | 900 |
| aagccgcggg | aggagcagta | caacagcacg | taccgtgtgg | tcagcgtcct | caccgtcctg | 960 |
| caccaggact | ggctgaatgg | caaggagtac | aagtgcaagg | tctccaacaa | agccctccca | 1020 |
| gcccccatcg | agaaaaccat | ctccaaagcc | aaagggcagc | cccgagaacc | acaggtgtac | 1080 |
| accctgcccc | catcccggga | tgagctgacc | aagaaccagg | tcagcctgac | ctgcctggtc | 1140 |
| aaaggcttct | atcccagcga | catcgccgtg | gagtgggaga | gcaatgggca | gccggagaac | 1200 |
| aactacaaga | ccacgcctcc | cgtgctggac | tccgacggct | ccttcttcct | ctacagcaag | 1260 |
| ctcaccgtgg | acaagagcag | gtggcagcag | gggaacgtct | tctcatgctc | cgtgatgcat | 1320 |
| gaggctctgc | acaaccacta | cacgcagaag | agcctctccc | tgtctccggg | t | 1371 |

<210> SEQ ID NO 8
<211> LENGTH: 457
<212> TYPE: PRT
<213> ORGANISM: Artificial Sequence
<220> FEATURE:
<223> OTHER INFORMATION: 873 molecule amino acid sequence

<400> SEQUENCE: 8

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Asp Thr Gly Arg Pro
                20                  25                  30

Phe Val Glu Met Tyr Ser Glu Ile Pro Glu Ile Ile His Met Thr Glu
            35                  40                  45

Gly Arg Glu Leu Val Ile Pro Cys Arg Val Thr Ser Pro Asn Ile Thr
        50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His

```
                    100                 105                 110
Leu Tyr Lys Thr Asn Tyr Leu Thr His Arg Gln Thr Asn Thr Ile Ile
            115                 120                 125

Asp Val Val Leu Ser Pro Ser His Gly Ile Glu Leu Ser Val Gly Glu
130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly
    450                 455

<210> SEQ ID NO 9
<211> LENGTH: 1416
<212> TYPE: DNA
<213> ORGANISM: Artificial Sequence
<220> FEATURE:
<223> OTHER INFORMATION: 874 molecule nucleic acid sequence

<400> SEQUENCE: 9
atggactgga cctggtctat cctgttcctg gtggccgctg caaccggcac ctactccgag      60
```

```
gtgcagctgg tggaatccgg cggaggactg gtgcagcctg gcggctccct gagactgtct    120
tgcgccgcct ccggctacac cttcaccaac tacggcatga actgggtccg acaggcccct    180
ggcaagggac tggaatgggt gggctggatc aacacctaca ccggcgagcc cacctacgcc    240
gccgacttca gcggcggttt caccttcagc ctggacacca gcaagagcac cgcctacctg    300
cagatgaact ccctgcgggc cgaggacacc gccgtgtact actgcgccaa gtaccccac    360
tactacggca gcagccactg gtacttcgac gtgtggggcc agggcaccct ggtcaccgtc    420
tcctcagcct ccaccaaggg cccatcggtc ttccccctgg caccctcctc caagagcacc    480
tctgggggca gcggccctg ggctgcctg gtcaaggact acttccccga accggtgacg    540
gtgtcgtgga actcaggcgc cctgaccagc ggcgtgcaca ccttcccggc tgtcctacag    600
tcctcaggac tctactccct cagcagcgtg gtgaccgtgc cctccagcag cttgggcacc    660
cagacctaca tctgcaacgt gaatcacaag cccagcaaca ccaaggtgga caagaaagtt    720
gagcccaaat cttgtgacaa aactcacaca tgcccaccgt gcccagcacc tgaactcctg    780
gggggaccgt cagtcttcct cttccccca aaacccaagg acaccctcat gatctcccgg    840
accccctgagg tcacatgcgt ggtggtggac gtgagccacg aagaccctga ggtcaagttc    900
aactggtacg tggacggcgt ggaggtgcat aatgccaaga caaagccgcg ggaggagcag    960
tacaacagca cgtaccgtgt ggtcagcgtc ctcaccgtcc tgcaccagga ctggctgaat    1020
ggcaaggagt acaagtgcaa ggtctccaac aaagccctcc cagcccccat cgagaaaacc    1080
atctccaaag ccaaagggca gccccgagaa ccacaggtgt acaccctgcc cccatcccgg    1140
gatgagctga ccaagaacca ggtcagcctg acctgcctgg tcaaaggctt ctatcccagc    1200
gacatcgccg tggagtggga gagcaatggg cagccggaga caactacaa gaccacgcct    1260
cccgtgctgg actccgacgg ctccttcttc ctctacagca agctcaccgt ggacaagagc    1320
aggtggcagc aggggaacgt cttctcatgc tccgtgatgc atgaggctct gcacaaccac    1380
tacacgcaga agagcctctc cctgtctccg ggtaaa                              1416
```

<210> SEQ ID NO 10
<211> LENGTH: 472
<212> TYPE: PRT
<213> ORGANISM: Artificial Sequence
<220> FEATURE:
<223> OTHER INFORMATION: 874 molecule amino acid sequence

<400> SEQUENCE: 10

Met Asp Trp Thr Trp Ser Ile Leu Phe Leu Val Ala Ala Thr Gly
1               5                   10                  15

Thr Tyr Ser Glu Val Gln Leu Val Glu Ser Gly Gly Gly Leu Val Gln
                20                  25                  30

Pro Gly Gly Ser Leu Arg Leu Ser Cys Ala Ala Ser Gly Tyr Thr Phe
            35                  40                  45

Thr Asn Tyr Gly Met Asn Trp Val Arg Gln Ala Pro Gly Lys Gly Leu
        50                  55                  60

Glu Trp Val Gly Trp Ile Asn Thr Tyr Thr Gly Glu Pro Thr Tyr Ala
65                  70                  75                  80

Ala Asp Phe Lys Arg Arg Phe Thr Phe Ser Leu Asp Thr Ser Lys Ser
                85                  90                  95

Thr Ala Tyr Leu Gln Met Asn Ser Leu Arg Ala Glu Asp Thr Ala Val
            100                 105                 110

Tyr Tyr Cys Ala Lys Tyr Pro His Tyr Tyr Gly Ser Ser His Trp Tyr

```
                    115                 120                 125
Phe Asp Val Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470

<210> SEQ ID NO 11
<211> LENGTH: 708
<212> TYPE: DNA
<213> ORGANISM: Artificial Sequence
<220> FEATURE:
<223> OTHER INFORMATION: 875 molecule nucleic acid sequence

<400> SEQUENCE: 11
atggacatgc gggtgccagc tcagctgctg ggactgctgc tgctgtggct gcccggcacc      60
```

```
agatgcgaca tccagatgac ccagtccccc tccagcctgt ccgcctctgt gggcgacaga    120
gtgaccatca cctgttccgc ctcccaggac atcagcaact acctgaactg gtatcagcag    180
aagcccggca aggcccccaa ggtgctgatc tacttcacca gcagcctgca ctccggcgtg    240
ccctcccggt tctccggctc cggctccggc accgacttca ccctgaccat ctccagcctg    300
cagcccgagg acttcgccac ctactactgc cagcagtaca gcaccgtgcc ctggaccttc    360
ggccagggca ccaaggtgga aatcaagcgg accgtggccg ctcccccgt gttcatcttc    420 ccacccctccg acgagcagct gaagtccggc accgcctccg tcgtctgcct gctgaacaac    480 ttctacccccc gcgaggccaa ggtgcagtgg aaggtggaca acgccctgca gtccggcaac    540
tcccaggaat ccgtcaccga gcaggactcc aaggacagca cctactccct gtcctccacc    600
ctgaccctgt ccaaggccga ctacgagaag cacaaggtgt acgcctgcga agtgacccac    660
cagggcctgt ccagccccgt gaccaagtcc ttcaaccggg gcgagtgc                 708
```

<210> SEQ ID NO 12
<211> LENGTH: 236
<212> TYPE: PRT
<213> ORGANISM: Artificial Sequence
<220> FEATURE:
<223> OTHER INFORMATION: 875 molecule amino acid sequence

<400> SEQUENCE: 12

```
Met Asp Met Arg Val Pro Ala Gln Leu Leu Gly Leu Leu Leu Leu Trp
1               5                   10                  15

Leu Pro Gly Thr Arg Cys Asp Ile Gln Met Thr Gln Ser Pro Ser Ser
            20                  25                  30

Leu Ser Ala Ser Val Gly Asp Arg Val Thr Ile Thr Cys Ser Ala Ser
        35                  40                  45

Gln Asp Ile Ser Asn Tyr Leu Asn Trp Tyr Gln Gln Lys Pro Gly Lys
    50                  55                  60

Ala Pro Lys Val Leu Ile Tyr Phe Thr Ser Ser Leu His Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Ser Thr Val Pro Trp Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 13
<211> LENGTH: 750
<212> TYPE: DNA
<213> ORGANISM: Artificial Sequence
<220> FEATURE:
<223> OTHER INFORMATION: 915 molecule nucleic acid sequence

<400> SEQUENCE: 13

```
atggactgga cctggtctat cctgttcctg gtggccgctg caaccggcac ctactccgag      60
gtgcagctgg tggaatccgg cggaggactg gtgcagcctg gcggctccct gagactgtct     120
tgcgccgcct ccggctacga cttcacccac tacggcatga actgggtccg acaggcccct     180
ggcaagggac tggaatgggt gggctggatc aacacctaca ccggcgagcc cacctacgcc     240
gccgacttca gcggcggtt caccttcagc ctggacacca gcaagagcac cgcctacctg     300
cagatgaact ccctgcgggc cgaggacacc gccgtgtact actgcgccaa gtaccnctac     360
tactacggca ccagccactg gtacttcgac gtgtggggcc agggcaccct ggtcaccgtc     420
tcctcagcct ccaccaaggg cccatcggtc ttccccctgg cacctcctc caagagcacc     480
tctgggggca gcggccct gggctgcctg gtcaaggact acttccccga accggtgacg     540
gtgtcgtgga actcaggcgc cctgaccagc ggcgtgcaca ccttcccggc tgtcctacag     600
tcctcaggac tctactccct cagcagcgtg gtgaccgtgc cctccagcag cttgggcacc     660
cagacctaca tctgcaacgt gaatcacaag cccagcaaca ccaaggtgga caagaaagtt     720
gagcccaaat cttgtgacaa aactcacctg                                     750
```

<210> SEQ ID NO 14
<211> LENGTH: 250
<212> TYPE: PRT
<213> ORGANISM: Artificial Sequence
<220> FEATURE:
<223> OTHER INFORMATION: 915 molecule amino acid sequence

<400> SEQUENCE: 14

```
Met Asp Trp Thr Trp Ser Ile Leu Phe Leu Val Ala Ala Ala Thr Gly
1               5                   10                  15

Thr Tyr Ser Glu Val Gln Leu Val Glu Ser Gly Gly Gly Leu Val Gln
            20                  25                  30

Pro Gly Gly Ser Leu Arg Leu Ser Cys Ala Ala Ser Gly Tyr Asp Phe
        35                  40                  45

Thr His Tyr Gly Met Asn Trp Val Arg Gln Ala Pro Gly Lys Gly Leu
    50                  55                  60

Glu Trp Val Gly Trp Ile Asn Thr Tyr Thr Gly Glu Pro Thr Tyr Ala
65                  70                  75                  80

Ala Asp Phe Lys Arg Arg Phe Thr Phe Ser Leu Asp Thr Ser Lys Ser
                85                  90                  95

Thr Ala Tyr Leu Gln Met Asn Ser Leu Arg Ala Glu Asp Thr Ala Val
            100                 105                 110

Tyr Tyr Cys Ala Lys Tyr Pro Tyr Tyr Tyr Gly Thr Ser His Trp Tyr
        115                 120                 125

Phe Asp Val Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
```

His Thr Phe Pro Ala Val Leu Gln Ser Ser Gly Leu Tyr Ser Leu Ser
            180                 185                 190
Ser Val Val Thr Val Pro Ser Ser Ser Leu Gly Thr Gln Thr Tyr Ile
        195                 200                 205
Cys Asn Val Asn His Lys Pro Ser Asn Thr Lys Val Asp Lys Lys Val
210                 215                 220
225         230                 235                 240
Glu Pro Lys Ser Cys Asp Lys Thr His Leu
                245                 250

<210> SEQ ID NO 15
<211> LENGTH: 708
<212> TYPE: DNA
<213> ORGANISM: Artificial Sequence
<220> FEATURE:
<223> OTHER INFORMATION: 914 molecule nucleic acid sequence

<400> SEQUENCE: 15

```
atggacatgc gggtgccagc tcagctgctg ggactgctgc tgctgtggct gcccggcacc      60
agatgcgaca tccagctgac ccagtccccc tccagcctgt ccgcctctgt gggcgacaga     120
gtgaccatca cctgttccgc ctcccaggac atcagcaact acctgaactg gtatcagcag     180
aagcccggca aggcccccaa ggtgctgatc tacttcacca gcagcctgca ctccggcgtg     240
ccctcccggt tctccggctc cggctccggc accgacttca ccctgaccat ctccagcctg     300
cagcccgagg acttcgccac ctactactgc cagcagtaca gcaccgtgcc ctggaccttc     360
ggccagggca ccaaggtgga aatcaagcgg accgtggccg ctcccctccgt gttcatcttc     420
ccaccctccg acgagcagct gaagtccggc accgcctccg tcgtctgcct gctgaacaac     480
ttctacccccc gcgaggccaa ggtgcagtgg aaggtggaca cgccctgca gtccggcaac     540
tcccaggaat ccgtcaccga gcaggactcc aaggacagca cctactccct gtcctccacc     600
ctgaccctgt ccaaggccga ctacgagaag cacaaggtgt acgcctgcga agtgacccac     660
cagggcctgt ccagccccgt gaccaagtcc ttcaaccggg gcgagtgc                   708
```

<210> SEQ ID NO 16
<211> LENGTH: 236
<212> TYPE: PRT
<213> ORGANISM: Artificial Sequence
<220> FEATURE:
<223> OTHER INFORMATION: 914 molecule amino acid sequence

<400> SEQUENCE: 16

Met Asp Met Arg Val Pro Ala Gln Leu Leu Gly Leu Leu Leu Leu Trp
1               5                   10                  15
Leu Pro Gly Thr Arg Cys Asp Ile Gln Leu Thr Gln Ser Pro Ser Ser
            20                  25                  30
Leu Ser Ala Ser Val Gly Asp Arg Val Thr Ile Thr Cys Ser Ala Ser
        35                  40                  45
Gln Asp Ile Ser Asn Tyr Leu Asn Trp Tyr Gln Gln Lys Pro Gly Lys
    50                  55                  60
Ala Pro Lys Val Leu Ile Tyr Phe Thr Ser Ser Leu His Ser Gly Val
65                  70                  75                  80
Pro Ser Arg Phe Ser Gly Ser Gly Ser Gly Thr Asp Phe Thr Leu Thr
                85                  90                  95
Ile Ser Ser Leu Gln Pro Glu Asp Phe Ala Thr Tyr Tyr Cys Gln Gln
            100                 105                 110

```
Tyr Ser Thr Val Pro Trp Thr Phe Gly Gln Gly Thr Lys Val Glu Ile
            115                 120                 125
Lys Arg Thr Val Ala Ala Pro Ser Val Phe Ile Phe Pro Pro Ser Asp
        130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
            180                 185                 190
Ser Thr Tyr Ser Leu Ser Ser Thr Leu Thr Leu Ser Lys Ala Asp Tyr
        195                 200                 205
Glu Lys His Lys Val Tyr Ala Cys Glu Val Thr His Gln Gly Leu Ser
    210                 215                 220
Ser Pro Val Thr Lys Ser Phe Asn Arg Gly Glu Cys
225                 230                 235

<210> SEQ ID NO 17
<211> LENGTH: 1416
<212> TYPE: DNA
<213> ORGANISM: Artificial Sequence
<220> FEATURE:
<223> OTHER INFORMATION: 916 molecule nucleic acid sequence

<400> SEQUENCE: 17
atggactgga cctggtctat cctgttcctg gtggccgctg caaccggcac ctactccgag      60
gtgcagctgg tggaatccgg cggaggactg gtgcagcctg gcggctccct gagactgtct     120
tgcgccgcct ccggctacga cttcacccac tacggcatga actgggtccg acaggcccct     180
ggcaagggac tggaatgggt gggctggatc aacacctaca ccggcgagcc cacctacgcc     240
gccgacttca gcggcggtt caccttcagc ctggacacca gcaagagcac cgcctacctg     300
cagatgaact ccctgcgggc cgaggacacc gccgtgtact actgcgccaa gtaccctac     360
tactacggca ccagccactg gtacttcgac gtgtggggcc agggcaccct ggtcaccgtc     420
tcctcagcct ccaccaaggg cccatcggtc ttccccctgg cacctcctc caagagcacc     480
tctgggggca gcggccct gggctgcctg gtcaaggact acttccccga accggtgacg     540
gtgtcgtgga actcaggcgc cctgaccagc ggcgtgcaca ccttcccggc tgtcctacag     600
tcctcaggac tctactccct cagcagcgtg gtgaccgtgc cctccagcag cttgggcacc     660
cagacctaca tctgcaacgt gaatcacaag cccagcaaca ccaaggtgga caagaaagtt     720
gagcccaaat cttgtgacaa aactcacaca tgcccaccgt gcccagcacc tgaactcctg     780
gggggaccgt cagtcttcct cttccccca aaacccaagg acaccctcat gatctcccgg     840
acccctgagg tcacatgcgt ggtggtggac gtgagccacg aagaccctga ggtcaagttc     900
aactggtacg tggacggcgt ggaggtgcat aatgccaaga caaagccgcg ggaggagcag     960
tacaacagca cgtaccgtgt ggtcagcgtc ctcaccgtcc tgcaccagga ctggctgaat    1020
ggcaaggagt acaagtgcaa ggtctccaac aaagccctcc cagcccccat cgagaaaacc    1080
atctccaaag ccaaagggca gccccgagaa ccacaggtgt acaccctgcc cccatcccgg    1140
gatgagctga ccaagaacca ggtcagcctg acctgcctgg tcaaaggctt ctatcccagc    1200
gacatcgccg tggagtggga gagcaatggg cagccggaga acaactacaa gaccacgcct    1260
cccgtgctgg actccgacgg ctccttcttc ctctacagca agctcaccgt ggacaagagc    1320
aggtggcagc aggggaacgt cttctcatgc tccgtgatgc atgaggctct gcacaaccac    1380
```
tacacgcaga agagcctctc cctgtctccg ggtaaa                                     1416

<210> SEQ ID NO 18
<211> LENGTH: 472
<212> TYPE: PRT
<213> ORGANISM: Artificial Sequence
<220> FEATURE:
<223> OTHER INFORMATION: 916 molecule amino acid sequence

<400> SEQUENCE: 18

```
Met Asp Trp Thr Trp Ser Ile Leu Phe Leu Val Ala Ala Thr Gly
1               5                   10                  15

Thr Tyr Ser Glu Val Gln Leu Val Glu Ser Gly Gly Gly Leu Val Gln
            20                  25                  30

Pro Gly Gly Ser Leu Arg Leu Ser Cys Ala Ala Ser Gly Tyr Asp Phe
        35                  40                  45

Thr His Tyr Gly Met Asn Trp Val Arg Gln Ala Pro Gly Lys Gly Leu
    50                  55                  60

Glu Trp Val Gly Trp Ile Asn Thr Tyr Thr Gly Glu Pro Thr Tyr Ala
65                  70                  75                  80

Ala Asp Phe Lys Arg Arg Phe Thr Phe Ser Leu Asp Thr Ser Lys Ser
                85                  90                  95

Thr Ala Tyr Leu Gln Met Asn Ser Leu Arg Ala Glu Asp Thr Ala Val
            100                 105                 110

Tyr Tyr Cys Ala Lys Tyr Pro Tyr Tyr Tyr Gly Thr Ser His Trp Tyr
        115                 120                 125

Phe Asp Val Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350
```

```
Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Asp Glu Leu Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470

<210> SEQ ID NO 19
<211> LENGTH: 801
<212> TYPE: DNA
<213> ORGANISM: Artificial Sequence
<220> FEATURE:
<223> OTHER INFORMATION: 913 molecule nucleic acid sequence

<400> SEQUENCE: 19
atggacatgc gggtgccagc tcagctgctg ggactgctgc tgctgtggct gcccggcacc      60
agatgcgaca tccagctgac ccagtccccc tccagcctgt ccgcctctgt gggcgacaga     120
gtgaccatca cctgttccgc ctcccaggac atcagcaact acctgaactg gtatcagcag     180
aagcccggca aggcccccaa ggtgctgatc tacttcacca gcagcctgca ctccggcgtg     240
ccctcccggt tctccggctc cggctccggc accgacttca ccctgaccat ctccagcctg     300
cagcccgagg acttcgccac ctactactgc cagcagtaca gcaccgtgcc ctggaccttc     360
ggccagggca ccaaggtgga aatcaaggga ggtggaggaa gcggtggagg aggtagcgga     420
ggcggcggca gcgaggtgca gctggtggaa tccggcggag actggtgcag cctggcggc      480
tccctgagac tgtcttgcgc cgcctccggc tacgacttca cccactacgg catgaactgg     540
gtccgacagg ccctggcaa gggactggaa tgggtgggct ggatcaacac ctacaccggc     600
gagcccacct acgccgccga cttcaagcgg cggttcacct tcagcctgga caccagcaag     660
agcaccgcct acctgcagat gaactccctg cgggccgagg acaccgccgt gtactactgc     720
gccaagtacc cctactacta cggcaccagc cactggtact cgacgtgtg gggccagggc     780
accctggtca ccgtctcctc a                                               801

<210> SEQ ID NO 20
<211> LENGTH: 267
<212> TYPE: PRT
<213> ORGANISM: Artificial Sequence
<220> FEATURE:
<223> OTHER INFORMATION: 913 molecule amino acid sequence

<400> SEQUENCE: 20

Met Asp Met Arg Val Pro Ala Gln Leu Leu Gly Leu Leu Leu Leu Trp
1               5                   10                  15

Leu Pro Gly Thr Arg Cys Asp Ile Gln Leu Thr Gln Ser Pro Ser Ser
            20                  25                  30

Leu Ser Ala Ser Val Gly Asp Arg Val Thr Ile Thr Cys Ser Ala Ser
```

```
                 35                  40                  45
Gln Asp Ile Ser Asn Tyr Leu Asn Trp Tyr Gln Gln Lys Pro Gly Lys
         50                  55                  60

Ala Pro Lys Val Leu Ile Tyr Phe Thr Ser Ser Leu His Ser Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Phe Ala Thr Tyr Tyr Cys Gln Gln
            100                 105                 110

Tyr Ser Thr Val Pro Trp Thr Phe Gly Gln Gly Thr Lys Val Glu Ile
            115                 120                 125

Lys Gly Gly Gly Ser Gly Gly Gly Ser Gly Gly Gly Gly Ser
        130                 135                 140

Glu Val Gln Leu Val Glu Ser Gly Gly Gly Leu Val Gln Pro Gly Gly
145                 150                 155                 160

Ser Leu Arg Leu Ser Cys Ala Ala Ser Gly Tyr Asp Phe Thr His Tyr
                165                 170                 175

Gly Met Asn Trp Val Arg Gln Ala Pro Gly Lys Gly Leu Glu Trp Val
            180                 185                 190

Gly Trp Ile Asn Thr Tyr Thr Gly Glu Pro Thr Tyr Ala Ala Asp Phe
            195                 200                 205

Lys Arg Arg Phe Thr Phe Ser Leu Asp Thr Ser Lys Ser Thr Ala Tyr
210                 215                 220

Leu Gln Met Asn Ser Leu Arg Ala Glu Asp Thr Ala Val Tyr Tyr Cys
225                 230                 235                 240

Ala Lys Tyr Pro Tyr Tyr Tyr Gly Thr Ser His Trp Tyr Phe Asp Val
                245                 250                 255

Trp Gly Gln Gly Thr Leu Val Thr Val Ser Ser
            260                 265

<210> SEQ ID NO 21
<211> LENGTH: 1377
<212> TYPE: DNA
<213> ORGANISM: Artificial Sequence
<220> FEATURE:
<223> OTHER INFORMATION: 917 molecule nucleic acid sequence

<400> SEQUENCE: 21
atggtcagct actgggacac cggggtcctg ctgtgcgcgc tgctcagctg tctgcttctc      60
acaggatcta gttcaggttc gcgaagtgat acaggtagac ctttcgtaga gatgtacagt    120
gaaatccccg aaattataca catgactgaa ggaagggagc tcgtcattcc ctgccggggtt   180 acgtcaccta acatcactgt tactttaaaa aagtttccac ttgacacttt gatccctgat    240
ggaaaacgca taatctggga cagtagaaag ggcttcatca tatcaaatgc aacgtacaaa    300
gaaatagggc ttctgacctg tgaagcaaca gtcaatgggc atttgtataa gacaaactat    360
ctcacacatc gacaaaccaa tacaatcatc gatgtggttc tgagtccgtc tcatggaatt    420
gaactatctg ttggagaaaa gcttgtctta aattgtacag caagaactga actaaatgtg    480
gggattgact tcaactggga ataccttct tcgaagcatc agcataagaa acttgtaaac    540
cgagacctaa aacccagtc tgggagtgag atgaagaaat ttttgagcac cttaactata    600
gatggtgtaa cccggagtga ccaaggattg tacacctgtg cagcatccag tgggctgatg    660
accaagaaga cagcacatt tgtcagggtc catgaaaaag acaaaactca cacatgccca    720
ccgtgcccag cacctgaact cctgggggga ccgtcagtct tcctcttccc cccaaaaccc    780
```

```
aaggacaccc tcatgatctc ccggacccct gaggtcacat gcgtggtggt ggacgtgagc    840
cacgaagacc ctgaggtcaa gttcaactgg tacgtggacg gcgtggaggt gcataatgcc    900
aagacaaagc cgcgggagga gcagtacaac agcacgtacc gtgtggtcag cgtcctcacc    960
gtcctgcacc aggactggct gaatggcaag gagtacaagt gcaaggtctc caacaaagcc   1020
ctcccagccc ccatcgagaa aaccatctcc aaagccaaag gcagccccg agaaccacag    1080 gtgtacaccc tgcccccatc ccgggatgag ctgaccaaga accaggtcag cctgacctgc   1140
ctggtcaaag gcttctatcc cagcgacatc gccgtggagt gggagagcaa tgggcagccg   1200
gagaacaact acaagaccac gcctcccgtg ctggactccg acggctcctt cttcctctac   1260
agcaagctca ccgtggacaa gagcaggtgg cagcagggga acgtcttctc atgctccgtg   1320
atgcatgagg ctctgcacaa ccactacacg cagaagagcc tctccctgtc tccgggt     1377
```

<210> SEQ ID NO 22
<211> LENGTH: 459
<212> TYPE: PRT
<213> ORGANISM: Artificial Sequence
<220> FEATURE:
<223> OTHER INFORMATION: 917 molecule amino acid sequence

<400> SEQUENCE: 22

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Arg Ser Asp Thr Gly
            20                  25                  30

Arg Pro Phe Val Glu Met Tyr Ser Glu Ile Pro Glu Ile Ile His Met
        35                  40                  45

Thr Glu Gly Arg Glu Leu Val Ile Pro Cys Arg Val Thr Ser Pro Asn
50                  55                  60

Ile Thr Val Thr Leu Lys Lys Phe Pro Leu Asp Thr Leu Ile Pro Asp
65                  70                  75                  80

Gly Lys Arg Ile Ile Trp Asp Ser Arg Lys Gly Phe Ile Ile Ser Asn
                85                  90                  95

Ala Thr Tyr Lys Glu Ile Gly Leu Leu Thr Cys Glu Ala Thr Val Asn
            100                 105                 110

Gly His Leu Tyr Lys Thr Asn Tyr Leu Thr His Arg Gln Thr Asn Thr
        115                 120                 125

Ile Ile Asp Val Val Leu Ser Pro Ser His Gly Ile Glu Leu Ser Val
130                 135                 140

Gly Glu Lys Leu Val Leu Asn Cys Thr Ala Arg Thr Glu Leu Asn Val
145                 150                 155                 160

Gly Ile Asp Phe Asn Trp Glu Tyr Pro Ser Ser Lys His Gln His Lys
                165                 170                 175

Lys Leu Val Asn Arg Asp Leu Lys Thr Gln Ser Gly Ser Glu Met Lys
            180                 185                 190

Lys Phe Leu Ser Thr Leu Thr Ile Asp Gly Val Thr Arg Ser Asp Gln
        195                 200                 205

Gly Leu Tyr Thr Cys Ala Ala Ser Ser Gly Leu Met Thr Lys Lys Asn
    210                 215                 220

Ser Thr Phe Val Arg Val His Glu Lys Asp Lys Thr His Thr Cys Pro
225                 230                 235                 240

Pro Cys Pro Ala Pro Glu Leu Leu Gly Gly Pro Ser Val Phe Leu Phe
                245                 250                 255
```

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365

Asp Glu Leu Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly
    450                 455

<210> SEQ ID NO 23
<211> LENGTH: 2265
<212> TYPE: DNA
<213> ORGANISM: Artificial Sequence
<220> FEATURE:
<223> OTHER INFORMATION: 964 molecule nucleic acid sequence

<400> SEQUENCE: 23

| | | | | | |
|---|---|---|---|---|---|
| atgcggcttc | cgggtgcgat | gccagctctg | gccctcaaag | gcgagctgct | gttgctgtct | 60 |
| ctcctgttac | ttctggaacc | acagatctct | cagggcctgg | tcgtcacacc | cccggggcca | 120 |
| gagcttgtcc | tcaatgtctc | cagcaccttc | gttctgacct | gctcgggttc | agctccggtg | 180 |
| gtgtgggaac | ggatgtccca | ggagcccca | caggaaatgg | ccaaggccca | ggatggcacc | 240 |
| ttctccagcg | tgctcacact | gaccaacctc | actgggctag | acacgggaga | atactttgc | 300 |
| acccacaatg | actcccgtgg | actggagacc | gatgagcgga | aacggctcta | catctttgtg | 360 |
| ccagatccca | ccgtgggctt | cctccctaat | gatgccgagg | aactattcat | ctttctcacg | 420 |
| gaaataactg | agatcaccat | tccatgccga | gtaacagacc | cacagctggt | ggtgacactg | 480 |
| cacgagaaga | aagggacgt | tgcactgcct | gtcccctatg | atcaccaacg | tggcttttct | 540 |
| ggtatctttg | aggacagaag | ctacatctgc | aaaaccacca | ttggggacag | ggaggtggat | 600 |
| tctgatgcct | actatgtcta | cagactccag | gtgtcatcca | tcaacgtctc | tgtgaacgca | 660 |
| gtgcagactg | tggtccgcca | gggtgagaac | atcaccctca | tgtgcattgt | gatcgggaat | 720 |
| gaggtggtca | acttcgagtg | gacatacccc | cgcaaagaaa | gtgggcggct | ggtggagccg | 780 |
| gtgactgact | tcctcttgga | tatgccttac | cacatccgct | ccatcctgca | catccccagt | 840 |
| gccgagttag | aagactcggg | gacctacacc | tgcaatgtga | cggagagtgt | gaatgaccat | 900 |

```
caggatgaaa aggccatcaa catcaccgtg gttgagagcg gctacgtgcg gctcctggga      960
gaggtgggca cactacaatt tgctgagctg catcggagcc ggacactgca ggtagtgttc     1020
gaggcctacc caccgcccac tgtcctgtgg ttcaaagaca accgcaccct gggcgactcc     1080
agcgctggcg aaatcgccct gtccacgcgc aacgtgtcgg agacccggta tgtgtcagag     1140
ctgacactgg ttcgcgtgaa ggtggcagag gctggccact acaccatgcg ggccttccat     1200
gaggatgctg aggtccagct ctccttccag ctacagatca atgtccctgt ccgagtgctg     1260
gagctaagtg agagccaccc tgacagtggg gaacagacag tccgctgtcg tggccggggc     1320
atgccccagc cgaacatcat ctggtctgcc tgcagagacc tcaaaaggtg tccacgtgag     1380
ctgccgccca cgctgctggg aacagttcc gaagaggaga gccagctgga gactaacgtg      1440
acgtactggg aggaggagca ggagtttgag gtggtgagca cactgcgtct gcagcacgtg     1500
gatcggccac tgtcggtgcg ctgcacgctg cgcaacgctg tgggccagga cacgcaggag     1560
gtcatcgtgg tgccacactc cttgcccttc aagcccccat gcccatcatg cccagcacct     1620
gagttcctgg ggggaccatc agtcttcctg ttcccccaa acccaaagga cactctcatg      1680
atctcccgga cccctgaggt cacgtgcgtg gtggtggacg tgagccagga agaccccgag     1740
gtccagttca actggtacgt ggatggcgtg gaggtgcata atgccaagac aaagccgcgg     1800
gaggagcagt tcaacagcac gtaccgtgtg gtcagcgtcc tcaccgtcct gcaccaggac     1860
tggctgaacg gcaaggagta caagtgcaag gtctccaaca aaggcctccc gtcctccatc     1920
gagaaaacca tctccaaagc caaagggcag ccccgagagc cacaggtgta caccctgccc     1980
ccatcccagg aggagatgac caagaaccag gtcagcctga cctgcctggt caaaggcttc     2040
taccccagcg acatcgccgt ggagtgggag agcaatgggc agccggagaa caactacaag     2100
accacgcctc ccgtgctgga ctccgacggc tccttcttcc tctacagcag gctaaccgtg     2160
gacaagagca ggtggcagga ggggaatgtc ttctcatgct ccgtgatgca tgaggctctg     2220
cacaaccact acacacagaa gagcctctcc ctgtctctgg gtaaa                     2265
```

<210> SEQ ID NO 24
<211> LENGTH: 755
<212> TYPE: PRT
<213> ORGANISM: Artificial Sequence
<220> FEATURE:
<223> OTHER INFORMATION: 964 molecule amino acid sequence

<400> SEQUENCE: 24

```
Met Arg Leu Pro Gly Ala Met Pro Ala Leu Ala Leu Lys Gly Glu Leu
1               5                  10                  15

Leu Leu Leu Ser Leu Leu Leu Leu Glu Pro Gln Ile Ser Gln Gly
            20                  25                  30

Leu Val Val Thr Pro Pro Gly Pro Glu Leu Val Leu Asn Val Ser Ser
        35                  40                  45

Thr Phe Val Leu Thr Cys Ser Gly Ser Ala Pro Val Val Trp Glu Arg
    50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                85                  90                  95

Glu Tyr Phe Cys Thr His Asn Asp Ser Arg Gly Leu Glu Thr Asp Glu
            100                 105                 110

Arg Lys Arg Leu Tyr Ile Phe Val Pro Asp Pro Thr Val Gly Phe Leu
        115                 120                 125
```

```
Pro Asn Asp Ala Glu Glu Leu Phe Ile Phe Leu Thr Glu Ile Thr Glu
    130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
                165                 170                 175

Arg Gly Phe Ser Gly Ile Phe Glu Asp Arg Ser Tyr Ile Cys Lys Thr
                180                 185                 190

Thr Ile Gly Asp Arg Glu Val Asp Ser Asp Ala Tyr Tyr Val Tyr Arg
            195                 200                 205

Leu Gln Val Ser Ser Ile Asn Val Ser Val Asn Ala Val Gln Thr Val
    210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
                245                 250                 255

Leu Val Glu Pro Val Thr Asp Phe Leu Leu Asp Met Pro Tyr His Ile
            260                 265                 270

Arg Ser Ile Leu His Ile Pro Ser Ala Glu Leu Glu Asp Ser Gly Thr
            275                 280                 285

Tyr Thr Cys Asn Val Thr Glu Ser Val Asn Asp His Gln Asp Glu Lys
    290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
                325                 330                 335

Gln Val Val Phe Glu Ala Tyr Pro Pro Pro Thr Val Leu Trp Phe Lys
            340                 345                 350

Asp Asn Arg Thr Leu Gly Asp Ser Ser Ala Gly Glu Ile Ala Leu Ser
            355                 360                 365

Thr Arg Asn Val Ser Glu Thr Arg Tyr Val Ser Glu Leu Thr Leu Val
    370                 375                 380

Arg Val Lys Val Ala Glu Ala Gly His Tyr Thr Met Arg Ala Phe His
385                 390                 395                 400

Glu Asp Ala Glu Val Gln Leu Ser Phe Gln Leu Gln Ile Asn Val Pro
                405                 410                 415

Val Arg Val Leu Glu Leu Ser Glu Ser His Pro Asp Ser Gly Glu Gln
            420                 425                 430

Thr Val Arg Cys Arg Gly Arg Gly Met Pro Gln Pro Asn Ile Ile Trp
    435                 440                 445

Ser Ala Cys Arg Asp Leu Lys Arg Cys Pro Arg Glu Leu Pro Pro Thr
450                 455                 460

Leu Leu Gly Asn Ser Ser Glu Glu Glu Ser Gln Leu Glu Thr Asn Val
465                 470                 475                 480

Thr Tyr Trp Glu Glu Glu Gln Glu Phe Glu Val Val Ser Thr Leu Arg
                485                 490                 495

Leu Gln His Val Asp Arg Pro Leu Ser Val Arg Cys Thr Leu Arg Asn
            500                 505                 510

Ala Val Gly Gln Asp Thr Gln Glu Val Ile Val Val Pro His Ser Leu
    515                 520                 525

Pro Phe Lys Pro Pro Cys Pro Ser Cys Pro Ala Pro Glu Phe Leu Gly
530                 535                 540
```

Gly Pro Ser Val Phe Leu Phe Pro Pro Lys Pro Lys Asp Thr Leu Met
545                 550                 555                 560

Ile Ser Arg Thr Pro Glu Val Thr Cys Val Val Val Asp Val Ser Gln
            565                 570                 575

Glu Asp Pro Glu Val Gln Phe Asn Trp Tyr Val Asp Gly Val Glu Val
        580                 585                 590

His Asn Ala Lys Thr Lys Pro Arg Glu Glu Gln Phe Asn Ser Thr Tyr
    595                 600                 605

Arg Val Val Ser Val Leu Thr Val Leu His Gln Asp Trp Leu Asn Gly
610                 615                 620

Lys Glu Tyr Lys Cys Lys Val Ser Asn Lys Gly Leu Pro Ser Ser Ile
625                 630                 635                 640

Glu Lys Thr Ile Ser Lys Ala Lys Gly Gln Pro Arg Glu Pro Gln Val
                645                 650                 655

Tyr Thr Leu Pro Pro Ser Gln Glu Glu Met Thr Lys Asn Gln Val Ser
            660                 665                 670

Leu Thr Cys Leu Val Lys Gly Phe Tyr Pro Ser Asp Ile Ala Val Glu
        675                 680                 685

Trp Glu Ser Asn Gly Gln Pro Glu Asn Asn Tyr Lys Thr Thr Pro Pro
690                 695                 700

Val Leu Asp Ser Asp Gly Ser Phe Phe Leu Tyr Ser Arg Leu Thr Val
705                 710                 715                 720

Asp Lys Ser Arg Trp Gln Glu Gly Asn Val Phe Ser Cys Ser Val Met
                725                 730                 735

His Glu Ala Leu His Asn His Tyr Thr Gln Lys Ser Leu Ser Leu Ser
            740                 745                 750

Leu Gly Lys
        755

<210> SEQ ID NO 25
<211> LENGTH: 2295
<212> TYPE: DNA
<213> ORGANISM: Artificial Sequence
<220> FEATURE:
<223> OTHER INFORMATION: 963 molecule nucleic acid sequence

<400> SEQUENCE: 25
atgcggcttc cgggtgcgat gccagctctg gccctcaaag gcgagctgct gttgctgtct    60
ctcctgttac ttctggaacc acagatctct cagggcctgg tcgtcacacc cccggggcca   120
gagcttgtcc tcaatgtctc cagcaccttc gttctgacct gctcgggttc agctccggtg   180
gtgtgggaac ggatgtccca ggagccccca caggaaatgg ccaaggccca ggatggcacc   240
ttctccagcg tgctcacact gaccaacctc actgggctag acacgggaga atacttttgc   300
acccacaatg actcccgtgg actggagacc gatgagcgga acggctcta catctttgtg   360 ccagatccca ccgtgggctt cctccctaat gatgccgagg aactattcat ctttctcacg   420
gaaataactg agatcaccat tccatgccga gtaacagacc acagctggt ggtgacactg   480 cacgagaaga aggggacgt tgcactgcct gtccctatg atcaccaacg tggcttttct   540
ggtatctttg aggacagaag ctacatctgc aaaaccacca ttggggacag ggaggtggat   600
tctgatgcct actatgtcta cagactccag gtgtcatcca tcaacgtctc tgtgaacgca   660
gtgcagactg tggtccgcca gggtgagaac atcaccctca tgcattgt gatcgggaat   720 gaggtggtca acttcgagtg gacatacccc cgcaaagaaa gtgggcggct ggtggagccg   780
gtgactgact tcctcttgga tatgccttac acatccgct ccatcctgca catccccagt   840

```
gccgagttag aagactcggg gacctacacc tgcaatgtga cggagagtgt gaatgaccat    900
caggatgaaa aggccatcaa catcaccgtg gttgagagcg gctacgtgcg gctcctggga    960
gaggtgggca cactacaatt tgctgagctg catcggagcc ggacactgca ggtagtgttc   1020
gaggcctacc caccgcccac tgtcctgtgg ttcaaagaca accgcaccct gggcgactcc   1080
agcgctggcg aaatcgccct gtccacgcgc aacgtgtcgg agacccggta tgtgtcagag   1140
ctgacactgg ttcgcgtgaa ggtggcagag gctggccact acaccatgcg ggccttccat   1200
gaggatgctg aggtccagct ctccttccag ctacagatca atgtccctgt ccgagtgctg   1260
gagctaagtg agagccaccc tgacagtggg aacagacag tccgctgtcg tggccggggc   1320
atgccccagc cgaacatcat ctggtctgcc tgcagagacc tcaaaaggtg tccacgtgag   1380
ctgccgccca cgctgctggg aacagttcc gaagaggaga gccagctgga gactaacgtg    1440
acgtactggg aggaggagca ggagtttgag gtggtgagca cactgcgtct gcagcacgtg   1500
gatcggccac tgtcggtgcg ctgcacgctg cgcaacgctg tgggccagga cacgcaggag   1560
gtcatcgtgg tgccacactc cttgcccttc aaggaccccg agcccaaatc ttgtgacaaa   1620
actcacacat gcccaccgtg cccagcacct gaactcctgg ggggaccgtc agtcttcctc   1680
ttccccccaa aacccaagga caccctcatg atctcccgga cccctgaggt cacatgcgtg   1740
gtggtggacg tgagccacga agaccctgag gtcaagttca actggtacgt ggacggcgtg   1800
gaggtgcata atgccaagac aaagccgcgg gaggagcagt acaacagcac gtaccgtgtg   1860
gtcagcgtcc tcaccgtcct gcaccaggac tggctgaatg gcaaggagta caagtgcaag   1920
gtctccaaca aagccctccc agcccccatc gagaaaacca tctccaaagc caaagggcag   1980
ccccgagaac cacaggtgta caccctgccc ccatcccggg atgagctgac caagaaccag   2040
gtcagcctga cctgcctggt caaaggcttc tatcccagcg acatcgccgt ggagtgggag   2100
agcaatgggc agccggagaa caactacaag accacgcctc ccgtgctgga ctccgacggc   2160
tccttcttcc tctacagcaa gctcaccgtg gacaagagca ggtggcagca ggggaacgtc   2220
ttctcatgct ccgtgatgca tgaggctctg cacaaccact acacgcagaa gagcctctcc   2280
ctgtctccgg gtaaa                                                    2295
```

<210> SEQ ID NO 26
<211> LENGTH: 765
<212> TYPE: PRT
<213> ORGANISM: Artificial Sequence
<220> FEATURE:
<223> OTHER INFORMATION: 963 molecule amino acid sequence

<400> SEQUENCE: 26

```
Met Arg Leu Pro Gly Ala Met Pro Ala Leu Ala Leu Lys Gly Glu Leu
1               5                   10                  15

Leu Leu Leu Ser Leu Leu Leu Leu Glu Pro Gln Ile Ser Gln Gly
            20                  25                  30

Leu Val Val Thr Pro Pro Gly Pro Glu Leu Val Leu Asn Val Ser Ser
        35                  40                  45

Thr Phe Val Leu Thr Cys Ser Gly Ser Ala Pro Val Val Trp Glu Arg
    50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                85                  90                  95
```

-continued

Glu Tyr Phe Cys Thr His Asn Asp Ser Arg Gly Leu Glu Thr Asp Glu
            100                 105                 110

Arg Lys Arg Leu Tyr Ile Phe Val Pro Asp Pro Thr Val Gly Phe Leu
        115                 120                 125

Pro Asn Asp Ala Glu Glu Leu Phe Ile Phe Leu Thr Glu Ile Thr Glu
    130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
                165                 170                 175

Arg Gly Phe Ser Gly Ile Phe Glu Asp Arg Ser Tyr Ile Cys Lys Thr
            180                 185                 190

Thr Ile Gly Asp Arg Glu Val Asp Ser Asp Ala Tyr Tyr Val Tyr Arg
        195                 200                 205

Leu Gln Val Ser Ser Ile Asn Val Ser Val Asn Ala Val Gln Thr Val
    210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
                245                 250                 255

Leu Val Glu Pro Val Thr Asp Phe Leu Leu Asp Met Pro Tyr His Ile
            260                 265                 270

Arg Ser Ile Leu His Ile Pro Ser Ala Glu Leu Glu Asp Ser Gly Thr
        275                 280                 285

Tyr Thr Cys Asn Val Thr Glu Ser Val Asn Asp His Gln Asp Glu Lys
    290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
                325                 330                 335

Gln Val Val Phe Glu Ala Tyr Pro Pro Pro Thr Val Leu Trp Phe Lys
            340                 345                 350

Asp Asn Arg Thr Leu Gly Asp Ser Ser Ala Gly Glu Ile Ala Leu Ser
        355                 360                 365

Thr Arg Asn Val Ser Glu Thr Arg Tyr Val Ser Glu Leu Thr Leu Val
    370                 375                 380

Arg Val Lys Val Ala Glu Ala Gly His Tyr Thr Met Arg Ala Phe His
385                 390                 395                 400

Glu Asp Ala Glu Val Gln Leu Ser Phe Gln Leu Gln Ile Asn Val Pro
                405                 410                 415

Val Arg Val Leu Glu Leu Ser Glu Ser His Pro Asp Ser Gly Glu Gln
            420                 425                 430

Thr Val Arg Cys Arg Gly Arg Gly Met Pro Gln Pro Asn Ile Ile Trp
        435                 440                 445

Ser Ala Cys Arg Asp Leu Lys Arg Cys Pro Arg Glu Leu Pro Pro Thr
    450                 455                 460

Leu Leu Gly Asn Ser Ser Glu Glu Glu Ser Gln Leu Glu Thr Asn Val
465                 470                 475                 480

Thr Tyr Trp Glu Glu Glu Gln Glu Phe Glu Val Val Ser Thr Leu Arg
                485                 490                 495

Leu Gln His Val Asp Arg Pro Leu Ser Val Arg Cys Thr Leu Arg Asn
            500                 505                 510

Ala Val Gly Gln Asp Thr Gln Glu Val Ile Val Val Pro His Ser Leu

```
                515                 520                 525
Pro Phe Lys Asp Pro Glu Pro Lys Ser Cys Asp Lys Thr His Thr Cys
            530                 535                 540

Pro Pro Cys Pro Ala Pro Glu Leu Leu Gly Gly Pro Ser Val Phe Leu
545                 550                 555                 560

Phe Pro Pro Lys Pro Lys Asp Thr Leu Met Ile Ser Arg Thr Pro Glu
                565                 570                 575

Val Thr Cys Val Val Val Asp Val Ser His Glu Asp Pro Glu Val Lys
            580                 585                 590

Phe Asn Trp Tyr Val Asp Gly Val Glu Val His Asn Ala Lys Thr Lys
        595                 600                 605

Pro Arg Glu Glu Gln Tyr Asn Ser Thr Tyr Arg Val Val Ser Val Leu
    610                 615                 620

Thr Val Leu His Gln Asp Trp Leu Asn Gly Lys Glu Tyr Lys Cys Lys
625                 630                 635                 640

Val Ser Asn Lys Ala Leu Pro Ala Pro Ile Glu Lys Thr Ile Ser Lys
                645                 650                 655

Ala Lys Gly Gln Pro Arg Glu Pro Gln Val Tyr Thr Leu Pro Pro Ser
            660                 665                 670

Arg Asp Glu Leu Thr Lys Asn Gln Val Ser Leu Thr Cys Leu Val Lys
        675                 680                 685

Gly Phe Tyr Pro Ser Asp Ile Ala Val Glu Trp Glu Ser Asn Gly Gln
    690                 695                 700

Pro Glu Asn Asn Tyr Lys Thr Thr Pro Pro Val Leu Asp Ser Asp Gly
705                 710                 715                 720

Ser Phe Phe Leu Tyr Ser Lys Leu Thr Val Asp Lys Ser Arg Trp Gln
                725                 730                 735

Gln Gly Asn Val Phe Ser Cys Ser Val Met His Glu Ala Leu His Asn
            740                 745                 750

His Tyr Thr Gln Lys Ser Leu Ser Leu Ser Pro Gly Lys
        755                 760                 765

<210> SEQ ID NO 27
<211> LENGTH: 1656
<212> TYPE: DNA
<213> ORGANISM: Artificial Sequence
<220> FEATURE:
<223> OTHER INFORMATION: 974 molecule nucleic acid sequence

<400> SEQUENCE: 27
atgcggcttc cgggtgcgat gccagctctg gccctcaaag gcgagctgct gttgctgtct      60
ctcctgttac ttctggaacc acagatctct cagggcctgg tcgtcacacc cccggggcca     120
gagcttgtcc tcaatgtctc cagcaccttc gttctgacct gctcgggttc agctccggtg     180
gtgtgggaac ggatgtccca ggagccccca caggaaatgg ccaaggccca ggatggcacc     240
ttctccagcg tgctcacact gaccaacctc actgggctag acacgggaga atacttttgc     300
acccacaatg actcccgtgg actggagacc gatgagcgga acggctcta catctttgtg      360 ccagatccca ccgtgggctt cctccctaat gatgccgagg aactattcat ctttctcacg     420
gaaataactg agatcaccat tccatgccga gtaacagacc acagctggt ggtgacactg      480 cacgagaaga aggggacgt tgcactgcct gtccctatg atcaccaacg tggctttct       540 ggtatctttg aggacagaag ctacatctgc aaaaccacca ttggggacag ggaggtggat     600
tctgatgcct actatgtcta cagactccag gtgtcatcca tcaacgtctc tgtgaacgca     660
```

```
gtgcagactg tggtccgcca gggtgagaac atcaccctca tgtgcattgt gatcgggaat    720
gaggtggtca acttcgagtg gacatacccc cgcaaagaaa gtgggcggct ggtggagccg    780
gtgactgact tcctcttgga tatgccttac cacatccgct ccatcctgca catccccagt    840
gccgagttag aagactcggg gacctacacc tgcaatgtga cggagagtgt gaatgaccat    900
caggatgaaa aggccatcaa catcaccgtg gttgagagcg gctacgtgcg gctcctggga    960
gagcccaaat cttgtgacaa aactcacaca tgcccaccgt gcccagcacc tgaactcctg   1020
gggggaccgt cagtcttcct cttcccccca aaacccaagg acaccctcat gatctcccgg   1080
acccctgagg tcacatgcgt ggtggtggac gtgagccacg aagaccctga ggtcaagttc   1140
aactggtacg tggacggcgt ggaggtgcat aatgccaaga caaagccgcg ggaggagcag   1200
tacaacagca cgtaccgtgt ggtcagcgtc ctcaccgtcc tgcaccagga ctggctgaat   1260
ggcaaggagt acaagtgcaa ggtctccaac aaagccctcc cagcccccat cgagaaaacc   1320
atctccaaag ccaaagggca gccccgagaa ccacaggtgt acaccctgcc cccatcccgg   1380
gatgagctga ccaagaacca ggtcagcctg acctgcctgg tcaaaggctt ctatcccagc   1440
gacatcgccg tggagtggga gagcaatggg cagccggaga acaactacaa gaccacgcct   1500
cccgtgctgg actccgacgg ctccttcttc ctctacagca agctcaccgt ggacaagagc   1560
aggtggcagc aggggaacgt cttctcatgc tccgtgatgc atgaggctct gcacaaccac   1620
tacacgcaga agagcctctc cctgtctccg ggtaaa                             1656
```

<210> SEQ ID NO 28  
<211> LENGTH: 552  
<212> TYPE: PRT  
<213> ORGANISM: Artificial Sequence  
<220> FEATURE:  
<223> OTHER INFORMATION: 974 molecule amino acid sequence

<400> SEQUENCE: 28

```
Met Arg Leu Pro Gly Ala Met Pro Ala Leu Ala Leu Lys Gly Glu Leu
1               5                   10                  15

Leu Leu Leu Ser Leu Leu Leu Leu Glu Pro Gln Ile Ser Gln Gly
            20                  25                  30

Leu Val Val Thr Pro Pro Gly Pro Glu Leu Val Leu Asn Val Ser Ser
        35                  40                  45

Thr Phe Val Leu Thr Cys Ser Gly Ser Ala Pro Val Val Trp Glu Arg
    50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                85                  90                  95

Glu Tyr Phe Cys Thr His Asn Asp Ser Arg Gly Leu Glu Thr Asp Glu
            100                 105                 110

Arg Lys Arg Leu Tyr Ile Phe Val Pro Asp Pro Thr Val Gly Phe Leu
        115                 120                 125

Pro Asn Asp Ala Glu Glu Leu Phe Ile Phe Leu Thr Glu Ile Thr Glu
    130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
                165                 170                 175

Arg Gly Phe Ser Gly Ile Phe Glu Asp Arg Ser Tyr Ile Cys Lys Thr
            180                 185                 190
```

Thr Ile Gly Asp Arg Glu Val Asp Ser Asp Ala Tyr Tyr Val Tyr Arg
        195                 200                 205

Leu Gln Val Ser Ser Ile Asn Val Ser Val Asn Ala Val Gln Thr Val
    210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
                245                 250                 255

Leu Val Glu Pro Val Thr Asp Phe Leu Leu Asp Met Pro Tyr His Ile
            260                 265                 270

Arg Ser Ile Leu His Ile Pro Ser Ala Glu Leu Glu Asp Ser Gly Thr
        275                 280                 285

Tyr Thr Cys Asn Val Thr Glu Ser Val Asn Asp His Gln Asp Glu Lys
    290                 295                 300

Ala Ile Asn Ile Thr Val Val Glu Ser Gly Tyr Val Arg Leu Leu Gly
305                 310                 315                 320

Glu Pro Lys Ser Cys Asp Lys Thr His Thr Cys Pro Pro Cys Pro Ala
                325                 330                 335

Pro Glu Leu Leu Gly Gly Pro Ser Val Phe Leu Phe Pro Pro Lys Pro
            340                 345                 350

Lys Asp Thr Leu Met Ile Ser Arg Thr Pro Glu Val Thr Cys Val Val
        355                 360                 365

Val Asp Val Ser His Glu Asp Pro Glu Val Lys Phe Asn Trp Tyr Val
    370                 375                 380

Asp Gly Val Glu Val His Asn Ala Lys Thr Lys Pro Arg Glu Glu Gln
385                 390                 395                 400

Tyr Asn Ser Thr Tyr Arg Val Val Ser Val Leu Thr Val Leu His Gln
                405                 410                 415

Asp Trp Leu Asn Gly Lys Glu Tyr Lys Cys Lys Val Ser Asn Lys Ala
            420                 425                 430

Leu Pro Ala Pro Ile Glu Lys Thr Ile Ser Lys Ala Lys Gly Gln Pro
        435                 440                 445

Arg Glu Pro Gln Val Tyr Thr Leu Pro Pro Ser Arg Asp Glu Leu Thr
    450                 455                 460

Lys Asn Gln Val Ser Leu Thr Cys Leu Val Lys Gly Phe Tyr Pro Ser
465                 470                 475                 480

Asp Ile Ala Val Glu Trp Glu Ser Asn Gly Gln Pro Glu Asn Asn Tyr
                485                 490                 495

Lys Thr Thr Pro Pro Val Leu Asp Ser Asp Gly Ser Phe Phe Leu Tyr
            500                 505                 510

Ser Lys Leu Thr Val Asp Lys Ser Arg Trp Gln Gln Gly Asn Val Phe
        515                 520                 525

Ser Cys Ser Val Met His Glu Ala Leu His Asn His Tyr Thr Gln Lys
    530                 535                 540

Ser Leu Ser Leu Ser Pro Gly Lys
545                 550

<210> SEQ ID NO 29
<211> LENGTH: 1593
<212> TYPE: DNA
<213> ORGANISM: Artificial Sequence
<220> FEATURE:
<223> OTHER INFORMATION: 978 molecule nucleic acid sequence

<400> SEQUENCE: 29

```
atgcggcttc cgggtgcgat gccagctctg gccctcaaag gcgagctgct gttgctgtct      60
ctcctgttac ttctggaacc acagatctct cagggcctgg tcgtcacacc cccggggcca     120
gagcttgtcc tcaatgtctc cagcaccttc gttctgacct gctcgggttc agctccggtg     180
gtgtgggaac ggatgtccca ggagccccca caggaaatgg ccaaggccca ggatggcacc     240
ttctccagcg tgctcacact gaccaacctc actgggctag acacgggaga atactttgc      300
acccacaatg actcccgtgg actggagacc gatgagcgga acggctcta catctttgtg      360
ccagatccca ccgtgggctt cctccctaat gatgccgagg aactattcat ctttctcacg     420
gaaataactg agatcaccat tccatgccga gtaacagacc cacagctggt ggtgacactg     480
cacgagaaga aggggacgt tgcactgcct gtccctatg atcaccaacg tggcttttct       540
ggtatctttg aggacagaag ctacatctgc aaaaccacca ttggggacag ggaggtggat     600
tctgatgcct actatgtcta cagactccag gtgtcatcca tcaacgtctc tgtgaacgca     660
gtgcagactg tggccgcca gggtgagaac atcaccctca tgtgcattgt gatcgggaat     720
gaggtggtca acttcgagtg gacatacccc cgcaaagaaa gtgggcggct ggtggagccg     780
gtgactgact cctcttgga tatgccttac acatccgct ccatcctgca catccccagt       840
gccgagttag aagactcggg gacctacacc tgcaatgtga cggagagtgt gaatgaccat     900
caggatgaaa aggccatcaa catcaccgtg gttgagagcg gctacgtgcg gctcctggga     960
gaggtgggca cactacaatt tgctgagctg catcggagcc ggacactgca ggtagtgttc    1020
gaggcctacc caccgcccac tgtcctgtgg ttcaaagaca accgcaccct gggcgactcc    1080
agcgctggcg aaatcgccct gtccacgcgc aacgtgtcgg agacccggta tgtgtcagag    1140
ctgacactgg ttcgcgtgaa ggtggcagag gctggccact acaccatgcg ggccttccat    1200
gaggatgctg aggtccagct ctccttccag ctacagatca atgtccctgt ccgagtgctg    1260
gagctaagtg agagccaccc tgacagtggg aacagacag tccgctgtcg tggccggggc     1320
atgccccagc cgaacatcat ctggtctgcc tgcagagacc tcaaaaggtg tccacgtgag    1380
ctgccgccca cgctgctggg aacagttcc gaagaggaga gccagctgga gactaacgtg     1440
acgtactggg aggaggagca ggagtttgag gtggtgagca cactgcgtct gcagcacgtg    1500
gatcggccac tgtcggtgcg ctgcacgctg cgcaacgctg tgggccagga cacgcaggag    1560
gtcatcgtgg tgccacactc cttgcccttc aag                                 1593
```

<210> SEQ ID NO 30
<211> LENGTH: 531
<212> TYPE: PRT
<213> ORGANISM: Artificial Sequence
<220> FEATURE:
<223> OTHER INFORMATION: 978 molecule amino acid sequence

<400> SEQUENCE: 30

Met Arg Leu Pro Gly Ala Met Pro Ala Leu Ala Leu Lys Gly Glu Leu
1               5                   10                  15

Leu Leu Leu Ser Leu Leu Leu Leu Glu Pro Gln Ile Ser Gln Gly
                20                  25                  30

Leu Val Val Thr Pro Pro Gly Pro Glu Leu Val Leu Asn Val Ser Ser
            35                  40                  45

Thr Phe Val Leu Thr Cys Ser Gly Ser Ala Pro Val Val Trp Glu Arg
        50                  55                  60

Met Ser Gln Glu Pro Pro Gln Glu Met Ala Lys Ala Gln Asp Gly Thr
65                  70                  75                  80

```
Phe Ser Ser Val Leu Thr Leu Thr Asn Leu Thr Gly Leu Asp Thr Gly
                85                  90                  95
Glu Tyr Phe Cys Thr His Asn Asp Ser Arg Gly Leu Glu Thr Asp Glu
            100                 105                 110
Arg Lys Arg Leu Tyr Ile Phe Val Pro Asp Pro Thr Val Gly Phe Leu
        115                 120                 125
Pro Asn Asp Ala Glu Glu Leu Phe Ile Phe Leu Thr Glu Ile Thr Glu
130                 135                 140
Ile Thr Ile Pro Cys Arg Val Thr Asp Pro Gln Leu Val Val Thr Leu
145                 150                 155                 160
His Glu Lys Lys Gly Asp Val Ala Leu Pro Val Pro Tyr Asp His Gln
                165                 170                 175
Arg Gly Phe Ser Gly Ile Phe Glu Asp Arg Ser Tyr Ile Cys Lys Thr
            180                 185                 190
Thr Ile Gly Asp Arg Glu Val Asp Ser Asp Ala Tyr Tyr Val Tyr Arg
        195                 200                 205
Leu Gln Val Ser Ser Ile Asn Val Ser Val Asn Ala Val Gln Thr Val
210                 215                 220
Val Arg Gln Gly Glu Asn Ile Thr Leu Met Cys Ile Val Ile Gly Asn
225                 230                 235                 240
Glu Val Val Asn Phe Glu Trp Thr Tyr Pro Arg Lys Glu Ser Gly Arg
                245                 250                 255
Leu Val Glu Pro Val Thr Asp Phe Leu Leu Asp Met Pro Tyr His Ile
            260                 265                 270
Arg Ser Ile Leu His Ile Pro Ser Ala Glu Leu Glu Asp Ser Gly Thr
        275                 280                 285
Tyr Thr Cys Asn Val Thr Glu Ser Val Asn Asp His Gln Asp Glu Lys
290                 295                 300
Ala Ile Asn Ile Thr Val Val Glu Ser Gly Tyr Val Arg Leu Leu Gly
305                 310                 315                 320
Glu Val Gly Thr Leu Gln Phe Ala Glu Leu His Arg Ser Arg Thr Leu
                325                 330                 335
Gln Val Val Phe Glu Ala Tyr Pro Pro Pro Thr Val Leu Trp Phe Lys
            340                 345                 350
Asp Asn Arg Thr Leu Gly Asp Ser Ser Ala Gly Glu Ile Ala Leu Ser
        355                 360                 365
Thr Arg Asn Val Ser Glu Thr Arg Tyr Val Ser Glu Leu Thr Leu Val
370                 375                 380
Arg Val Lys Val Ala Glu Ala Gly His Tyr Thr Met Arg Ala Phe His
385                 390                 395                 400
Glu Asp Ala Glu Val Gln Leu Ser Phe Gln Leu Gln Ile Asn Val Pro
                405                 410                 415
Val Arg Val Leu Glu Leu Ser Glu Ser His Pro Asp Ser Gly Glu Gln
            420                 425                 430
Thr Val Arg Cys Arg Gly Arg Gly Met Pro Gln Pro Asn Ile Ile Trp
        435                 440                 445
Ser Ala Cys Arg Asp Leu Lys Arg Cys Pro Arg Glu Leu Pro Pro Thr
450                 455                 460
Leu Leu Gly Asn Ser Ser Glu Glu Ser Gln Leu Glu Thr Asn Val
465                 470                 475                 480
Thr Tyr Trp Glu Glu Glu Gln Glu Phe Glu Val Val Ser Thr Leu Arg
                485                 490                 495
```

```
Leu Gln His Val Asp Arg Pro Leu Ser Val Arg Cys Thr Leu Arg Asn
            500                 505                 510
Ala Val Gly Gln Asp Thr Gln Glu Val Ile Val Pro His Ser Leu
        515                 520                 525
Pro Phe Lys
    530

<210> SEQ ID NO 31
<211> LENGTH: 1737
<212> TYPE: DNA
<213> ORGANISM: Artificial Sequence
<220> FEATURE:
<223> OTHER INFORMATION: 977 molecule nucleic acid sequence

<400> SEQUENCE: 31
atggggcagt gcaggaaaag tggcactatg aaccctgcag ccctagacaa ttgtactaac      60
cttcttctct ttcctctcct gacaggttgg tgtacagtag cttccaagta ctccaccatg     120
cggcttccgg gtgcgatgcc agctctggcc ctcaaaggcg agctgctgtt gctgtctctc     180
ctgttacttc tggaaccaca gatctctcag ggcctggtcg tcacaccccc ggggccagag     240
cttgtcctca atgtctccag caccttcgtt ctgacctgct cgggttcagc tccggtggtg     300
tgggaacgga tgtcccagga gcccccacag gaaatggcca aggcccagga tggcaccttc     360
tccagcgtgc tcacactgac caacctcact gggctagaca cggagaata cttttgcacc     420 cacaatgact cccgtggact ggagaccgat gagcggaaac ggctctacat ctttgtgcca     480
gatcccaccg tgggcttcct ccctaatgat gccgaggaac tattcatctt tctcacggaa     540
ataactgaga tcaccattcc atgccgagta acagacccac agctggtggt gacactgcac     600
gagaagaaag gggacgttgc actgcctgtc ccctatgatc accaacgtgg cttttctggt     660
atctttgagg acagaagcta catctgcaaa accaccattg gggacaggga ggtggattct     720
gatgcctact atgtctacag actccaggtg tcatccatca acgtctctgt gaacgcagtg     780
cagactgtgg tccgccaggg tgagaacatc accctcatgt gcattgtgat cgggaatgag     840
gtggtcaact tcgagtggac ataccccgc aaagaaagtg ggcggctggt ggagccggtg     900
actgacttcc tcttggatat gccttaccac atccgctcca tcctgcacat ccccagtgcc     960
gagttagaag actcggggac ctacacctgc aatgtgacgg agagtgtgaa tgaccatcag    1020
gatgaaaagg ccatcaacat caccgtggtt gagagcggct acgtgcggct cctgggagag    1080
gtgggcacac tacaatttgc tgagctgcat cggagccgga cactgcaggt agtgttcgag    1140
gcctacccac cgcccactgt cctgtggttc aaagacaacc gcaccctggg cgactccagc    1200
gctggcgaaa tcgccctgtc cacgcgcaac gtgtcggaga cccggtatgt gtcagagctg    1260
acactggttc gcgtgaaggt ggcagaggct ggccactaca ccatgcgggc cttccatgag    1320
gatgctgagg tccagctctc cttccagcta cagatcaatg tccctgtccg agtgctggag    1380
ctaagtgaga gccaccctga cagtgggaa cagacagtcc gctgtcgtgg ccggggcatg    1440
ccccagccga acatcatctg gtctgcctgc agagacctca aaggtgtcc acgtgagctg    1500 ccgcccacgc tgctggggaa cagttccgaa gaggagagcc agctggagac taacgtgacg    1560
tactgggagg aggagcagga gtttgaggtg gtgagcacac tgcgtctgca gcacgtggat    1620
cggccactgt cggtgcgctg cacgctgcgc aacgctgtgg ccaggacac gcaggaggtc    1680 atcgtggtgc acactctttt gcccttcaag cggggcagcc accaccacca ccaccac    1737

<210> SEQ ID NO 32
```

<211> LENGTH: 579
<212> TYPE: PRT
<213> ORGANISM: Artificial Sequence
<220> FEATURE:
<223> OTHER INFORMATION: 977 molecule amino acid sequence

<400> SEQUENCE: 32

Met Gly Gln Cys Arg Lys Ser Gly Thr Met Asn Pro Ala Ala Leu Asp
1               5                   10                  15

Asn Cys Thr Asn Leu Leu Leu Phe Pro Leu Leu Thr Gly Trp Cys Thr
            20                  25                  30

Val Ala Ser Lys Tyr Ser Thr Met Arg Leu Pro Gly Ala Met Pro Ala
        35                  40                  45

Leu Ala Leu Lys Gly Glu Leu Leu Leu Ser Leu Leu Leu Leu Leu
    50                  55                  60

Glu Pro Gln Ile Ser Gln Gly Leu Val Val Thr Pro Pro Gly Pro Glu
65                  70                  75                  80

Leu Val Leu Asn Val Ser Ser Thr Phe Val Leu Thr Cys Ser Gly Ser
                85                  90                  95

Ala Pro Val Val Trp Glu Arg Met Ser Gln Glu Pro Pro Gln Glu Met
            100                 105                 110

Ala Lys Ala Gln Asp Gly Thr Phe Ser Ser Val Leu Thr Leu Thr Asn
        115                 120                 125

Leu Thr Gly Leu Asp Thr Gly Glu Tyr Phe Cys Thr His Asn Asp Ser
    130                 135                 140

Arg Gly Leu Glu Thr Asp Glu Arg Lys Arg Leu Tyr Ile Phe Val Pro
145                 150                 155                 160

Asp Pro Thr Val Gly Phe Leu Pro Asn Asp Ala Glu Glu Leu Phe Ile
                165                 170                 175

Phe Leu Thr Glu Ile Thr Glu Ile Thr Ile Pro Cys Arg Val Thr Asp
            180                 185                 190

Pro Gln Leu Val Val Thr Leu His Glu Lys Lys Gly Asp Val Ala Leu
        195                 200                 205

Pro Val Pro Tyr Asp His Gln Arg Gly Phe Ser Gly Ile Phe Glu Asp
    210                 215                 220

Arg Ser Tyr Ile Cys Lys Thr Thr Ile Gly Asp Arg Glu Val Asp Ser
225                 230                 235                 240

Asp Ala Tyr Tyr Val Tyr Arg Leu Gln Val Ser Ser Ile Asn Val Ser
                245                 250                 255

Val Asn Ala Val Gln Thr Val Val Arg Gln Gly Glu Asn Ile Thr Leu
            260                 265                 270

Met Cys Ile Val Ile Gly Asn Glu Val Val Asn Phe Glu Trp Thr Tyr
        275                 280                 285

Pro Arg Lys Glu Ser Gly Arg Leu Val Glu Pro Val Thr Asp Phe Leu
    290                 295                 300

Leu Asp Met Pro Tyr His Ile Arg Ser Ile Leu His Ile Pro Ser Ala
305                 310                 315                 320

Glu Leu Glu Asp Ser Gly Thr Tyr Thr Cys Asn Val Thr Glu Ser Val
                325                 330                 335

Asn Asp His Gln Asp Glu Lys Ala Ile Asn Ile Thr Val Val Glu Ser
            340                 345                 350

Gly Tyr Val Arg Leu Leu Gly Glu Val Gly Thr Leu Gln Phe Ala Glu
        355                 360                 365

Leu His Arg Ser Arg Thr Leu Gln Val Val Phe Glu Ala Tyr Pro Pro
    370                 375                 380

-continued

```
Pro Thr Val Leu Trp Phe Lys Asp Asn Arg Thr Leu Gly Asp Ser Ser
385                 390                 395                 400

Ala Gly Glu Ile Ala Leu Ser Thr Arg Asn Val Ser Glu Thr Arg Tyr
            405                 410                 415

Val Ser Glu Leu Thr Leu Val Arg Val Lys Val Ala Glu Ala Gly His
        420                 425                 430

Tyr Thr Met Arg Ala Phe His Glu Asp Ala Glu Val Gln Leu Ser Phe
        435                 440                 445

Gln Leu Gln Ile Asn Val Pro Val Arg Val Leu Glu Leu Ser Glu Ser
    450                 455                 460

His Pro Asp Ser Gly Glu Gln Thr Val Arg Cys Arg Gly Arg Gly Met
465                 470                 475                 480

Pro Gln Pro Asn Ile Ile Trp Ser Ala Cys Arg Asp Leu Lys Arg Cys
            485                 490                 495

Pro Arg Glu Leu Pro Pro Thr Leu Leu Gly Asn Ser Ser Glu Glu Glu
            500                 505                 510

Ser Gln Leu Glu Thr Asn Val Thr Tyr Trp Glu Glu Glu Gln Glu Phe
        515                 520                 525

Glu Val Val Ser Thr Leu Arg Leu Gln His Val Asp Arg Pro Leu Ser
        530                 535                 540

Val Arg Cys Thr Leu Arg Asn Ala Val Gly Gln Asp Thr Gln Glu Val
545                 550                 555                 560

Ile Val Val Pro His Ser Leu Pro Phe Lys Arg Gly Ser His His His
                565                 570                 575

His His His
```

ENCAPSULATED CELL THERAPY CARTRIDGE

RELATED APPLICATIONS

This application claims priority to U.S. Provisional Patent Application No. 61/876,638, filed on Sep. 11, 2013, the contents of which are herein incorporated by reference in its entirety.

INCORPORATION BY REFERENCE OF SEQUENCE LISTING

The contents of the text file named "NETE-062_001US_ST25.txt", which was created on Sep. 10, 2014 and is 96,100 bytes in size, are hereby incorporated by reference in their entireties.

FIELD OF THE INVENTION

The present invention relates generally to the field of encapsulated cell therapy.

BACKGROUND OF THE INVENTION

Encapsulated cell technology or ECT is a delivery system that uses live cells to secret a therapeutic agent. This is usually achieved by genetically engineering a specific type of cell to overexpress a particular agent. The engineered cells are then encapsulated in semi-permeable polymer capsules. The capsule is then implanted into the target surgical site. The semi-permeable membrane allows the free diffusion of nutrients and therapeutic molecules yet prevents the direct contact of the host immune systems cells with the cells within the device. However, current encapsulated cell delivery devices used in treatment of retinitis pigmentosa or geographic atrophy are limited in their capability to achieve microgram production levels of encapsulated cell produced protein drug.

Therefore, there is a need for an encapsulated implant design capable of allowing increased cell encapsulation volumes while maintaining cell viability and maximizing protein drug production.

SUMMARY OF THE INVENTION

Provided herein are multi-chamber implantable cell culture devices containing two or more individual chambers for the delivery of a biologically active molecule to a specific target region. For example, the biologically active molecule can be produced by a cell line containing one or more genetically engineered cells (e.g., ARPE-19 cells).

Cell lines (such as, but not limited to, ARPE-19 cells) can be genetically engineered to produce a therapeutic amount of one or more biologically active molecules. For example, the one or more biologically active molecule(s) can include anti-angiogenic antibodies and molecules, anti-angiogenic antibody scaffolds, soluble receptors, agents targeting and inhibiting or modulating immunologic pathway molecules, growth factor inhibitors, growth factors, neurotrophic factors, angiogenic factors, neurotransmitters, hormones, enzymes, anti-inflammatory factors, therapeutic proteins, gene transfer vectors, antibodies and antibody fragments, antigens, or any combination thereof.

In various embodiments, such molecules can include, but are not limited to, C3a inhibitors, C3b inhibitors, other agents targeting and inhibiting or modulating immunologic pathway molecules, brain derived neurotrophic factor (BDNF), NT-4, ciliary neurotrophic factor (CNTF), Axokine, basic fibroblast growth factor (bFGF), insulin-like growth factor I (IGF I), insulin-like growth factor II (IGF II), acid fibroblast growth factor (aFGF), epidermal growth factor (EGF), transforming growth factor α (TGF α), transforming growth factor β (TGF β), nerve growth factor (NGF), platelet derived growth factor (PDGF), glia-derived neurotrophic factor (GDNF), Midkine, phorbol 12-myristate 13-acetate, tryophotin, activin, thyrotropin releasing hormone, interleukins, bone morphogenic protein, macrophage inflammatory proteins, heparin sulfate, amphiregulin, retinoic acid, tumor necrosis factor α, fibroblast growth factor receptor, epidermal growth factor receptor (EGFR), PEDF, LEDGF, NTN, Neublastin, neurotrophins, lymphokines, VEGF inhibitors, PDGF inhibitors, placental growth factor (PlGF) inhibitors, Tie2, CD55, C59, a bispecific molecule that simultaneously binds VEGF and PDGF, and other agents expected to have therapeutically useful effects on potential target tissues. Such cell lines can be encapsulated in encapsulation cell therapy (ECT) devices using any method(s) known in the art.

Described herein are implantable cell culture devices containing two or more (i.e., 2, 3, 4, 5, 6, 7, 8, 9, 10, 11, 12, 13, 14, 15, 16, 17, 18, 19, 20, or more) individual chambers. Each individual chamber contains a core that contains a therapeutically effective amount of one or more biologically active molecules and a semi-permeable membrane surrounding the core, wherein the membrane permits the diffusion of biologically active molecule(s) there through it.

For example, the one or more biologically active molecules in the core of each chamber can be produced by one or more genetically engineered cell lines contained within the core(s) of the individual chambers of the device. For example, the one or more cell lines contain one or more genetically engineered ARPE-19 cells that are contained within the cores of the individual chambers.

For example, the one or more biologically active molecules can be introduced into the one or more genetically engineered cell lines (for example, ARPE-19 cells) by an iterative transfection process, wherein the iterative transfection process comprises one, two, three or more transfections (e.g., 1, 2, 3, 4, 5, 6, 7, 8, 9, 10, or more transfections). Those skilled in the art will recognize that the number of transfections in the iterative transfection process will determine the number of the (same or different) biologically active molecule(s) produced by the resulting cell line. The iterative transfection process can be used to introduce multiple copies of the same or different biologically active molecule(s) into the cells (e.g., ARPE-19 cells).

In some embodiments, the device is cryopreserved. The core of each chamber within such cryopreserved devices may also contain a cryoprotectant agent, which can be added to the cell culture media contained within the core.

Any cryopreservation method(s) known in the art can be employed. By way of non-limiting example, encapsulated cell therapy devices can be placed in cryogenic storage vials, frozen under controlled rate freezing (e.g., to a temperature of −80° C.), and finally stored in vapor phase liquid nitrogen (e.g., −190° C.) conditions.

Cryopreserved devices can be transported under vapor phase liquid nitrogen (e.g., −190° C.) conditions and/or under dry ice (e.g., −70° C.) conditions.

Cryopreserved devices can be thawed using any method(s) known in the art prior to use.

In some embodiments, the device contains 2-20 (e.g., 2, 3, 4, 5, 6, 7, 8, 9, 10, 11, 12, 13, 14, 15, 16, 17, 18, 19 or 20)

individual chambers. The inner diameter of each chamber can be between 100 microns and 900 microns (e.g., 100, 200, 300, 400, 500, 600, 700, 800 or 900 μm) and bundled in numbers between 2 and 20 chambers (e.g., 2, 3, 4, 5, 6, 7, 8, 9, 10, 11, 12, 13, 14, 15, 16, 17, 18, 19, or 20). The wall thicknesses of each chamber should be manufactured to create the minimal diffusion distance yet achieve adequate column strength. The nominal ratio of inner diameter to wall thickness of each chamber is about 5:1 to 20:1 in scale. For example, the ratio is 5:1, 6:1, 7:1, 8:1, 9:1, 10:1, 11:1, 12:1, 13:1, 14:1, 15:1, 16:1, 17:1, 18:1, 19:1, or 20:1 in scale. For example, the ratio is 10:1 in scale.

The overall size of the device will vary depending upon the number and size of the individual chambers used in the assembly. For example, the range of diameter of the device is between 0.5 mm and 5.0 mm (e.g., 0.5, 1.0, 1.5, 2.0, 2.5, 3.0, 3.5, 4.0, 4.5 or 5.0 mm) with lengths varying from a minimum of 0.4 mm to a maximum of 11 mm (e.g., 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5 or 11 mm). For example, the internal volume of the device is between 2 microliters and 100 microliters (e.g., 2, 3, 4, 5, 6, 7, 8, 9, 10, 15, 20, 25, 30, 35, 40, 45, 50, 55, 60, 65, 70, 75, 80, 85, 90, 95 or 100 μl).

The device may contain one or more (e.g., 1, 2, 3, 4, 5, 6, 7, 8, 9, 10, 11, 12, 13, 14, 15, 16, 17, 18, 19, 20 or more) access ports.

In some embodiments, the core of each chamber contains between $1.0 \times 10^4$ cells and $7.5 \times 10^5$ cells (e.g., $1.0 \times 10^4$, $5.0 \times 10^4$, $1.0 \times 10^5$, $3.0 \times 10^5$, $5.0 \times 10^5$ or $7.5 \times 10^5$ cells). Those skilled in the art will recognize that the exact cell number in each chamber can depend both upon the growth rate of the cell/cell line encapsulated and/or the volume of the individual chambers used to construct the device.

The core of each chamber may additionally contain a matrix disposed within the semi-permeable membrane. In some embodiments, the matrix includes a plurality of monofilaments, wherein the monofilaments are twisted into a yarn or woven into a mesh or are twisted into a yarn that is in non-woven strands, and wherein the cells or tissue are distributed thereon. Those skilled in the art will recognize that the monofilaments can be made from a biocompatible material selected from acrylic, polyester, polyethylene, polypropylene polyacetonitrile, polyethylene terephthalate, nylon, polyamides, polyurethanes, polybutester, silk, cotton, chitin, carbon, and/or biocompatible metals. For example, the monofilaments are polyethylene terephthalate (PET) fibers that comprises between 1-85% (e.g., 1%, 5%, 10%, 15%, 20%, 25%, 30%, 35%, 40%, 45%, 50%, 55%, 60%, 65%, 70%, 75%, 80% or 85%) of the internal volume of each chamber of the device.

The cell encapsulation devices described herein can also have a tether anchor. For example, the tether anchor may be an anchor loop that is adapted for anchoring the device to a structure within a target region (such as an ocular structure).

Any of the devices described herein can be implanted into (or are for implantation in) the eye or another target region of the body, such as, for example, the spleen, ear, heart, colon, liver, kidney, breast, joint, bone marrow, subcutaneous, and/or peritoneal spaces. By way of non-limiting example, the devices can be implanted into (or are for implantation in) the vitreous, the aqueous humor, the Subtenon's space, the periocular space, the posterior chamber, and/or the anterior chamber of the eye.

In some illustrative embodiments, the semi-permeable membranes in the core of each chamber of the devices described herein are made from a permselective, immunoisolatory membrane. For example, the semi-permeable membranes are made from an ultrafiltration membrane or a microfiltration membrane. Those skilled in the art will recognize that an ultrafiltration membrane typically has a pore size of 1-100 nm, whereas a microfiltration membrane typically has a pore size of 0.1-10 μm. In other embodiments, the semi-permeable membranes may be formed into a porous structure. Those skilled in the art will recognize that a semi-permeable membrane typically has a median pore size of about 1-500 nm (e.g., 1, 5, 10, 20, 50, 100, 150, 200, 250, 300, 350, 400, 450 or 500 nm).

In still other embodiments, the semi-permeable membrane may be made from any biocompatible material selected from the group consisting of polyacrylates (including acrylic copolymers), polyvinylidenes, polyvinyl chloride copolymers, polyurethanes, polystyrenes, polyamides, cellulose acetates, cellulose nitrates, polysulfones (including polyether sulfones), polyphosphazenes, polyacrylonitriles, poly(acrylonitrile/covinyl chloride), and derivatives, copolymers and mixtures thereof.

In any of the devices described herein, the nominal molecule weight cutoff (MWCO) of the semi-permeable membrane is between 10 and 1000 KD (e.g., 10, 25, 50, 75, 100, 125, 150, 175, 200, 225, 250, 275, 300, 325, 350, 375, 400, 425, 450, 475, 500, 550, 600, 650, 700, 750, 800, 850, 900, 950 or 1000 KD). The semi-permeable membrane may be between about 10-200 μm (e.g. 10, 20, 30, 40, 50, 60, 70, 80, 90, 95, 100, 105, 110, 115, 120, 125, 130, 135, 140, 145, 150, 155, 160, 165, 170, 175, 180, 185, 190, 195 or 200 μm) thick. The length of the device can be between about 1 mm-20 mm (e.g., 1, 2, 3, 4, 5, 6, 7, 8, 9, 10, 11, 12, 13, 14, 15, 16, 17, 18, 19, or 20). In some embodiments, the device has an internal diameter of between about 0.1 mm-2.0 mm (e.g., 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0).

In one embodiment, the ends of the device are sealed using methyl methacrylate or any other medical-grade, biocompatible material formulated or manufactured to form a hermetic seal integrating all components of the device at each end of the device.

Also provided are uses of any of the implantable cell culture devices to deliver an appropriate therapeutic dose of any biologically active molecule(s) to a target region of a subject. For example, the therapeutic dose is at least 0.1 pg/day (e.g., at least 0.1, 0.5, 1, 5, 10, 20, 30, 40, 50, 60, 70, 80, 90, 100, 200, 300, 400, 500, 1000, 1500, 2000, 2500, 3000, 3500, 4000, 5000, 5500, 6000, 6500, 7000, 7500, 8000, 8500, 9000, 9500, 10000, 20000, 30000, 40000, 50000, 60000, 70000, 80000, 90000, 100000, $1 \times 10^6$, $1 \times 10^7$, $1 \times 10^8$, $1 \times 10^9$, $1 \times 10^{10}$ or more pg/day).

Also provided herein are methods for treating a disorder by implanting any of the implantable cell culture devices into a target region of a patient, and allowing soluble receptors or anti-angiogenic antibodies and molecules to diffuse from the device and bind to VEGF and/or PDGF in the target region, thereby treating the disorder. For example, cell lines (i.e., any of the cell lines described herein) are provided for use in treating a disorder, wherein the cell lines are incorporated in an implantable cell culture device, wherein the devices are implanted into a target region of a patient, and wherein, one or more soluble receptors or anti-angiogenic antibodies and molecules to diffuse from the device and bind to VEGF and/or PDGF in the target region, thereby treating the disorder.

Also provided are methods for treating a disorder by implanting any of the implantable cell culture devices into a target region of a patient, and allowing one or more biologically active molecules to diffuse from the device in the target region, thereby treating the disorder. For example, also provided are cell lines (i.e., any of the cell lines described herein) for use in treating a disorder, wherein the cell lines are incorporated in an implantable cell culture device, wherein the devices are implanted into a target region of a patient, and wherein one or more biologically active molecules diffuse from the device in the target region, thereby treating the disorder.

The skilled artisan could readily determine which disorder(s) can be treated by the device. Exemplary disorders that can be treated by any of the devices include, but are not limited to, ophthalmic disorders, endothelial cell proliferation or vascularization related disorders, cancer, infectious disorders, inflammatory disorders, immunologic disorders, digestive disorders, vascular disorders, lung disorders, oral disorders, blood disorders, liver disorders, skin disorders, prostate disorders, kidney disorders, metabolic disorders, endocrine disorders, neurologic disorders, and/or neurodegenerative disorders.

For example, the ophthalmic disorders to be treated are associated with the general disease groups angiogenesis, inflammation or degeneration and include, but are not limited to, branch or central retinal vein occlusion (BRVO or CRVO), uveitis, macular telangiectasia, retinopathy of prematurity, diabetic macular edema, diabetic retinopathy, age-related macular degeneration (e.g. wet form age-related macular degeneration or atrophic AMD (also called the dry form of AMD)), glaucoma, retinitis pigmentosa, cataract formation, retinoblastoma and retinal ischemia. In some embodiments, age-related macular degeneration is wet form age-related macular degeneration. In other embodiments, the ophthalmic disorder is BRVO or CRVO.

For example, the cell proliferation disorder may be selected from hematologic disorders, atherosclerosis, inflammation, increased vascular permeability and/or malignancy.

In such methods, a therapeutically effective amount (for example, between 0.1 pg and 10 mg per patient per day) of the soluble receptors or anti-angiogenic antibodies and molecules diffuse into the target region, wherein the soluble receptor is a soluble VEGF receptor or a soluble PDGF receptor.

Alternatively, a therapeutically effective amount (for example, between 0.1 pg and 10 mg per patient per day) of the biologically active molecules diffuses into the target region.

Those skilled in the art will recognize that any of the devices described herein can also be used to treat a variety of non-ocular disorders. For non-ocular disorders, the design of the devices will have to be modified. Modification of the device design is within the routine level of skill in the art.

Also provided are methods of delivering one or more biologically active molecules to a recipient host by implanting any of the implantable cell culture devices described herein into a target region of the recipient host, wherein the one or more encapsulated cells or cell lines (e.g., ARPE-19 cells) secrete the biologically active molecules at the target region.

In any method(s) described herein, preferred target regions can include, but are not limited to, the aqueous and vitreous humors of the eye, spleen, ear, heart, colon, liver, kidney, breast, joint, bone marrow, subcutaneous, and/or peritoneal spaces. Other target regions may include, but are not limited to, the whole body for systemic delivery and/or localized target sites within or near organs in the body such as breast, colon, spleen, ovary, testicle, and/or bone marrow.

In such methods, a therapeutically effective amount per patient per day of the biologically active molecules diffuses into the target region.

Those skilled in the art will recognize that in any of the methods and uses described herein with regard to ocular implantation and/or disorders, between 0.1 pg and 10,000 µg per patient per day of biologically active molecule(s) can diffuse from the implantable cell culture devices. For systemic implantation into other target regions of the body, the therapeutically effective amount could be upwards of 1000 mg per patient per day. For such systemic indications, those skilled in the art will recognize that far larger ECT devices would have to be employed.

Also provided are methods for making the implantable cell culture devices. For example, the device can be made by a method including the steps of genetically engineering at least one cell to secrete one or more biologically active molecules; producing an individual chamber; and assembling two or more individual chambers to form the device. The method of making a device may also include a step of encapsulating the genetically engineered cells within a semipermeable membrane. In some embodiments, the step of encapsulating the genetically engineered cells is performed for each individual chamber before the assembling step. In some embodiments, the step of encapsulating the genetically engineered cells is performed for all the chambers at one time after the assembling step.

Also provided are methods of making the ECT cartridge devices where the two or more individual chambers are formed prior to the addition of the genetically engineered at least one ARPE-19 cell.

Preferably, any method s of making the ECT cartridge devices described herein involves degassing and prewetting step(s) to insure that all chambers of the cartridge device are filled. For example, the degassing/prewetting step is performed prior to the addition of the genetically engineered at least one ARPE-19 cell.

In any devices, the two or more individual chambers each may contain genetically engineered cells that secrete the same one or more biologically active molecules. Alternatively, the two or more individual chambers each may contain genetically engineered cells that secrete different one or more biologically active molecules.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

DETAILED DESCRIPTION OF THE INVENTION

Current encapsulated cell delivery devices used in treatment of retinitis pigmentosa or geographic atrophy (e.g., single implants of NT-503 Second Generation or NT-503-2 devices) are limited in their capability to achieve microgram production levels of encapsulated cell produced biologically active molecule (e.g., protein drug). With the assumption that the per-cell production or PCD (pictogram per cell per day) of the encapsulated cells has been optimized for maximum production, the amount of cells that can be encapsulated and the efficiency of those cells within a single chamber device are constrained. Constraints to higher production of protein are related to both viable cell number and the efficiency of protein production of the cells in the chamber. A desirable alternative would be an encapsulated implant design capable of improving cell viability allowing more cells to populate a device and, in addition, improving the per cell capability to produce the biologically active molecule following encapsulation and intraocular implant.

One potential modification to the single-chamber design of the second generation ECT devices is to increase the diameter and or length, thereby increasing the internal volume of the chamber and allowing more cells to be encapsulated and more biologically active molecule to be produced from the device. Another potential modification to the single-chamber design is to create flat-sheet devices to increase volume and importantly increasing surface-to-volume ratio. Other devices have also been conceptualized such as complex geometric designs that also would increase volume and surface to volume relationships. However, volume increases leading to cell number increases in a single chamber encapsulated device have significant limitations.

In studies conducted with single-chamber second generation devices with increasing internal diameter greater than 1 mm, the results were inversely proportional to increasing diameter and confirmed that there exists a maximum diffusion distance within which the population of cells must remain in order to maintain both viability and maximum cell production rate. Moreover, exceeding the length of current encapsulated cell implant devices are not practical in applications associated with eye due to anatomical volume constraints, while construction materials currently used in manufacture of cell encapsulation devices preclude complex geometric configurations (e.g., star-shaped, or other similar designs).

Therefore, there is a need for an encapsulated implant device capable of allowing increased cell encapsulation volumes while maintaining cell viability and maximizing biologically active molecule production.

Figure 5:
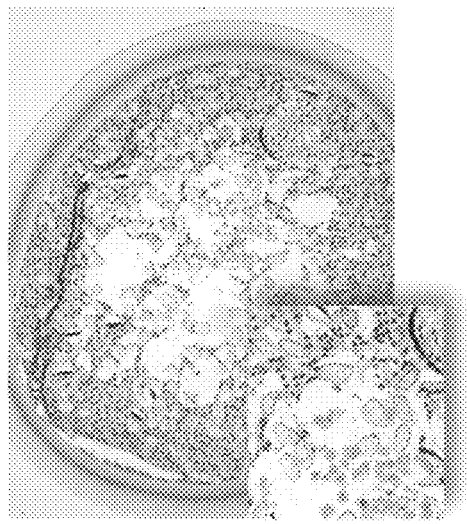
FIG. 5 is a histological cross-section of a 1.3 mm inner diameter, single chamber device showing cell necrosis occurred after a two-week intraocular implant in the rabbit.
Figure 6:
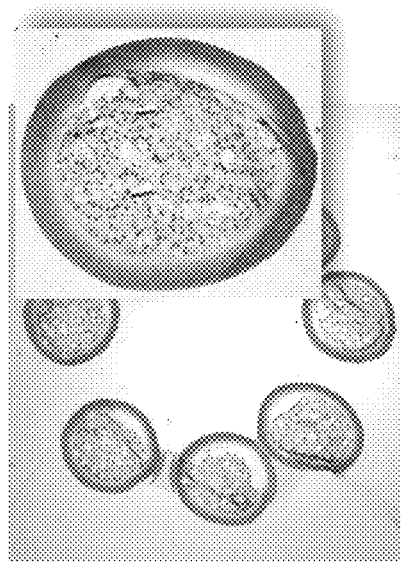
FIG. 6 is a histological cross-section of a cartridge implant with 7 individual chambers following a two-week intraocular implant in the rabbit. In contrast to the single implant with equivalent cell volume (FIG. 5), the cartridge configuration with reduced diffusion distance for each individually cell encapsulated chamber provides improved nutrient access and improved cell viability.

Accordingly, multi-chamber devices are provided that have superior properties compared to single-chamber devices known in the art. Particularly, these devices overcome the issue of increasing cell mass and diffusion distance constraints between the encapsulated cells and the nutrient source (e.g., human vitreous) by combining multiple, smaller inner diameter chambers into a cohesive, single implant cartridge format. For example, as shown in FIGS. 5 and 6, the multi-chamber configuration (FIG. 6) provides better nutrient access, thereby improving cell viability, when compared to a single-chamber device with equivalent cell volume (FIG. 5).

Figure 1:
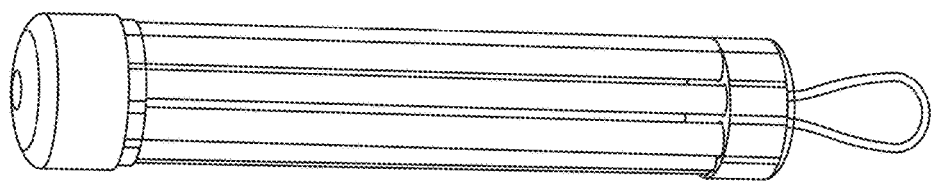
FIG. 1 shows a series of cartridge configurations with increasing number of individual chambers.
Figure 1:
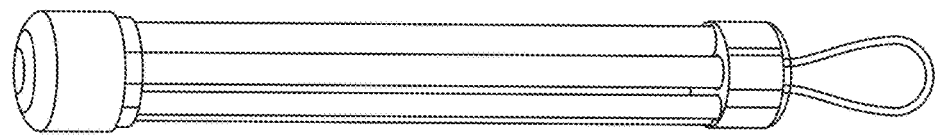
Figure 1:
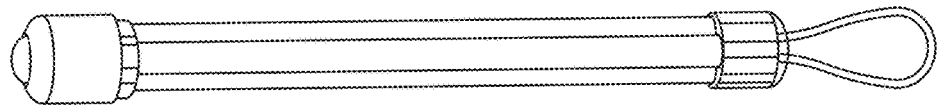
Figure 2:
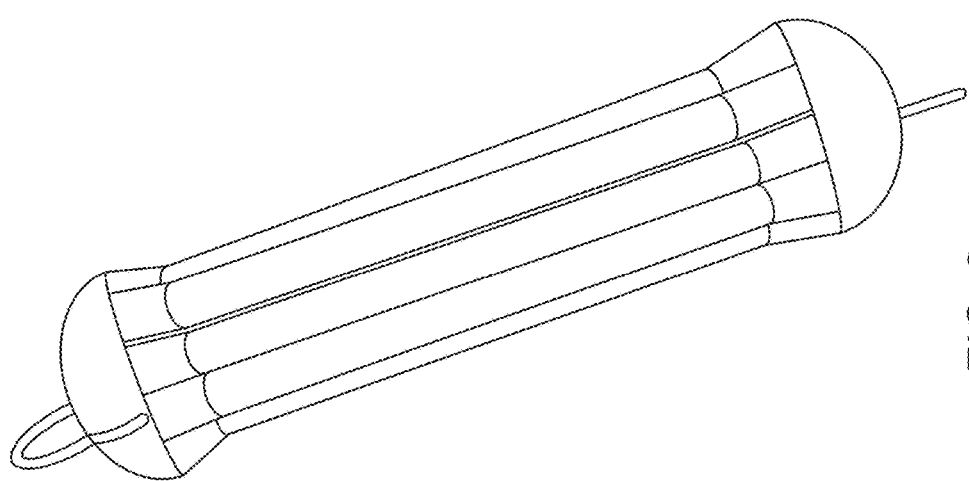
FIG. 2 shows a prototype cartridge with eight individual chambers each created from 400 micron inner diameter membranes with 50 micron wall thickness.

Hence, provided herein is an implantable cell culture device (also called a cartridge) that contains two or more (i.e., 2, 3, 4, 5, 6, 7, 8, 9, 10, 11, 12, 13, 14, 15, 16, 17, 18, 19, 20, or more) individual chambers. Each individual chamber includes a core that contains a therapeutically effective amount of one or more biologically active molecules from a cellular source and/or from a non-cellular source, and a semi-permeable membrane surrounding the core that permits the diffusion of the biologically active molecules there through. (See, e.g., FIGS. 1 and 2).

The one or more biologically active molecules can be isolated and purified from cells or tissue sources by any known standard protein purification techniques in the art. Alternatively, the one or more biologically active molecules can be produced by any recombinant DNA techniques known in the art. The one or more biologically active molecules can also be synthesized chemically using standard peptide synthesis techniques available in the art.

In some embodiments, the one or more biologically active molecules are produced by one or more genetically engineered cell lines, such as, a cell line comprising one or more genetically engineered ARPE-19 cells. However, those skilled in the art will recognize that any other suitable cell line can also be utilized in these devices.

In some embodiments, the cells are genetically engineered using any suitable techniques known in the art. In other embodiments, the one or more biologically active molecules can be introduced into the cells (e.g., APRE-19 cells) by an iterative transfection process that comprises one, two, three or more transfections (e.g., 4, 5, 6, 7, 8, 9, 10, or more). The iterative transfection process can be used to introduce multiple copies of the same or different biologically active molecule(s) into the cells (e.g., ARPE-19 cells). Each transfection can be carried out by any methods known in the art. The iterative transfection process is also described in WO 2012/075184, which is incorporated herein by reference.

A gene of interest (i.e., a gene that encodes a given biologically active molecule) can be inserted into a cloning site of a suitable expression vector using standard techniques known in the art.

A wide variety of host/expression vector combinations may be used to express the gene encoding the biologically active molecule(s) of interest. Long-term, stable in vivo expression is achieved using expression vectors (i.e., recombinant DNA molecules) in which the gene of interest is operatively linked to a promoter that is not subject to down regulation upon implantation in vivo in a mammalian host. Suitable promoters include, for example, strong constitutive mammalian promoters, such as beta-actin, eIF4A1, GAPDH, etc. Stress-inducible promoters, such as the metallothionein 1 (MT-1) or VEGF promoter may also be suitable. Additionally, hybrid promoters containing a core promoter and custom 5' UTR or enhancer elements may be used. Other known non-retroviral promoters capable of controlling gene expression, such as CMV or the early and late promoters of SV40 or adenovirus are suitable. Enhancer elements may also be place to confer additional gene expression under stress environments, such as low $O_2$. One example is the erythropoietin enhancer which confers up-regulation of associated gene elements upon hypoxic induction.

The expression vectors containing the gene of interest may then be used to transfect the desired cell line. Standard transfection techniques such as liposomal, calcium phosphate co-precipitation, DEAE-dextran transfection or electroporation may be utilized. Commercially available mammalian transfection kits, such as Fugene6 (Roche Applied Sciences), may be purchased. Additionally, viral vectors may be used to transducer the desired cell line. An example of a suitable viral vector is the commercially available pLenti family of viral vectors (Invitrogen). Human mammalian cells can be used. In all cases, it is important that the cells or tissue contained in the device are not contaminated or adulterated. For antibody scaffold proteins requiring heavy and light chain components, dual constructs, each encoding a relevant antibody heavy or light chain, can be co-transfected simultaneously, thereby yielding cell lines expressing functional bivalent Fab and tetravalent full antibody molecules.

Exemplary promoters include the SV40 promoter and the CMV/EF1alpha promoter. Other useful expression vectors, for example, may consist of segments of chromosomal, non-chromosomal and synthetic DNA sequences, such as various known derivatives of SV40 and known bacterial plasmids, e.g., pUC, pBlueScript™ plasmids from *E. coli* including pBR322, pCR1, pMB9 and their derivatives. Expression vectors containing the geneticin (G418), hygromycin or blasticidin drug selection genes (Southern, P. J., *In Vitro*, 18, p. 315 (1981), Southern, P. J. and Berg, P., J. Mol. Appl. Genet., 1, p. 327 (1982)) are also useful. These vectors can employ a variety of different enhancer/promoter regions to drive the expression of both a biologic gene of interest and/or a gene conferring resistance to selection with toxin such as G418, hygromycin B, or blasticidin. A variety of different mammalian promoters can be employed to direct the expression of the genes for G418 and hygromycin B and/or the biologic gene of interest. The G418 resistance gene codes for aminoglycoside phosphotransferase (APH) which enzymatically inactivates G418 (100-1000 µg/µl) added to the culture medium. Only those cells expressing the APH gene will survive drug selection usually resulting in the expression of the second biologic gene as well. The hygromycin B phosphotransferase (HPH) gene codes for an enzyme which specifically modifies hygromycin toxin and inactivates it. Genes co-transfected with or contained on the same plasmid as the hygromycin B phosphotransferase gene will be preferentially expressed in the presence of hygromycin B at 50-200 µg/ml concentrations.

Examples of expression vectors that can be employed include, but are not limited to, the commercially available pRC/CMV (Invitrogen), pRC/RSV (Invitrogen), pCDNA1NEO (Invitrogen), pCI-Neo (Promega), pcDNA3.3 (Invitrogen) and GS vector system (Lonza Group, Switzerland). Other suitable commercially available vectors include pBlast, pMono, or pVitro. In some embodiments, the expression vector system is the pCpGfree-vitro expression vectors available with neomycin (G418), hygromycin, and blasticidin resistance genes (InvivoGen, San Diego, Calif.).

In some embodiments, the pNUT expression vector, which contains the cDNA of the mutant DHFR and the entire pUC18 sequence including the polylinker, can be used. See, e.g., Aebischer, P., et al., Transplantation, 58, pp. 1275-1277 (1994); Baetge et al., PNAS, 83, pp. 5454-58 (1986). The pNUT expression vector can be modified such that the DHFR coding sequence is replaced by the coding sequence for G418 or hygromycin drug resistance. The SV40 promoter within the pNUT expression vector can also be replaced with any suitable constitutively expressed mammalian promoter, such as those discussed above.

Those skilled in the art will recognize that any other suitable, commercially available expression vectors (e.g., pcDNA family (Invitrogen), pBlast, pMono, pVitro, or pCpG-vitro (Invivogen)) can also be used. Principal elements regulating expression are typically found in the expression cassette. These elements include the promoter, 5' untranslated region (5' UTR) and 3' untranslated region (3' UTR). Other elements of a suitable expression vector may be critical to plasmid integration or expression but may not be readily apparent. The skilled artisan will be able to design and construct suitable expression vectors for use in the claimed invention. The choice, design, and/or construction of a suitable vector is well within the routine level of skill in the art.

The sequences suitable biologically active molecule(s) that can be used have also been published and/or are known in the art. Other genes encoding the biologically active molecules that are not publicly available may be obtained using standard recombinant DNA methods such as PCR amplification, genomic and cDNA library screening with oligonucleotide probes.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al, MOLECULAR CLONING: A LABORATORY MANUAL, 2$^{nd}$ ed., Cold Spring Harbor Laboratory, Cold Spring Harbor Laboratory Press, Cold Spring Harbor, N.Y. 1989), and other laboratory manuals.

The cell of choice is the ARPE-19 cell line, a spontaneously arising continuous human retinal pigmented epithelial cell line. However, those skilled in the art will recognize that other suitable cells, including but not limited to CHO cells, BHK cells, RPE (primary cells or immortalized cells), can also be used. The choice of cell depends upon the intended application. The encapsulated cells may be chosen for secretion of a biologically active molecule. Cells can also be employed which synthesize and secrete agonists, analogs, derivatives or fragments of the construct, which are active. Those skilled in the art will recognize that other suitable cell types may also be genetically engineered to secrete biologically active molecule(s).

To be a platform cell line for an encapsulated cell based delivery system, the cell line should have as many of the following characteristics as possible: (1) the cells should be hardy under stringent conditions (the encapsulated cells should be functional in the avascular tissue cavities such as in the eye, especially in the intra-ocular environment); (2) the cells should be able to be genetically modified (the desired therapeutic factors needed to be engineered into the cells); (3) the cells should have a relatively long life span (the cells should produce sufficient progenies to be banked, characterized, engineered, safety tested and clinical lot manufactured); (4) the cells should be of human origin (which increases compatibility between the encapsulated cells and the host); (5) the cells should exhibit greater than 80% viability for a period of more than one month in vivo in device (which ensures long-term delivery); (6) the encapsulated cells should deliver an efficacious quantity of a useful biological product (which ensures effectiveness of the treatment); (7) the cells should have a low level of host immune reaction (which ensures the longevity of the graft); and (8) the cells should be nontumorigenic (to provide added safety to the host, in case of device leakage).

The ARPE-19 cell line (see Dunn et al., 62 Exp. Eye Res. 155-69 (1996), Dunn et al., 39 Invest. Ophthalmol. Vis. Sci. 2744-9 (1998), Finnemann et al., 94 Proc. Natl. Acad. Sci. USA 12932-7 (1997), Handa et al., 66 Exp. Eye. 411-9 (1998), Holtkamp et al., 112 Clin. Exp. Immunol. 34-43 (1998), Maidji et al., 70 J. Virol. 8402-10 (1996); U.S. Pat. No. 6,361,771) demonstrates all of the characteristics of a successful platform cell for an encapsulated cell-based delivery system. The ARPE-19 cell line is available from the American Type Culture Collection (ATCC Number CRL-2302). ARPE-19 cells are normal retinal pigmented epithelial (RPE) cells and express the retinal pigmentary epithelial cell-specific markers CRALBP and RPE-65. ARPE-19 cells form stable monolayers, which exhibit morphological and functional polarity.

The inner diameters of each individual chamber and the number of individual chambers can be optimized to create a cartridge with the maximum encapsulated cell efficiency and biologically active molecule production. The inner diameter of each individual chamber can be between 100 microns and 900 microns (i.e., 100, 200, 300, 400, 500, 600, 700, 800 or 900 μm) and bundled in numbers between 2 and 20 chambers (i.e., 2, 3, 4, 5, 6, 7, 8, 9, 10, 11, 12, 13, 14, 15, 16, 17, 18, 19, or 20). The wall thicknesses of each chamber should be manufactured to create the minimal diffusion distance yet achieve adequate column strength. The nominal ratio of inner diameter to wall thickness of each chamber is about 5:1 to 20:1 in scale. For example, the ratio is 5:1, 6:1, 7:1, 8:1, 9:1, 10:1, 11:1, 12:1, 13:1, 14:1, 15:1, 16:1, 17:1, 18:1, 19:1 or 20:1 in scale. In one example, the ratio is 10:1 in scale.

The overall size of the cartridge implant will vary depending upon the number and size of the individual chambers used in the assembly. The range of diameter of the cartridge can be between 0.5 mm and 5.0 mm (i.e., 0.5, 1.0, 1.5, 2.0, 2.5, 3.0, 3.5, 4.0, 4.5, or 5.0 mm) with lengths varying from a minimum of 0.4 mm to a maximum of 11 mm (i.e., 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5 or 11 mm) The internal volumes have a respective range depending upon the cartridge format and could vary from a minimum of 2 microliters to a maximum of 100 microliters (i.e., 2, 3, 4, 5, 6, 7, 8, 9, 10, 15, 20, 25, 30, 35, 40, 45, 50, 55, 60, 65, 70, 75, 80, 85, 90, 95 or 100 μl).

Figure 3:
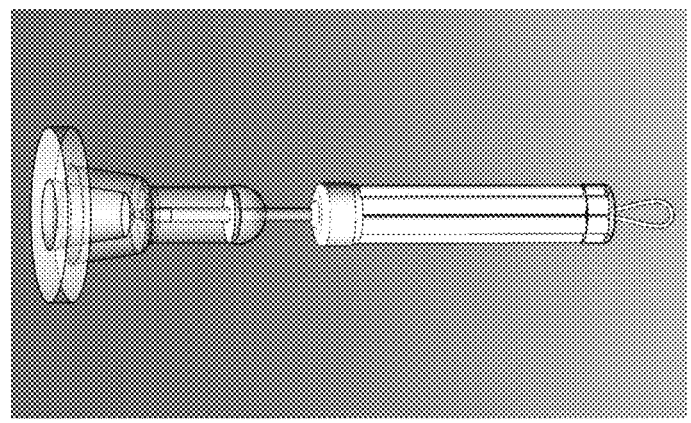
FIG. 3 is a cartoon describing the single access port allowing encapsulation of one cell line or multiple mixed cell lines in all the chambers.
Figure 4:
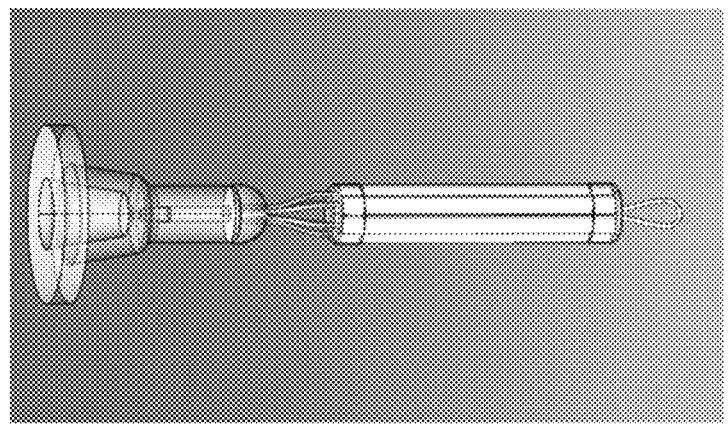
FIG. 4 is a cartoon describing the multiple access ports allowing encapsulation of individual cell line in each chamber. This configuration allows delivery of two, three or more distinct and therapeutically different drug products from a single intraocular device.

The cartridge may further contain one or more access ports located on either end or at both ends of the device. Each individual chamber can be accessed individually through one access port (see, FIG. 4). Alternatively, two or more chambers within a cartridge can be accessed through a single central access port (see, FIG. 3).

Thus, when some or all the individual chambers of the device share a single port, a single suspension of one or more biologically active molecules is encapsulated within those chambers that share a single port. If the one or more biologically active molecules are produced by one or more genetically engineered cell lines, a single suspension of cells (one type of genetically engineered cells or a mixture of genetically engineered cells) that secretes the same one or more biologically active molecules is encapsulated within those chambers that share the single port. The increased number of individual chambers and decreased diffusion distance to the nutrient source will increase efficiency of the encapsulated cells and will allow either improved secretion levels of a protein drug compared to a single chamber device containing equivalent cell volume or can allow for viable support of a greater volume of cells and greater secretion of protein drug levels compared to a single chamber or equivalent internal volume.

Alternatively, when each individual chamber has its own access port, different suspension of one or more biologically active molecules can be encapsulated within each individual chamber. If the one or more biologically active molecules are produced by one or more genetically engineered cell lines, different cell suspensions are encapsulated within each individual chamber. Each encapsulated cell line produces a specific protein drug or drugs (i.e., one or more biologically active molecules) at a level consistent with the respective encapsulated cell line volume yet remains isolated within the individual chambers and/or groups of chambers. This configuration allows delivery of two, three, four, five, six, seven or more (i.e., 8, 9, 10, 11, 12, 13, 14, 15, 16, 17, 18, 19, 20 or n, where n is the total number of chambers) distinct and therapeutically different biologically active molecules from a single intraocular cartridge device.

The core of each individual chamber can function as a reservoir for biologically active molecules. In some embodiments, the core of each individual chamber may further contain a matrix disposed within the semi-permeable membrane. For example, the matrix may comprise a plurality of monofilaments that are either twisted into a yarn or woven into a mesh or twisted into a yarn that is in non-woven stands where the encapsulated cells are distributed. Materials useful in making monofilaments include any biocompatible materials that are able to be formed into fibers such as, for example, acrylic, polyester, polyethylene, polypropylene, polyacrylonitrile, polyethylene terephthalate, nylon, polyamides, polyurethanes, polybutester, or natural fibers such as cotton, silk, chitin or carbon or biocompatible metals. These monofilaments may prevent cells from aggregating and improve cellular distribution within each chamber. (See PCT Publication No. WO 96/02646, incorporated herein by reference).

In some embodiments, the monofilaments is made from polyethylene terephthalate (PET) fibers that comprises 1-85% (e.g., 1%, 5%, 10%, 15%, 20%, 25%, 30%, 35%, 40%, 45%, 50%, 55%, 60%, 65%, 70%, 75%, 80% or 85%) of the internal volume of each chamber of the device.

Various polymers and polymer blends can be used to manufacture the surrounding semi-permeable membrane in each chamber, including polysulfone (including polyether sulfones), polyvinyl pyroldone, polyacrylates (including acrylic copolymers), polyvinylidenes, polyvinyl chloride copolymers, polyurethanes, polystyrenes, polyamides, cellulose acetates, cellulose nitrates, polyphosphazenes, polyacrylonitriles, poly(acrylonitrile/covinyl chloride), as well as derivatives, copolymers and mixtures thereof. For example, the surrounding semi-permeable membrane is made from polysulfone or polyvinyl pyroldone. Preferably, the surrounding semipermeable membrane is a biocompatible semipermeable hollow fiber membrane. Such membranes and methods of making them are disclosed by U.S. Pat. Nos. 5,284,761 and 5,158,881, incorporated by reference.

In some embodiments, the surrounding semi-permeable membrane is made from a polyether sulfone hollow fiber, such as those described by U.S. Pat. No. 4,976,859 or U.S. Pat. No. 4,968,733, incorporated by reference.

In some embodiments, the surrounding semi-permeable membrane is a permselective, immunoprotective membrane. That is, it protects cells in the core of the chamber from the immune system of the individual in whom the device is implanted. It does so (1) by preventing harmful substances of the individual's body from entering the core, (2) by minimizing contact between the individual and inflammatory, antigenic, or otherwise harmful materials which may be present in the core and (3) by providing a spatial and physical barrier sufficient to prevent immunological contact between the isolated moiety and detrimental portions of the individual's immune system.

In some embodiments, the surrounding semi-permeable membrane is ultrafiltration membrane or a microfiltration membrane. Those skilled in the art will recognize that ultrafiltration membranes are those having a pore size range of from about 1 to about 100 nanometers while a microporous membrane has a range of between about 1 to about 10 microns.

To be permselective, the membrane has a nominal molecular weight cutoff (MWCO) range appropriate both to the type and extent of immunological reaction anticipated to be encountered after the device is implanted and to the molecular size of the largest substance whose passage into and out of the device into the eye is desirable. The surrounding semi-permeable membrane has nominal MWCO values from 10 kD up to 1000 kD. For example, the MWCO is between 50-700 kD or between 50-500 kD and ideally approximately 300 kD. In some embodiments, the MWCO is 500 kD. The median pore size of the membrane has a median pore size of approximately 1-500 nm (i.e., 1, 10, 20, 30, 40, 50, 75, 100, 125, 150, 175, 200, 225, 250, 275, 300, 325, 350, 375, 400, 425, 450, 475 or 500 nm).

The thickness of this physical barrier (i.e., semi-permeable membrane) can vary, but it will always be sufficiently thick to prevent direct contact between the cells and/or substances on either side of the barrier. The thickness of this region generally ranges between 5 and 200 microns. For example, thicknesses of 10 to 100 microns or of 20 to 50 or 20 to 75 microns can be used. In some embodiments, the semi-permeable membrane is between 90 and 120 μm thick. Types of immunological attack which can be prevented or minimized by the use of the instant device include attack by macrophages, neutrophils, cellular immune responses (e.g., natural killer cells and antibody-dependent T cell-mediated cytolysis (ADCC)), and humoral response (e.g., antibody-dependent complement mediated cytolysis).

The surrounding semi-permeable membrane is produced in such a manner that it is free of isolated cells, and completely surrounds (i.e., isolates) the core, thereby preventing contact between any cells in the core and the recipient's body. The surrounding semi-permeable membrane is formed into a porous structure in each chamber of the device.

The device may have a tether that aids in maintaining device placement during implant, and aids in retrieval. Such a tether may have any suitable shape that is adapted to secure the cartridge in place. For example, the tether may be a loop, a disk, or a suture. In some embodiments, the tether is shaped like an eyelet, so that a suture may be used to secure the tether (and thus the device) to the sclera, or other suitable ocular structure. In another embodiment, the tether is continuous with the cartridge at one end, and forms a pre-threaded suture needle at the other end. In one embodiment, the tether is an anchor loop that is adapted for anchoring the cartridge to a structure within the target region (for example, an ocular structure). The tether may be constructed of a shape memory metal and/or any other suitable medical grade material known in the art.

Any suitable method of sealing the capsules know in the art may be used, including the employment of polymer adhesives and/or crimping, knotting and heat sealing. In addition, any suitable "dry" sealing method can also be used. In such methods, a substantially non-porous fitting is provided through which the cell-containing solution is introduced. Subsequent to filling, the capsule is sealed. Such methods are described in, e.g., U.S. Pat. Nos. 5,653,688; 5,713,887; 5,738,673; 6,653,687; 5,932,460; and 6,123,700, which are herein incorporated by reference. In some embodiments, the ends of the device are sealed using methyl methacrylate. Additional suitable sealants include any other medical-grade, biocompatible material formulated or manufactured to form a hermetic seal integrating all components of the device at each end of the device.

Devices may be manufactured, formed and/or assembled by any suitable method known in the art. (See, e.g., U.S. Pat. Nos. 6,361,771; 5,639,275; 5,653,975; 4,892,538; 5,156,844; 5,283,138; and 5,550,050, each of which is incorporated herein by reference). For example, the device can be made by a method including steps of genetically engineering at least one cell to secrete one or more biologically active molecules; producing an individual chamber; and assembling two or more individual chambers to form the device. The method of making a device may also include a step of encapsulating the genetically engineered cells within a semipermeable membrane of the individual camber. In some embodiments, the step of encapsulating the genetically engineered cells is performed for each individual chamber before the assembling step (e.g., the cells are encapsulated in the individual chambers before the device is assembled). In other embodiments, the step of encapsulating the genetically engineered cells is performed for all the chambers after the assembling step (e.g., the device is assembled first and then the cells are added to individual chambers). Alternatively, for some individual chambers, the genetically engineered cells are encapsulated prior to the assembling step and for other individual chambers, the genetically engineered cells are encapsulated after the assembling step.

Cell filling (i.e., encapsulation) of cartridges containing 2 or more (e.g., 2, 3, 4, 5, 6, 7, 8, 9, 10, or more) individual chambers requires a degassing and pre-wetting stage to ensure optimal distribution of cell mass within all chambers of the cartridge. Failure to include this step during encapsulation results in unacceptable variability of cell filling in all chambers and potentially no filling in some chambers. (See Example 8, infra).

In single ECT device loading, the air initially inside the device is expelled through pores as the cell suspension liquid pushes the air into and out of the dry pores of the device membrane. Cells accumulate within the internal space of the single ECT device during this step as the liquid medium of the cell suspension ultrafiltrates across and out of the membrane pores.

However, in the cartridge configuration, this process is complicated due to several factors including an orientation of the cartridge device which is not equally vertical for all chambers resulting in preferential ultrafiltrate of liquid from some chambers relative to others and resulting in contact and accumulation of that ultrafiltrate liquid on the outer surface of the remaining gas-filled chambers of the cartridge. The pores in those chamber membranes with liquid contact on outer surface prior to "degassing" are then are blocked, essentially creating a barrier to air passage and to subsequent liquid ultrafiltration.

The back pressure created due to the blocked chambers directs the liquid cell suspension through those remaining "degassed" chambers, which remain open to ultrafiltration, ultimately resulting in overfilling or cell packing. Those chambers unfilled or partially filled will not repopulate and, therefore, it was critical to develop and employ a system to equilibrate filling of all chambers of a cartridge in the multi-chamber filling process of an ECT cartridge device.

Figure 21:
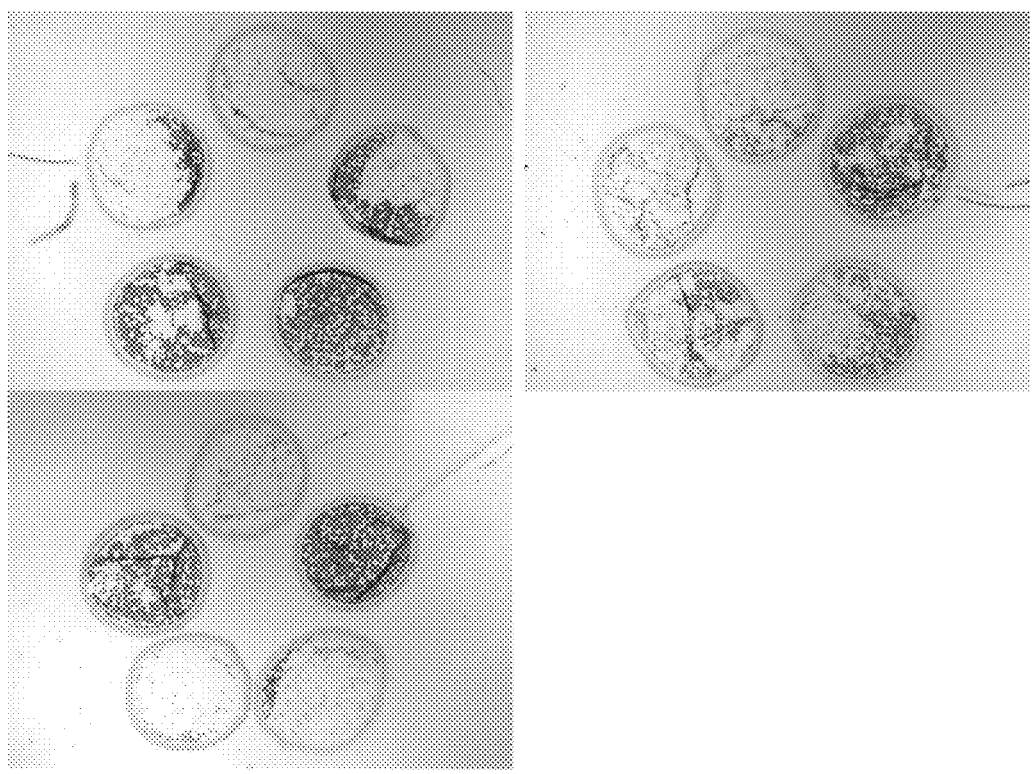
FIG. 21 shows representative examples of cartridge devices without degassing/pre-wetting procedure (shown are histologic cross-sections, cells stained with Eosin and Hemotoxylin). Lack of complete filling is evident in as many as all five of the cartridge chambers when cells filled without a pre-wetting and degassing step.

FIG. 21 shows representative examples of cartridge devices without this degassing/pre-wetting procedure.

To ensure that all chambers would be equally filled and distributed with encapsulated cells, all air was evacuated from the internal volume of the device and the filling port (e.g., vacuum degassing), and importantly, all surfaces, particularly each chamber membrane surface and interconnecting pores, were filled with a wetting liquid (such as Hanks Balanced Salt Solution or other isotonic solutions (e.g., saline, DMEM, etc.).

Following degassing and liquid filling of the cartridge and cell-filling system, the cartridge device can be successfully loaded with cells per any established encapsulation methods known in the art.

Figure 22:
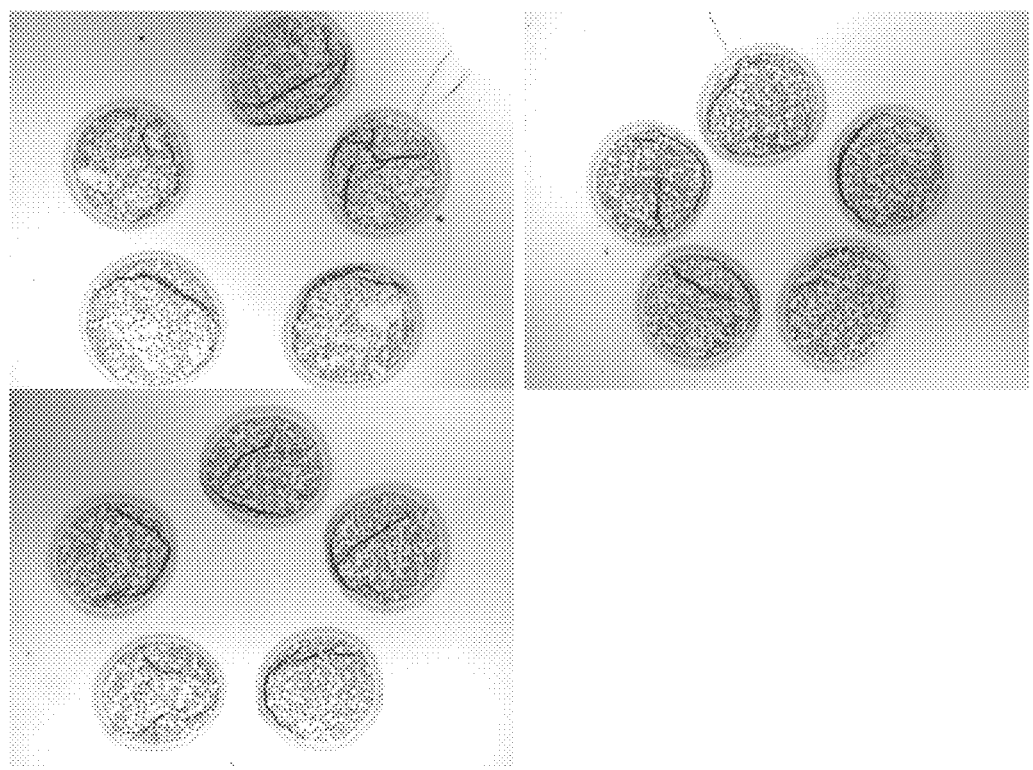
FIG. 22 shows representative examples of cartridge devices following implementation of a degassing/pre-wetting (shown are histologic cross-sections, cells stained with Eosin and Hemotoxylin). Complete filling evident in all five chambers of each representative cartridge device in following a degassing and pre-wetting step.

FIG. 22 shows representative examples of cartridge devices after implementation of a degassing/pre-wetting step. Those skilled in the art will recognize that any devices may be cryopreserved following manufacture and prior to administration and/or implementation. Cryopreservation, if successful, helps to improve the shelf-life of the devices, which, in turn, would improve device storage and/or simplify device manufacturing.

Any suitable cryopreservation known in the art can be used to cryopreserve any of the devices described herein.

For example, cryopreservation in vapor phase liquid nitrogen is an established method for long term storage of living cells, and is dependent on appropriate cryoprotectant agents and the ability of cells to survive ultra-low temperature conditions. Once optimal conditions are met for cryopreservation, cells may be stored nearly indefinitely within vapor phase liquid nitrogen. By way of non-limiting example, using a cryopreservation system, any of the devices can be filled with cells formulated with cryoprotectant agent (e.g., 10% glycerol), placed in cryogenic storage vials, frozen under controlled rate freezing (e.g., to −80° C.), and finally stored in vapor phase liquid nitrogen (e.g., −190° C.) conditions. However, any other cryopreservation method(s) known in the art can also be used. Determination of the appropriate cryopreservation method(s) is within the routine level of skill in the art.

In addition, because the entire supply chain is simplified, any of the devices can be transported under vapor phase liquid nitrogen (−190° C.) conditions and/or dry ice (−70° C.) conditions (or any combination(s) thereof).

Cryopreserved devices can be thawed using any suitable method or protocol known in the art prior to use.

Additional cryopreservation agents and processes are described in WO 2013/181424, the contents of which are incorporated herein by reference in their entireties.

In any devices or methods, the one or more biologically active molecules are selected from the group consisting of anti-angiogenic antibodies and molecules, anti-angiogenic antibody scaffolds, soluble receptors, agents targeting and inhibiting or modulating immunologic pathway molecules, growth factor inhibitors, cytokines (interleukins, lymphokines), growth factors, neurotrophic factors (neurotrophins), angiogenic factors, neurotransmitters, hormones, enzymes, anti-inflammatory factors, therapeutic proteins, gene transfer vectors, antibodies and antibody fragments, antigens, and any combination thereof. Anti-angiogenic antibody-scaffolds and anti-angiogenic molecules that can be used are described in WO 2012/075184, which is herein incorporated by reference.

For example, the anti-angiogenic antibody scaffolds and/or anti-angiogenic molecules may include one or more of the following:

1) p834 (VEGFR-Fc#1, [RS-VEGF Receptor 1, Domain 2 and VEGF Receptor 2, Domain 3 (R1D2-R2D3)]-EFEPKSC-hIgG1 Fc)
2) p838 (VEGFR-Fc#2, [VEGF Receptor 2, Domains 1, 2, and 3 (R2D1-R2D2-R2D3)])
3) p876 (VEGF antibody ScFv#1, with His-tag)
4) p913 (VEGF antibody ScFv#2, without His-tag)
5) p873 (Aflibercept, VEGFR-Fc#3, VEGF Receptor 1, Domain 2 and VEGF Receptor 2, Domain 3 (R1D2-R2D3) hIgG1 Fc)
6) p874/p875 (Bevacizumab, VEGF full antibody #1, heavy chain/light chain)
7) p915/p914 (Ranibizumab, VEGF antibody Fab, heavy chain fragment/light chain)
8) p916/p914 (Ranibizumab, VEGF full antibody #2, heavy chain/light chain)
9) p917 (VEGFR-Fc#1, [RS-VEGF Receptor 1, Domain 2 and VEGF Receptor 2, Domain 3 (R1D2-R2D3)]-hIgG1 Fc)
10) p964 (PDGFR-Beta domains 1-5 receptor-IgG4 Fc fusion)
11) p963 (PDGFR-Beta domains 1-5 receptor-IgG1 Fc fusion)
12) p974 (PDGFR-Beta domains 1-3 receptor-IgG1 Fc fusion)
13) p978 (PDGFR-Beta domains 1-5 receptor)
14) p977 (PDGFR-Beta domains 1-5 receptor plus His6 tag)

p834

(SEQ ID NO: 1)

```
atggtcagctactgggacaccggggtcctgctgtgcgcgctgctcagctgtctgcttctcacaggatc
tagttcaggttcgcgaagtgatacaggtagaccttcgtagagatgtacagtgaaatccccgaatta
tacacatgactgaaggaagggagctcgtcattccctgccgggttacgtcacctaacatcactgttact
ttaaaaaagtttccacttgacactttgatccctgatggaaaacgcataatctgggacagtagaagggg
cttcatcatatcaaatgcaacgtacaaagaaatagggcttctgacctgtgaagcaacagtcaatgggc
atttgtataagacaaactatctcacacatcgacaaaccaatacaatcatcgatgtggttctgagtccg
tctcatggaattgaactatctgttggagaaaagcttgtcttaaattgtacagcaagaactgaactaaa
tgtggggattgacttcaactgggaatacccttcttcgaagcatcagcataagaaacttgtaaaccgag
acctaaaaacccagtctgggagtgagatgaagaaattttgagcaccttaactatagatggtgtaacc
cggagtgaccaaggattgtacacctgtgcagcatccagtgggctgatgaccaagaagaacagcacatt
tgtcagggtccatgaaaaagaattcgagcccaaatcttgtgacaaaactcacacatgcccaccgtgcc
cagcacctgaactcctgggggaccgtcagtcttcctcttcccccaaaacccaaggacaccctcatg
atctcccggaccccctgaggtcacatgcgtggtggtggacgtgagccacgaagaccctgaggtcaagtt
caactggtacgtggacggcgtggaggtgcataatgccaagacaaagccgcgggaggagcagtacaaca
gcacgtaccgtgtggtcagcgtcctcaccgtcctgcaccaggactggctgaatggcaaggagtacaag
tgcaaggtctccaacaaagcctcccagccccatcgagaaaaccatctccaaagccaaagggcagcc
ccgagaaccacaggtgtacaccctgccccatcccgggatgagctgaccaagaaccaggtcagcctga
cctgcctggtcaaaggcttctatcccagcgacatcgccgtggagtgggagagcaatgggcagccggag
aacaactacaagaccacgcctcccgtgctggactccgacggctccttcttcctctacagcaagctcac
cgtggacaagagcaggtggcagcaggggaacgtcttctcatgctccgtgatgcatgaggctctgcaca
accactacacgcagaagagcctctccctgtctccgggtaaa
```

(SEQ ID NO: 2)

```
mvsywdtgvllcallsclllltgsssgsrsdtgrpfvemyseipeiihmtegrelvipcrvtspnitvt
lkkfpldtlipdgkriiwdsrkgfiisnatykeiglltceatvnghlyktnylthrqtntiidvvlsp
shgielsvgeklvlnctartelnvgidfnweypsskhqhkklvnrdlktqsgsemkkflstltidgvt
rsdqglytcaassglmtkknstfvrvhekefepkscdkthtcppcpapellggpsvflfppkpkdtlm
isrtpevtcvvvdvshedpevkfnwyvdgvevhnaktkpreeqynstyrvvsvltvlhqdwlngkeyk
ckvsnkalpapiektiskakgqprepqvytlppsrdeltknqvsltclvkgfypsdiavewesngqpe
nnykttppvldsdgsfflyskltvdksrwqqgnvfscsvmhealhnhytqkslslspgk
``` p838

(SEQ ID NO: 3)

```
atggagagcaaggtgctgctggccgtcgccctgtggctctgcgtggagacccgggccgcctctgtggg
tttgcctagtgtttctcttgatctgcccaggctcagcatacaaaaagacatacttacaattaaggcta
atacaactcttcaaattacttgcaggggacagaggggacttggactggctttggcccaataatcagagt
ggcagtgagcaaagggtggaggtgactgagtgcagcgatggcctcttctgtaagacactcacaattcc
aaaagtgatcggaaatgacctggagcctacaagtgcttctaccgggaaactgacttggcctcggtca
tttatgtctatgttcaagattacagatctccatttattgcttctgttagtgaccaacatggagtcgtg
tacattactgagaacaaaaacaaaactgtggtgattccatgtctcgggtccatttcaaatctcaacgt
gtcactttgtgcaagatacccagaaaagagatttgttcctgatggtaacagaatttcctgggacagca
agaagggctttactattcccagctacatgatcagctatgctggcaggtcttctgtgaagcaaaaatt
aatgatgaaagttaccagtctattatgtacatagttgtcgttgtagggtataggatttatgatgtggt
tctgagtccgtctcatggaattgaactatctgttggagaaaagcttgtcttaaattgtacagcaagaa
ctgaactaaatgtggggattgacttcaactgggaatacccttcttcgaagcatcagcataagaaactt
gtaaaccgagacctaaaaacccagtctgggagtgagatgaagaaatttttgagcaccttaactataga
tggtgtaacccggagtgaccaaggattgtacacctgtgcagcatccagtgggctgatgaccaagaaga
```

-continued

```
acagcacatttgtcagggtccatgaaaaacctttgttgcttttggaagtggcgaattcgagcccaaa
tcttgtgacaaaactcacacatgccaccgtgcccagcacctgaactcctgggggaccgtcagtctt
cctcttcccccaaaacccaaggacaccctcatgatctcccggacccctgaggtcacatgcgtggtgg
tggacgtgagccacgaagaccctgaggtcaagttcaactggtacgtggacggcgtggaggtgcataat
gccaagacaaagccgcgggaggagcagtacaacagcacgtaccgtgtggtcagcgtcctcaccgtcct
gcaccaggactggctgaatggcaaggagtacaagtgcaaggtctccaacaaagccctcccagccccca
tcgagaaaaccatctccaaagccaaagggcagccccgagaaccacaggtgtacaccctgcccccatcc
cgggatgagctgaccaagaaccaggtcagcctgacctgcctggtcaaaggcttctatcccagcgacat
cgccgtggagtgggagagcaatgggcagccggagaacaactacaagaccacgcctcccgtgctggact
ccgacggctccttcttcctctacagcaagctcaccgtggacaagagcaggtggcagcaggggaacgtc
ttctcatgctccgtgatgcatgaggctctgcacaaccactacacgcagaagagcctctccctgtctcc
gggtaaa
```

(SEQ ID NO: 4)
meskvllavalwlcvetraasvglpsvsldlprlsiqkdiltikanttlqitcrgqrdldwlwpnnqs
gseqrvevtecsdglfcktltipkvigndtgaykcfyretdlasviyvvqdyrspfiasvsdqhgvv
yitenknktvvipclgsisnlnvslcarypekrfvpdgnriswdskkgftipsymisyagmvfceaki
ndesyqsimyivvvvgyriydvvlspshgielsvgeklvlnctartelnvgidfnweypsskhqhkkl
vnrdlktqsgsemkkflstltidgvtrsdqglytcaassglmtkknstfvrvhekpfvafgssgefepk
scdkthtcppcpapellggpsvflfppkpkdtlmisrtpevtcvvvdvshedpevkfnwyvdgvevhn
aktkpreeqynstyrvvsvltvlhqdwlngkeykckvsnkalpapiektiskakgqprepqvytlpps
rdeltknqvsltclvkgfypsdiavewesngqpennykttppvldsdgsfflyskltvdksrwqqgnv
fscsvmhealhnhytqkslslspgk p876

(SEQ ID NO: 5)
```
atggacatgcgggtgccagctcagctgctgggactgctgctgctgtggctgcccggcaccagatgcga
catccagctgacccagtccccctccagcctgtccgcctctgtgggcgacagagtgaccatcacctgtt
ccgcctcccaggacatcagcaactacctgaactggtatcagcagaagcccggcaaggcccccaaggtg
ctgatctacttccaccagcagcctgcactccggcgtgccctcccggttctccggctccggctccggcac
cgacttcacccctgaccatctccagcctgcagcccgaggacttcgccacctactactgccagcagtaca
gcaccgtgcccggaccttcggccagggcaccaaggtggaaatcaagggaggtggaggaagcggtgga
ggaggtagcggaggcggcggcagcgaggtgcagctggtggaatccggcggaggactggtgcagcctgg
cggctccctgagactgtcttgcgccgcctccggctacgacttcacccactacggcatgaactgggtcc
gacaggcccctggcaagggactggaatgggtgggctggatcaacacctacaccggcgagcccacctac
gccgccgacttcaagcggcggttcaccttcagcctggacaccagcaagagcaccgcctacctgcagat
gaactccctgcgggccgaggacaccgccgtgtactactgcgccaagtaccctactactacggcacca
gccactggtacttcgacgtgtggggccagggcacccctggtcaccgtctcctcacaccatcaccaccac
cac
```

(SEQ ID NO: 6)
mdmrvpaqllglllllwlpgtrcdiqltqspsslsasvgdrvtitcsasqdisnylnwyqqkpgkapkv
liyftsslhsgvpsrfsgsgsgtdftltisslqpedfatyycqqystvpwtfgqgtkveikggggsgg
ggsggggsevqlvesgglvqpggslrlscaasgydfthygmnwvrqapgkglewvgwintytgepty
aadfkrrftfsldtskstaylqmnslraedtavyycakypyyygtshwyfdvwgqgtlvtvsshhhhh
h p913

(SEQ ID NO: 19)
```
atggacatgcgggtgccagctcagctgctgggactgctgctgctgtggctgcccggcaccagatgcga
catccagctgacccagtccccctccagcctgtccgcctctgtgggcgacagagtgaccatcacctgtt
ccgcctcccaggacatcagcaactacctgaactggtatcagcagaagcccggcaaggcccccaaggtg
ctgatctacttccaccagcagcctgcactccggcgtgccctcccggttctccggctccggctccggcac
cgacttcacccctgaccatctccagcctgcagcccgaggacttcgccacctactactgccagcagtaca
gcaccgtgcccggaccttcggccagggcaccaaggtggaaatcaagggaggtggaggaagcggtgga
ggaggtagcggaggcggcggcagcgaggtgcagctggtggaatccggcggaggactggtgcagcctgg
cggctccctgagactgtcttgcgccgcctccggctacgacttcacccactacggcatgaactgggtcc
gacaggcccctggcaagggactggaatgggtgggctggatcaacacctacaccggcgagcccacctac
gccgccgacttcaagcggcggttcaccttcagcctggacaccagcaagagcaccgcctacctgcagat
gaactccctgcgggccgaggacaccgccgtgtactactgcgccaagtaccctactactacggcacca
gccactggtacttcgacgtgtggggccagggcacccctggtcaccgtctcctca
```

(SEQ ID NO: 20)
mdmrvpaqllglllllwlpgtrcdiqltqspsslsasvgdrvtitcsasqdisnylnwyqqkpgkapkv
liyftsslhsgvpsrfsgsgsgtdftltisslqpedfatyycqqystvpwtfgqgtkveikggggsgg
ggsggggsevqlvesgglvqpggslrlscaasgydfthygmnwvrqapgkglewvgwintytgepty
aadfkrrftfsldtskstaylqmnslraedtavyycakypyyygtshwyfdvwgqgtlvtvss p873

(SEQ ID NO: 7)
```
atggtcagctactgggacaccggggtcctgctgtgcgcgctgctcagctgtctgcttctcacaggatc
tagttcaggtagtgatacaggtagacctttcgtagagatgtcaggtgaaatcccgaaattatacaca
tgactgaaggaagggagctcgtcattcccgtccgggttacgtcacctaacatcactgttactttaaaa
aagttttccacttgacactttgatccctgatggaaaacgcataatctgggacagtagaaagggcttcat
catatcaaatgcaacgtacaaagaaatagggcttctgacctgtgaagcaacagtcaatgggcatttgt
ataagacaaactatctcacacatcgacaaaaccaatacaatcatcgatgtggttctgagtccgtccat
ggaattgaactatctgttggagaaaagcttgtcttaaattgtacagcaagaactgaactaaatgtggg
gattgacttcaactgggaataccttcttgaagcatcagcataagaaacttgtaaaccgagacctaa
aaacccagtctgggagtgagatgaagaaatttttgagcaccttaactatagatggtgtaacccggagt
gaccaaggattgtacacctgtgcagcatccagtgggctgatgaccaagaagaacagcacatttgtcag
ggtccatgaaaaagacaaaactcacacatgccaccgtgcccagcacctgaactcctgggggaccgt
```

-continued cagtcttcctcttcccccaaaacccaaggacaccctcatgatctcccggacccctgaggtcacatgc
gtggtggtggacgtgagccacgaagaccctgaggtcaagttcaactggtacgtggacggcgtggaggt
gcataatgccaagacaaagccgcgggaggagcagtacaacagcacgtaccgtgtggtcagcgtcctca
ccgtcctgcaccaggactggctgaatggcaaggagtacaagtgcaaggtctccaacaaagccctccca
gcccccatcgagaaaaccatctccaaagccaaagggcagccccgagaaccacaggtgtacaccctgcc
cccatcccgggatgagctgaccaagaaccaggtcagcctgacctgcctggtcaaaggcttctatccca
gcgacatcgccgtggagtgggagagcaatgggcagccggagaacaactacaagaccacgcctcccgtg
ctggactccgacggctccttcttcctctacagcaagctcaccgtggacaagagcaggtggcagcaggg
gaacgtcttctcatgctccgtgatgcatgaggctctgcacaaccactacacgcagaagagcctctccc
tgtctccgggt (SEQ ID NO: 8)
mvsywdtgvllcallsclllltgsssgsdtgrpfvemyseipeiihmtegrelvipcrvtspnitvtlk
kfpldtlipdgkriiwdsrkgfiisnatykeiglltceatvnghlyktnylthrqtntiidvvlspsh
gielsvgeklvlnctartelnvgidfnweypsskhqhkklvnrdlktqsgsemkkflstltidgvtrs
dqglytcaassglmtkknstfvrvhekdkthtcppcpapellggpsvflfppkpkdtlmisrtpevtc
vvvdvshedpevkfnwyvdgvevhnaktkpreeqynstyrvvsvltvlhqdwlngkeykckvsnkalp
apiektiskakgqprepqvytlppsrdeltknqvsltclvkgfypsdiavewesngqpennykttppv
ldsdgsfflysklvtdksrwqqgnvfscsvmhealhnhytqkslslspg p874

(SEQ ID NO: 9)
atggactggacctggtctatcctgttcctggtggccgctgcaaccggcacctactccgaggtgcagct
ggtggaatccggcggaggactggtgcagcctggcggctcccctgagactgtcttgcgccgcctccggct
acaccttcaccaactacggcatgaactgggtccgacaggcccctggcaagggactggaatgggtgggc
tggatcaacacctacaccggcgagcccacctacgccgccgacttcaagcggcggttcaccttcagcct
ggacaccagcaagagcaccgcctacctgcagatgaactccctgcgggccgaggacaccgccgtgtact
actgcgccaagtaccccactactacggcagcagccactggtacttcgacgtgtggggccagggcacc
ctggtcaccgtctcctcagcctccaccaagggcccatcggtcttccccctggcaccctcctccaagag
cacctctgggggcacagcggccctgggctgcctggtcaaggactacttccccgaaccggtgacggtgt
cgtggaactcaggcgccctgaccagcggcgtgcacaccttcccggctgtcctacagtcctcaggactc
tactccctcagcagcgtggtgaccgtgccctccagcagcttgggcacccagacctacatctgcaacgt
gaatcacaagcccagcaacaccaaggtggacaagaaagttgagcccaaatcttgtgacaaaactcaca
catgcccaccgtgcccagcacctgaactcctgggggaccgtcagtcttcctcttccccccaaaaccc
aaggacaccctcatgatctcccggacccctgaggtcacatgcgtggtggtggacgtgagccacgaaga
ccctgaggtcaagttcaactggtacgtggacggcgtggaggtgcataatgccaagacaaagccgcggg
aggagcagtacaacagcacgtaccgtgtggtcagcgtcctcaccgtcctgcaccaggactggctgaat
ggcaaggagtacaagtgcaaggtctccaacaaagccctcccagcccccatcgagaaaaccatctccaa
agccaaagggcagccccgagaaccacaggtgtacaccctgcccccatcccgggatgagctgaccaaga
accaggtcagcctgacctgcctggtcaaaggcttctatcccagcgacatcgccgtggagtgggagagc
aatgggcagccggagaacaactacaagaccacgcctcccgtgctggactccgacggctccttcttcct
ctacagcaagctcaccgtggacaagagcaggtggcagcaggggaacgtcttctcatgctccgtgatgc
atgaggctctgcacaaccactacacgcagaagagcctctccctgtctccgggtaaa (SEQ ID NO: 10)
mdwtwsilflvaaatgtysevqlvesggglvqpggslrlscaasgytftnygmnwvrqapgkglewvg
wintytgeptyaadfkrrftfsldtskstaylqmnslraedtavyycakyphyygsshwyfdvwgqgt
lvtvssastkgpsvflplapsskstsggtaalgclvkdyfpepvtvswnsgaltsgvhtfpavlqssgl
yslssvvtvpssslgtqtyicnvnhkpsntkvdkkvepkscdkthtcppcpapellggpsvflfppkp
kdtlmisrtpevtcvvvdvshedpevkfnwyvdgvevhnaktkpreeqynstyrvvsvltvlhqdwln
gkeykckvsnkalpapiektiskakgqprepqvytlppsrdeltknqvsltclvkgfypsdiavewes
ngqpennykttppvldsdgsfflysklvtdksrwqqgnvfscsvmhealhnhytqkslslspgk p875

(SEQ ID NO: 11)
atggacatgcgggtgccagctcagctgctgggactgctgctgctgtggctgcccggcaccagatgcga
catccagatgacccagtcccctccagcctgtccgcctctgtgggcgacagagtgaccatcacctgttt
ccgcctccaggacatcagcaactacctgaactggtatcagcagaagcccggcaaggcccccaaggtg
ctgatctacttccaccagcagcctgcactccggcgtgccctcccggttctccggctccggctccggcac
cgacttcaccctgaccatctccagcctgcagcccgaggacttcgccacctactactgccagcagtaca
gcaccgtgcccggtggaccttcggccagggcaccaaggtggaaatcaagcggaccgtggccgctcccctcc
gtgttcatcttcccaccctccgacgagcagctgaagtccggcaccgctccgtcgtctgcctgctgaa
caacttctaccccgcgaggccaaggtgcagtggaaggtggacaacgccctgcagtccggcaactccc
aggaatccgtcaccgagcaggactccaaggacagcacctactccctgtcctccaccctgaccctgtcc
aaggccgactacgagaagcacaaggtgtacgcctgcgaagtgacccaccagggcctgtccagccccgt
gaccaagtccttcaaccggggcgagtgc (SEQ ID NO: 12)
mdmrvpaqllgllllwlpgtrcdiqmtqspsslsasvgdrvtitcsasqdisnylnwyqqkpgkapkv
liyftsslhsgvpsrfsgsgsgtdftltisslqpedfatyycqqystvpwtfgqgtkveikrtvaaps
vfifppsdeqlksgtasvvcllnnfypreakvqwkvdnalqsgnsqesvteqdskdstyslsstltls
kadyekhkvyacevthqglsspvtksfnrgec p915

(SEQ ID NO: 13)
atggactggacctggtctatcctgttcctggtggccgctgcaaccggcacctactccgaggtgcagct
ggtggaatccggcggaggactggtgcagcctggcggctcccctgagactgtcttgcgccgcctccggct
acgacttcacccactacggcatgaactgggtccgacaggcccctggcaagggactggaatgggtgggc
tggatcaacacctacaccggcgagcccacctacgccgccgacttcaagcggcggttcaccttcagcct
ggacaccagcaagagcaccgcctacctgcagatgaactccctgcgggccgaggacaccgccgtgtact
actgcgccaagtaccccactactacggcaccagccactggtacttcgacgtgtggggccagggcacc -continued

```
ctggtcaccgtctcctcagcctccaccaagggcccatcggtcttcccctggcaccctcctccaagag
cacctctggggcacagcggccctgggctgcctggtcaaggactacttccccgaaccggtgacggtgt
cgtggaactcaggcgccctgaccagcggcgtgcacaccttcccggctgtcctacagtcctcaggactc
tactccctcagcagcgtggtgaccgtgccctccagcagcttgggcacccagacctacatctgcaacgt
gaatcacaagcccagcaacaccaaggtggacaagaaagttgagcccaaatcttgtgacaaaactcacc
tg
```

(SEQ ID NO: 14)
mdwtwsilflvaaatgtysevqlvesgggvqpggslrlscaasgydfthygmnwvrqapgkglewvg
wintytgeptyaadfkrrftfsldtskstaylqmnslraedtavyycakypyyygtshwyfdvwgqgt
lvtvssastkgpsvfplapsskstsggtaalgclvkdyfpepvtvswnsgaltsgvhtfpavlqssgl
yslssvvtvpssslgtqtyicnvnhkpsntkvdkkvepkscdkthl p914

(SEQ ID NO: 15)
```
atggacatgcgggtgccagctcagctgctgggactgctgctgctgtggctgcccggcaccagatgcga
catccagctgacccagtccccctccagcctgtccgcctctgtgggcgacagagtgaccatcacctgtt
ccgcctcccaggacatcagcaactacctgaactggtatcagcagaagcccggcaaggccccaaggtg
ctgatctacttcaccagcagcctgcactccggcgtgccctcccggttctccggctccggctccggcac
cgacttcaccctgaccatctccagcctgcagcccgaggacttcgccacctactactgccagcagtaca
gcaccgtgcccggaccttcggccagggcaccaaggtggaaatcaagcggaccgtggccgctccctcc
gtgttcatcttcccaccctccgacgagcagctgaagtccggcaccgcctccgtcgtctgcctgctgaa
caacttctaccccgcgaggcaaggtcagtggaaggtggacaacgccctgcagtccggcaactccc
aggaatccgtcaccgagcaggactccaaggacagcacctactccctgtcctccaccctgaccctgtcc
aaggccgactacgagaagcacaaggtgtacgcctgcgaagtgacccaccagggcctgtccagccccgt
gaccaagtccttcaaccggggcgagtgc
```

(SEQ ID NO: 16)
mdmrvpaqllglllllwlpgtrcdiqltqspsslsasvgdrvtitcsasqdisnylnwyqqkpgkapv
liyftsslhsgvpsrfsgsgsgtdftltisslqpedfatyycqqystvpwtfgqgtkveikrtvaaps
vfifppsdeqlksgtasvvcllnnfypreakvqwkvdnalqsgnsqesvteqdskdstyslsstltls
kadyekhkvyacevthqglsspvtksfnrgec p916

(SEQ ID NO: 17)
```
atggactggacctggtctatcctgttcctggtggccgctgcaacggcacctactccgaggtgcagct
ggtggaatccggcggaggactggtgcagcctggcggctccctgagactgtcttgcgccgcctccggct
acgacttcacccactacggcatgaactgggtccgacaggcccctggcaagggactggaatgggtgggc
tggatcaacacctacaccggcgagcccacctacgccgccgacttcaagcggcggttcaccttcagcct
ggacaccagcaagagcaccgcctacctgcagatgaactccctgcgggccgaggacaccgccgtgtact
actgcgccaagtaccccactactacggcaccagccactggtacttcgacgtgtggggccagggcacc
ctggtcaccgtctcctcagcctccaccaagggcccatcggtcttcccctggcaccctcctccaagag
cacctctggggcacagcggccctgggctgcctggtcaaggactacttccccgaaccggtgacggtgt
cgtggaactcaggcgccctgaccagcggcgtgcacaccttcccggctgtcctacagtcctcaggactc
tactccctcagcagcgtggtgaccgtgccctccagcagcttgggcacccagacctacatctgcaacgt
gaatcacaagcccagcaacaccaaggtggacaagaaagttgagcccaaatcttgtgacaaaactcaca
catgcccaccgtgcccagcacctgaactcctgggggaccgtcagtcttcctcttccccccaaaaccc
aaggacaccctcatgatctcccggacccctgaggtcacatgcgtggtggtggacgtgagccacgaaga
ccctgaggtcaagttcaactggtacgtggacggcgtggaggtgcataatgccaagacaaagccgcggg
aggagcagtacaacagcacgtaccgtgtggtcagcgtcctcaccgtcctgcaccaggactggctgaat
ggcaaggagtacaagtgcaaggtctccaacaaagccctcccagcccccatcgagaaaaccatctccaa
agccaaagggcagccccgagaaccacaggtgtacaccctgcccccatcccgggatgagctgaccaaga
accaggtcagcctgacctgcctggtcaaaggcttctatcccagcgacatcgccgtggagtgggagagc
aatgggcagccggagaacaactacaagaccacgcctcccgtgctggactccgacggctccttcttcct
ctacagcaagctcaccgtggacaagagcaggtggcagcagggaacgtcttctcatgctccgtgatgc
atgaggctctgcacaaccactacacgcagaagagcctctccctgtctccgggtaaa
```

(SEQ ID NO: 18)
mdwtwsilflvaaatgtysevqlvesgggvqpggslrlscaasgydfthygmnwvrqapgkglewvg
wintytgeptyaadfkrrftfsldtskstaylqmnslraedtavyycakypyyygtshwyfdvwgqgt
lvtvssastkgpsvfplapsskstsggtaalgclvkdyfpepvtvswnsgaltsgvhtfpavlqssgl
yslssvvtvpssslgtqtyicnvnhkpsntkvdkkvepkscdkthtcppcpapellggpsvflfppkp
kdtlmisrtpevtcvvvdvshedpevkfnwyvdgvevhnaktkpreeqynstyrvvsvltvlhqdwln
gkeykckvsnkalpapiektiskakgqprepqvytlppsrdeltknqvsltclvkgfypsdiavewes
ngqpennykttppvldsdgsfflyskltvdksrwqqgnvfscsvmhealhnhytqkslslspgk p917

(SEQ ID NO: 21)
```
atggtcagctactgggacaccgggtcctgctgtgcgcgctgctcagctgtctgcttctcacaggatc
tagttcaggttcgcgaagtgatacaggtagacctttcgtagagatgtacagtgaaatccccgaaatta
tacacatgactgaaggaagggagctcgtcattccctgccgggttacgtcacctaacatcactgttact
ttaaaaaagtttccacttgacactttgatccctgatggaaaacgcataatctgggacagtagaaaggg
cttcatcatatcaaatgcaacgtacaaagaaatagggcttctgacctgtgaagcaacagtcaatggc
atttgtataagacaaactatctcacacatcgacaaaccaatacaatcatcgatgtggttctgagtccg
tctcatggaattgaactatctgttggagaaaagcttgtcttaaattgtacagcaagaactgaactaaa
tgtgggattgacttcaactgggaataccttcttcgaagcatcagcataagaaactgaaaaccgaa
acctaaaaacccagtctgggagtgagataagaaattttttgagcaccttaactatagatggtaacc
cggagtgaccaaggattgtacacctgtgcagcatccagtgggctgatgaccaagaagaacagcacatt
tgtcagggtccatgaaaaagacaaaactcacacatgcccaccgtgcccagcacctgaactcctggggg
gaccgtcagtcttcctcttccccccaaaacccaaggacaccctcatgatctcccggacccctgaggtc
acatgcgtggtggtggacgtgagccacgaagaccctgaggtcaagttcaactggtacgtggacggcgt
```

-continued ggaggtgcataatgccaagacaaagccgcgggaggagcagtacaacagcacgtaccgtgtggtcagcg
tcctcaccgtcctgcaccaggactggctgaatggcaaggagtacaagtgcaaggtctccaacaaagcc
ctcccagccccatcgagaaaaccatctccaaagccaaagggcagccccgagaaccacaggtgtacac
cctgcccccatcccgggatgagctgaccaagaaccaggtcagcctgacctgcctggtcaaaggcttct
atcccagcgacatcgccgtggagtgggagagcaatgggcagccggagaacaactacaagaccacgcct
cccgtgctggactccgacggctccttcttcctctacagcaagctcaccgtggacaagagcaggtggca
gcaggggaacgtcttctcatgctccgtgatgcatgaggctctgcacaaccactacacgcagaagagcc
tctccctgtctccgggt (SEQ ID NO: 22)
mvsywdtgvllcallsclllltgsssgsrsdtgrpfvemyseipeiihmtegrelvipcrvtspnitvt
lkkfpldtlipdgkriiwdsrkgfiisnatykeiglltceatvnghlyktnylthrqtntiidvvlsp
shgielsvgeklvlnctartelnvgidfnweypsskhqhkklvnrdlktqsgsemkkflstltidgvt
rsdqglytcaassglmtkknstfvrvhekdkthtcppcpapellggpsvflfppkpkdtlmisrtpev
tcvvvdvshedpevkfnwyvdgvevhnaktkpreeqynstyrvvsvltvlhqdwlngkeykckvsnka
lpapiektiskakgqprepqvytlppsrdeltknqvsltclvkgfypsdiavewesngqpennykttp
pvldsdgsfflyskltvdksrwqqgnvfscsvmhealhnhytqkslslspg p964

(SEQ ID NO: 23)
atgcggcttccgggtgcgatgccagctctggccctcaaaggcgagctgctgttgctgtctctcctgtt
acttctggaaccacagatctctcagggcctggtcgtcacaccccgggccagagcttgtcctcaatg
tctccagcaccttcgttctgacctgctcggggttcagctccggtggtgtgggaacggatgtcccaggag
cccccacaggaaatggccaaggcccaggatggcaccttctccagcgtgctcacactgaccaacctcac
tggggctagacacgggagaatacttttgcacccacaatgactcccgtggactggagaccgatgagcgga
aacggctctacatctttgtgccagatcccaccgtgggcttcctccctaatgatgccgaggaactattc
atctttctcacggaaataactgagatcaccattccatgccgagtaacagacccacagctggtggtgac
actgcacgagaagaaggggacgttgcactgcctgtccctatgatcaccaacgtggcttttctggta
tctttgaggacagaagctacatctgcaaaaccaccattggggacaggaggtggattctgatgcctac
tatgtctacagactccaggtgtcatccatcaacgtctctgtgaacgcagtgcagactgtggtccgcca
gggtgagaacatcaccctcatgtgcattgtgatcgggaatgaggtggtcaacttcgagtggacatacc
cccgcaaagaaagtgggcggctggtggagccggtgactgacttcctcttggatatgccttaccacatc
cgctccatcctgcacatccccagtgccgagttagaagactcggggacctacacctgcaatgtgacgga
gagtgtgaatgaccatcaggatgaaaaggccatcaacatcaccgtggttgagagcggctacgtgcggc
tcctgggagaggtgggcacactacaatttgctgagctgcataagttgagagccacctgacagtgggga
acagacagtccgctgtcgtggccggggcatgcccagccgaacatcatctggtctgcctgcagagacc
tcaaaaggtgtccacgtgagctgccgcccacgctgctggggaacagttccgaagaggagagccagctg
gagactaacgtgacgtactgggaggaggagcaggagtttgaggtggtgagcacactgcgtctgcagca
cgtggatcggccactgtcggtgcgctgcacgctgcgcaacgctgagttgtgggccaggacacgcaggagtca
tcgtggtgccacactccttgcccttcaagcccccatgcccatcatgcccagcacctgagttcctgggg
ggaccatcagtcttcctgttccccccaaaaccaaggacactctcatgatctcccggacccctgaggt
cacgtgcgtggtggtggacgtgagccaggaagaccccgaggtccagttcaactggtacgtggatggcg
tggaggtgcataatgccaagacaaagccgcgggaggagcagttcaacagcacgtaccgtgtggtcagc
gtcctcaccgtcctgcaccaggactggctgaacggcaaggagtacaagtgcaaggtctccaacaaagg
cctcccgtcctccatcgagaaaaccatctccaaagccaaagggcagccccgagagccacaggtgtaca
ccctgcccccatcccaggaggagatgaccaagaaccaggtcagcctgacctgcctggtcaaaggcttc
taccccagcgacatcgccgtggagtgggagagcaatgggcagccggagaacaactacaagaccacgcc
tcccgtgctggactccgacggctccttcttcctctacagcaggctaaccgtggacaagagcaggtggc
aggagggaatgtcttctcatgctccgtgatgcatgaggctctgcacaaccactacacacagaagagc
ctctccctgtctctgggtaaa (SEQ ID NO: 24)
mrlpgampalalkgellllslllllepqisqglvvtppgpelvlnvsstfvltcsgsapvvwermsqe
ppqemakaqdgtfssvltltnltgldtgeyfcthndsrgletderkrlyifvpdptvgflpndaeelf
iflteiteitipcrvtdpqlvvtlhekkgdvalpvpydhqrgfsgifedrsyicktttigdrevdsday
yvyrlqvssinsvnavqtvvrqgenitlmcivignevvnfewtyprkesgrlvepvtdflldmpyhi
rsilhipsaeledsgtytcnvtesvndhqdekainitvvesgyvrllgevgtlqfaelhrsrtlqvvf
eayppptvlwfkdnrtlgdssageialstrnvsetryvseltlvrvkvaeaghytmrafhedaevqls
fqlqinvpvrvlseseshpdsgeqtvrcrgrgmpqpniiwsacrdlkrcprelppptllgnsseeesql
etnvtyweeeqefevvstlrlqhvdrplsvrctlrnavgqdtglnvvphslpfkppcpscpapeflg
gpsvflfppkpkdtlmisrtpevtcvvvdvsqedpevqfnwyvdgvevhnaktkpreeqfnstyrvvs
vltvlhqdwlngkeykckvsnkglpssiektiskakgqprepqvytlppsqeemtknqvsltclvkgf
ypsdiavewesngqpennykttppvldsdgsfflysrltvdksrwqegnvfscsvmhealhnhytqks
lslslgk p963

(SEQ ID NO: 25)
atgcggcttccgggtgcgatgccagctctggccctcaaaggcgagctgctgttgctgtctctcctgtt
acttctggaaccacagatctctcagggcctggtcgtcacaccccgggccagagcttgtcctcaatg
tctccagcaccttcgttctgacctgctcggggttcagctccggtggtgtgggaacggatgtcccaggag
cccccacaggaaatggccaaggcccaggatggcaccttctccagcgtgctcacactgaccaacctcac
tggggctagacacgggagaatacttttgcacccacaatgactcccgtggactggagaccgatgagcgga
aacggctctacatctttgtgccagatcccaccgtgggcttcctccctaatgatgccgaggaactattc
atctttctcacggaaataactgagatcaccattccatgccgagtaacagacccacagctggtggtgac
actgcacgagaagaaggggacgttgcactgcctgtccctatgatcaccaacgtggcttttctggta
tctttgaggacagaagctacatctgcaaaaccaccattggggacaggaggtggattctgatgcctac
tatgtctacagactccaggtgtcatccatcaacgtctctgtgaacgcagtgcagactgtggtccgcca -continued

```
gggtgagaacatcaccctcatgtgcattgtgatcgggaatgaggtggtcaacttcgagtggacatacc
cccgcaaagaaagtgggcggctggtggagccggtgactgacttcctcttggatatgccttaccacatc
cgctccatcctgcacatccccagtgccgagttagaagactcgggggacctacacctgcaatgtgacgga
gagtgtgaatgaccatcaggatgaaaaggccatcaacatcaccgtggttgagagcggctacgtgcggc
tcctgggagaggtgggcacactacaatttgctgagctgcatcggagccggacactgcaggtagtgttc
gaggcctacccaccgcccactgtcctgtggttcaaagacaaccgcaccctgggcgactccagcgctgg
cgaaatcgccctgtccacgcgcaacgtgtcggagacccggtatgtgtcagagctgacactggttcgcg
tgaaggtggcagaggctggccactacaccatgcgggccttccatgaggatgctgaggtccagctctcc
ttccagctacagatcaatgtccctgtccgagtgctggagctaagtgagagccaccctgacagtgggga
acagacagtccgctgtcgtggccggggcatgcccagccgaacatcatctggtctgcctgcagagacc
tcaaaaggtgtccacgtgagctgccgcccacgctgctggggaacagttccgaagaggagagccagctg
gagactaacgtgacgtactgggaggaggagcaggagtttgaggtggtgagcacactgcgtctgcagca
cgtggatcggccactgtcggtgcgctgcacgctgcgcaacgctgtgggccaggacacgcaggaggtca
tcgtggtgccacactccttgcccttcaaggaccccgagcccaaatcttgtgacaaaactcacacatgc
ccaccgtgcccagcacctgaactcctgggggaccgtcagtcttcctcttccccccaaaacccaagga
caccctcatgatctcccggacccctgaggtcacatgcgtggtggtggacgtgagccacgaagaccctg
aggtcaagttcaactggtacgtggacggcgtggaggtgcataatgccaagacaaagccgcgggaggag
cagtacaacagcacgtaccgtgtggtcagcgtcctcaccgtcctgcaccaggactggctgaatggcaa
ggagtacaagtgcaaggtctccaacaaagccctcccagcccccatcgagaaaaccatctccaaagcca
aagggcagccccgagaaccacaggtgtacaccctgcccccatcccgggatgagctgaccaagaaccag
gtcagcctgacctgcctggtcaaaggcttctatcccagcgacatcgccgtggagtgggagagcaatgg
gcagccggagaacaactacaagaccacgcctcccgtgctggactccgacggctccttcttcctctaca
gcaagctcaccgtggacaagagcaggtggcagcaggggaacgtcttctcatgctccgtgatgcatgag
gctctgcacaaccactacacgcagaagagcctctccctgtctccgggtaaa
```

(SEQ ID NO: 26)

```
mrlpgampalalkgellllslllllepqisqglvvtppgpelvlnvsstfvltcsgsapvvwermsqe
ppqemakaqdgtfssvltltnltgldtgeyfcthndsrgletderkrlyifvpdptvgflpndaeelf
iflteiteitipcrvtdpqlvvtlhekkgdvalpvpydhqrgfsgifedrsyickttigdrevdsday
yvyrlqvssinvsvnavqtvvrqgenitlmcivignevvnfewtyprkesgrlvepvtdflldmpyhi
rsilhipsaeledsgtytcnvtesvndhqdekainitvvesgyyvrllgevgtlqfaelhrsrtlqvvf
eayppptvlwfkdnrtlgdssageialstrnvsetryvseltlvrvkveaghytmrafhedaevqls
fqlqinvpvrvleseshpdsgeqtvrcrgrgmpqpniiwsacrdlkrcprelpptllgnsseeesql
etnvtyweeeqefevvstlrlqhvdrplsvrctlrnavgqdtqevivvphslpfkdpepkscdkthtc
ppcpapellggpsvflfppkpkdtlmisrtpevtcvvvdvshedpevkfnwyvdgvevhnaktkpree
qynstyrvvsvltvlhqdwlngkeykckvsnkalpapiektiskakgqprepqvytlppsrdeltknq
vsltclvkgfypsdiavewesngqpennykttppvldsdgsfflyskltvdksrwqqgnvfscsvmhe
alhnhytqkslslspgk
``` p974

(SEQ ID NO: 27)

```
atgcggcttccgggtgcgatgccagctctggccctcaaaggcgagctgctgttgctgtctcctgtt
acttctggaaccacagatctctcagggcctggtcgtcacaccccggggccagagcttgtcctcaatg
tctccagcaccttcgttctgacctgctcggggttcagctccggtggtgtgggaacggatgtcccaggag
ccccacaggaaatggccaaggcccaggatggcaccttctccgacgtgctcacactgaccaacctcac
tgggctagacacgggagaatactttttgcacccacaatgactcccgtggactggagaccgatgagcgga
aacggctctacatctttgtgccagatcccaccgtgggcttcctccctaatgatgccgaggaactattc
atctttctcacggaaataactgagatcaccattccatgccgagtaacagaccccacagctggtggtgac
actgcacgagaagaaggggacgttgcactgcctgtccctatgatcaccaacgtggcttttctggta
tctttgaggacagaagctacatctgcaaaaccaccattggggacaggaggtggattctgatgcctac
tatgtctacagactccaggtgtcatccatcaacgtctctgtgaacgcagtgcagactgtggtccgcca
gggtgagaacatcaccctcatgtgcattgtgatcgggaatgaggtggtcaacttcgagtggacatacc
cccgcaaagaaagtgggcggctggtggagccggtgactgacttcctcttggatatgccttaccacatc
cgctccatcctgcacatccccagtgccgagttagaagactcgggggacctacacctgcaatgtgacgga
gagtgtgaatgaccatcaggatgaaaaggccatcaacatcaccgtggttgagagcggctacgtgcggc
tcctgggagagcccaaatcttgtgacaaaactcacacatgcccaccgtgcccagcacctgaactcctg
ggggaccgtcagtcttcctcttccccccaaaacccaaggacaccctcatgatctcccggacccctga
ggtcacatgcgtggtggtggacgtgagccacgaagaccctgaggtcaagttcaactggtacgtggacg
gcgtggaggtgcataatgccaagacaaagccgcgggaggagcagtacaacagcacgtaccgtgtggtc
agcgtcctcaccgtcctgcaccaggactggctgaatggcaaggagtacaagtgcaaggtctccaacaa
agccctcccagcccccatcgagaaaaccatctccaaagccaaagggcagccccgagaaccacaggtgt
acaccctgcccccatcccgggatgagctgaccaagaaccaggtcagcctgacctgcctggtcaaaggc
ttctatcccagcgacatcgccgtggagtgggagagcaatgggcagccggagaacaactacaagaccac
gcctcccgtgctggactccgacggctccttcttcctctacagcaagctcaccgtggacaagagcaggt
ggcagcaggggaacgtcttctcatgctccgtgatgcatgaggctctgcacaaccactacacgcagaag
agcctctccctgtctccgggtaaa
```

(SEQ ID NO: 28)

```
mrlpgampalalkgellllslllllepqisqglvvtppgpelvlnvsstfvltcsgsapvvwermsqe
ppqemakaqdgtfssvltltnltgldtgeyfcthndsrgletderkrlyifvpdptvgflpndaeelf
iflteiteitipcrvtdpqlvvtlhekkgdvalpvpydhqrgfsgifedrsyickttigdrevdsday
yvyrlqvssinvsvnavqtvvrqgenitlmcivignevvnfewtyprkesgrlvepvtdflldmpyhi
rsilhipsaeledsgtytcnvtesvndhqdekainitvvesgyvrllgepkscdkthtcppcpapell
```

-continued ggpsvflfppkpkdtlmisrtpevtcvvvdvshedpevkfnwyvdgvevhnaktkpreeqynstyrvv
svltvlhqdwlngkeykckvsnkalpapiektiskakgqprepqvytlppsrdeltknqvsltclvkg
fypsdiavewesngqpennykttppvldsdgsfflyskltvdksrwqqgnvfscsvmhealhnhytqk
slslspgk p978

(SEQ ID NO: 29)
atgcggcttccgggtgcgatgccagctctggccctcaaaggcgagctgctgttgctgtctcctgtt
acttctggaaccacagatctctcagggcctggtcgtcacaccccggggccagagcttgtcctcaatg
tctccagcaccttcgttctgacctgctcgggttcagctccggtggtgtgggaacggatgtcccaggag
cccccacaggaaatggccaaggcccaggatggcaccttctccagcgtgctcacactgaccaacctcac
tgggctagacacgggagaatacttttgcacccacaatgactcccgtggactggagaccgatgagcgga
aacggctctacatctttgtgccagatcccaccgtgggcttcctccctaatgatgccgaggaactattc
atctttctcacggaaataactgagatcaccattccatgccgagtaacagacccacagctggtggtgac
actgcacgagaagaaggggacgttgcactgcctgtccctatgatcaccaacgtggcttttctggta
tctttgaggacagaagctacatctgcaaaaccaccattggggacagggaggtggattctgatgcctac
tatgtctacagactccaggtgtcatccatcaacgtctctgtgaacgcagtgcagactgtggtccgcca
gggtgagaacatcaccctcatgtgcattgtgatcgggaatgaggtggtcaacttcgagtggacatacc
cccgcaaagaaagtgggcggctggtggagccggtgactgacttcctcttggatatgccttaccacatc
cgctccatcctgcacatccccagtgccgagttagaagactcggggacctacacctgcaatgtgacgga
gagtgtgaatgaccatcaggatgaaaaggccatcaacatcaccgtggttgagagcggctacgtgcggc
tcctgggagaggtgggcacactacaatttgctgagctgcatcggagccggacactgcaggtagtgttc
gaggcctacccaccgcccactgtcctgtggttcaaagacaaccgcaccctgggcgactccagcgctgg
cgaaatcgccctgtccacgcgcaacgtgtcggagacccggtatgtgtcagagctgacactggttcgcg
tgaaggtggcagaggctggccactacaccatgcgggccttccatgaggatgctgaggtccagctctcc
ttccagctacagatcaatgtccctgtccgagtgctggagctaagtgagagccaccctgacagtgggga
acagacagtccgctgtcgtggccggggcatgccccagccgaacatcatctggtctgcctgcagagacc
tcaaaaggtgtccacgtgagctgccgcccacgctgctgggaacagttccgaagaggagagccagctg
gagactaacgtgacgtactgggaggaggagcaggagtttgaggtggtgagcacactgcgtctgcagca
cgtggatcggccactgtcggtgcgctgcacgctgcgcaacgctgtgggccaggacacgcaggaggtca
tcgtggtgccacactccttgcccttcaag (SEQ ID NO: 30)
mrlpgampalalkgellllslllllepqisqglvvtppgpelvlnvsstfvltcsgsapvvwermsqe
ppqemakaqdgtfssvltltnltgldtgeyfcthndsrgletderkrlyifvpdptvgflpndaeelf
iflteiteitipcrvtdpqlvvtlhekkgdvalpvpydhqrgfsgifedrsyickttigdrevdsday
yvyrlqvssinvsvnavqtvvrqgenitlmcivignevvnfewtyprkesgrlvepvtdflldmpyhi
rsilhipsaeledsgtytcnvtesvndhqdekainitvvesgyvrllgevgtlqfaelhrsrtlqvvf
eaypppptvlwfkdnrtlgdssageialstrnvsetryvseltlvrvkvaeaghytmrafhedaevqls
fqlqinvpvrvleleseshpdsgeqtvrcrgrgmpqpniiwsacrdlkrcprelppttllgnsseeesql
etnvtyweeeqefevvstlrlqhvdrplsvrctlrnavgqdtqevivvphslpfk p977

(SEQ ID NO: 31)
atggggcagtgcaggaaaagtggcactatgaaccctgcagccctagacaattgtactaaccttcttct
cttcctctcctgacaggttggtgtacagtagcttccaagtactccaccatgcggcttccgggtgcga
tgccagctctggccctcaaaggcgagctgctgttgctgtctctcctgttacttctggaaccacagatc
tctcagggcctggtcgtcacaccccggggccagagcttgtcctcaatgtctccagcaccttcgttct
gacctgctcgggttcagctccggtggtgtgggaacggatgtcccaggagcccccacaggaaatggcca
aggcccaggatggcaccttctccagcgtgctcacactgaccaacctcactgggctagacacgggagaa
tactttgcacccacaatgactcccgtggactggagaccgatgagcggaaacggctctacatctttgt
gccagatcccaccgtgggcttcctccctaatgatgccgaggaactattcatctttctcacggaaataa
ctgagatcaccattccatgccgagtaacagacccacagctggtggtgacactgcacgagaagaaaggg
gacgttgcactgcctgtccctatgatcaccaacgtggcttttctggtatctttgaggacagaagcta
catctgcaaaaccaccattggggacagggaggtggattctgatgcctactatgtctacagactccagg
tgtcatccatcaacgtctctgtgaacgcagtgcagactgtggtccgccagggtgagaacatcaccctc
atgtgcattgtgatcgggaatgaggtggtcaacttcgagtggacataccccgcaaagaaagtgggcg
gctggtggagccggtgactgacttcctcttggatatgccttaccacatccgctccatcctgcacatcc
ccagtgccgagttagaagactcggggacctacacctgcaatgtgacggagagtgtgaatgaccatcag
gatgaaaaggccatcaacatcaccgtggttgagagcggctacgtgcggctcctgggagaggtgggcac
actacaatttgctgagctgcatcggagccggacactgcaggtagtgttcgaggcctacccaccgccca
ctgtcctgtggttcaaagacaaccgcaccctgggcgactccagcgctggcgaaatcgccctgtccacg
cgcaacgtgtcggagacccggtatgtgtcagagctgacactggttcgcgtgaaggtggcagaggctgg
ccactacaccatgcgggccttccatgaggatgctgaggtccagctctccttccagctacagatcaatg
tccctgtccgagtgctggagctaagtgagagccaccctgacagtggggaacagacagtccgctgtcgt
ggccggggcatgccccagccgaacatcatctggtctgcctgcagagacctcaaaaggtgtccacgtga
gctgccgcccacgctgctgggaacagttccgaagaggagagccagctggagactaacgtgacgtact
gggaggaggagcaggagtttgaggtggtgagcacactgcgtctgcagcacgtggatcggccactgtcg
gtgcgctgcacgctgcgcaacgctgtgggccaggacacgcaggaggtcatcgtggtgccacactcttt
gcccttcaagcggggcagccaccaccaccaccac (SEQ ID NO: 32)
mgqcrksgtmnpaaldnctnlllfplltgwctvaskystmrlpgampalalkgellllslllllepqi
sqglvvtppgpelvlnvsstfvltcsgsapvvwermsqeppqemakaqdgtfssvltltnltgldtge
yfcthndsrgletderkrlyifvpdptvgflpndaeelfiflteiteitipcrvtdpqlvvtlhekkg
dvalpvpydhqrgfsgifedrsyickttigdrevdsdayyvyrlqvssinvsvnavqtvvrqgenitl
mcivignevvnfewtyprkesgrlvepvtdflldmpyhirsilhipsaeledsgtytcnvtesvndhq
dekainitvvesgyvrllgevgtlqfaelhrsrtlqvvfeaypppptvlwfkdnrtlgdssageialst
rnvsetryvseltlvrvkvaeaghytmrafhedaevqlsfqlqinvpvrvleleseshpdsgeqtvrcr
grgmpqpniiwsacrdlkrcprelppttllgnsseeesqletnvtyweeeqefevvstlrlqhvdrpls
vrctlrnavgqdtqevivvphslpfkrgshhhhhh In other examples, the one or more biologically active molecules are selected from the group consisting of C3a inhibitors, C3b inhibitors, other agents targeting and inhibiting or modulating immunologic pathway molecules, brain derived neurotrophic factor (BDNF), NT-4, ciliary neurotrophic factor (CNTF), Axokine, basic fibroblast growth factor (bFGF), insulin-like growth factor I (IGF I), insulin-like growth factor II (IGF II), acid fibroblast growth factor (aFGF), epidermal growth factor (EGF), transforming growth factor α (TGF α), transforming growth factor β (TGF β), nerve growth factor (NGF), platelet derived growth factor (PDGF), glia-derived neurotrophic factor (GDNF), Midkine, phorbol 12-myristate 13-acetate, tryophotin, activin, thyrotropin releasing hormone, interleukins, bone morphogenic protein, macrophage inflammatory proteins, heparin sulfate, amphiregulin, retinoic acid, tumor necrosis factor α, fibroblast growth factor receptor, epidermal growth factor receptor (EGFR), PEDF, LEDGF, NTN, Neublastin, neurotrophins, lymphokines, VEGF inhibitors, PDGF inhibitors, PlGF inhibitors, Tie2, CD55, C59, a bispecific molecule that simultaneously binds VEGF and PDGF, and other agents expected to have therapeutically useful effects on potential target tissues.

Known anti-VEGF compounds can include, but are not limited to, anti-VEGF receptor fragments (i.e., Aflibercept) and/or anti-VEGF antibodies (or antigen binding fragments thereof) (i.e., Bevacizumab, DrugBank DB00112; or Ranibizumab DrugBank DB01270). The sequences of these known anti-VEGF compounds are known in the art.

The one or more biologically active molecules can be C3a inhibitors, C3b inhibitors, VEGF inhibitors, PDGF inhibitors, or any combinations thereof.

The methods and devices are intended for use in a primate, for example, a human host, recipient, patient, subject or individual. A number of different implantation sites are contemplated for the devices and methods. Suitable implantation sites include, but are not limited to, eye, spleen, ear, heart, colon, liver, kidney, breast, joint, bone marrow, subcutaneous, and/or peritoneal spaces. For example, implantation sites include the aqueous and vitreous humors of the eye, the periocular space, the anterior chamber, the posterior chamber, and/or the Subtenon's capsule. Within the body, implantation sites may include subcutaneous or intraperitoneal. In addition, implantation may be directed at localized delivery at or near lesions requiring the desired biologic therapy. Example of such disease sites may be inflamed joints or sites of benign or malignant tumors. Access by the device to the circulatory system can further extend the range of potential disease sites within the body to distally affected organs and tissues.

Any of the devices can be used to deliver an appropriate therapeutic dose of the one or more biologically active molecules to an implantation site described herein.

The devices are also able to deliver an appropriate therapeutic dosage of the one or more biologically active molecules for at least 6 months (e.g., at least 6, 7, 8, 9, 10, 11, 12, 13, 14, 15, 16, 17, 18, 19, 20, 21, 22, 23, 24, or more months).

Early generation ECT products producing soluble VEGF-receptor (VEGF-R) (e.g., single chambered NT-503 second generation ECT devices) have been shown to deliver the biologically active molecule for at least 6 months (e.g., at least 6, 7, 8, 9, 10, 11, 12, 13, 14, 15, 16, 17, 18, 19, 20, 21, 22, 23, 24, or more months) and have demonstrated clinically meaningful improvements in BCVA and reductions in macular thickening in patients with active neovascular AMD for over 12 months. Thus, the second generation ECT devices exhibit extended duration delivery of the VEGF-R ECT product.

Likewise, higher dose levels (such as those produced by the ECT cartridge devices described herein) are also expected to achieve efficacy comparable or greater than standard-of-care treatments.

Accordingly, both NT-503 second generation ECT devices and third generation ECT cartridge devices are capable of extended duration (e.g., at least 6, 7, 8, 9, 10, 11, 12, 13, 14, 15, 16, 17, 18, 19, 20, 21, 22, 23, 24, or more months) delivery of ECT products.

The number of devices and device size should be sufficient to produce a therapeutic effect upon implantation and is determined by the amount of biological activity required for the particular application. In the case of secretory cells releasing therapeutic substances, standard dosage considerations and criteria known to the art will be used to determine the amount of secretory substance required. Factors to be considered include the size and weight of the recipient; the productivity or functional level of the cells; and, where appropriate, the normal productivity or metabolic activity of the organ or tissue whose function is being replaced or augmented. It is also important to consider that a fraction of the cells may not survive the immunoisolation and implantation procedures. Moreover, whether the recipient has a preexisting condition that can interfere with the efficacy of the implant must also be considered. Devices can easily be manufactured which contain many thousands of cells. For example, current ophthalmic clinical devices (e.g., the second generation ECT devices) contain between 200,000 and 750,000 cells, whereas micronized devices would contain between 10,000 and 100,000 cells. Other large scale devices (e.g., for systemic applications) may contain between 1,000,000 to 100,000,000 cells.

The therapeutically effective amount used in any devices (i.e., therapeutic dosages) may be between 0.1 pg and 10000 μg (e.g., between 0.1 pg and 5000 μg; between 0.1 pg and 2500 μg; between 0.1 pg and 1000 μg; between 0.1 pg and 500 μg; between 0.1 pg and 250 μg; between 0.1 pg and 100 μg; between 0.1 pg and 50 μg; between 0.1 pg and 25 μg; between 0.1 pg and 10 μg; between 0.1 pg and 5 μg; between 0.1 pg and 100 μg; between 0.1 pg and 50 μg; between 0.1 pg and 25 μg; between 0.1 pg and 10 μg; or between 0.1 pg and 5 ng) per eye per patient per day.

The therapeutically effective amount used in any devices (i.e., therapeutic dosages) may be between 0.1 pg and 10000 μg (e.g., between 0.1 pg and 5000 μg; between 0.1 pg and 2500 μg; between 0.1 pg and 1000 μg; between 0.1 pg and 500 μg; between 0.1 pg and 250 μg; between 0.1 pg and 100 μg; between 0.1 pg and 50 μg; between 0.1 pg and 25 μg; between 0.1 pg and 10 μg; between 0.1 pg and 5 μg; between 0.1 pg and 100 μg; between 0.1 pg and 50 μg; between 0.1 pg and 25 μg; between 0.1 pg and 10 μg; or between 0.1 pg and 5 ng) per patient per day.

In one non-limiting example, the therapeutic amount is at least 0.5-50 μg/ml steady state in the eye. Suitable therapeutic amounts may include, for example, 0.5 μg, 0.6 μg, 0.7 ug, 0.8 μg, 0.9 μg, 1 μg, 2 μg, 3 μg, 4 μg, μg, 6 μg, 7 μg, 8 μg, 9 μg, 10 μg, 11 μg, 12 μg, 13 μg, 14 μg, 15 μg, 16 μg, 17 μg, 18 μg, 19 μg, 20 μg, 21 μg, 22 μg, 23 μg, 24 μg, 25 μg, 26 μg, 27 μg, 28 μg, 29 μg, 30 μg, 31 μg, 32 μg, 33 μg, 34 μg, 35 μg, 36 μg, 37 μg, 38 μg, 39 μg, 40 μg, 41 μg, 42 μg, 43 μg, 44 μg, 45 μg, 46 μg, 47 μg, 48 μg, 49 μg, 50 μg, 51 μg, 52 μg, 53 μg, 54 μg, 55 μg, 56 μg, 57 μg, 58 μg, 59 μg, 60 μg, 61 μg, 62 μg, 63 μg, 64 μg, 65 μg, 66 μg, 67 μg, 68 μg, 69 μg, 70 μg, 71 μg, 72 μg, 73 μg, 74 μg, 75 μg, 76

μg, 77 μg, 78 μg, 79 μg, 80 μg, 81 μg, 82 μg, 83 μg, 84 μg, 85 μg, 86 μg, 87 μg, 88 μg, 89 μg, 90 μg, 91 μg, 92 μg, 93 μg, 94 μg, 95 μg, 96 μg, 97 μg, 98 μg, 99 μg, 100 μg, 150 μg, 200 μg, 250 μg, 300 μg, 350 μg, 400 μg, 450 μg, 500 μg, 550 μg, 600 μg, 650 μg, 700 μg, 750 μg, 800 μg, 850 μg, 900 μg, 950 μg, 1000 μg, 1500 μg, 2000 μg, 2500 μg, 3000 μg, 3500 μg, 4000 μg, 4500 μg, 5000 μg, 5500 μg, 6000 μg, 6500 μg, 7000 μg, 7500 μg, 8000 μg, 8500 μg, 9000 μg, 9500 μg or 10000 μg.

Ophthalmic disorders that may be treated by various embodiments of the present invention include, but are not limited to, branch or central retinal vein occlusion (BRVO or CRVO), uveitis, macular telangiectasia, diabetic retinopathies, diabetic macular edema, proliferative retinopathies, retinal vascular diseases, vascular anomalies, age-related macular degeneration and other acquired disorders, endophthalmitis, infectious diseases, inflammatory but non-infectious diseases, AIDS-related disorders, ocular ischemia syndrome, pregnancy-related disorders, peripheral retinal degenerations, retinal degenerations, toxic retinopathies, retinal tumors, choroidal tumors, choroidal disorders, vitreous disorders, retinal detachment and proliferative vitreoretinopathy, non-penetrating trauma, penetrating trauma, post-cataract complications, and inflammatory optic neuropathies.

Those skilled in the art will recognize that age-related macular degeneration includes, but is not limited to, wet and dry age-related macular degeneration, exudative age-related macular degeneration, and myopic degeneration.

In some embodiments, the disorder to be treated is the wet form of age-related macular degeneration or BRVO or CRVO. The present devices may also be useful for the treatment of ocular neovascularization, a condition associated with many ocular diseases and disorders. For example, retinal ischemia-associated ocular neovascularization is a major cause of blindness in diabetes and many other diseases.

The devices may also be useful for inhibiting endothelial cell proliferation in hematologic disorders, atherosclerosis, inflammation, increased vascular permeability and malignancy.

The devices may also be useful for d treating a variety of disorders selected from the group consisting of ophthalmic disorders, endothelial cell proliferation or vascularization related disorders, cancer, infectious disorders, inflammatory disorders, immunologic disorders, digestive disorders, vascular disorders, lung disorders, oral disorders, blood disorders, liver disorders, skin disorders, prostate disorders, kidney disorders, metabolic disorders, endocrine disorders, neurologic disorders, and neurodegenerative disorders. Determination of suitable therapeutic dosages for use in the treatment of these disorders is within the routine level of skill in the art.

As used herein, the terms "individual" or "recipient" or "host" are used interchangeably to refer to a human or an animal subject.

As used herein, a "biologically active molecule" ("BAM") is any substance that is capable of exerting a biologically useful effect upon the body of an individual in whom a device is implanted. Anti-angiogenic antibody-scaffolds and anti-angiogenic antibodies and molecules are examples of BAMs. BAMs may include immunologic factors or targets, growth factor inhibitors, soluble receptors, anti-angiogenic antibodies and molecules, anti-angiogenic antibody scaffolds, cytokine, growth factors, neurotrophic factors, angiogenic factors, neurotransmitters, hormones, enzymes, anti-inflammatory factors, therapeutic proteins, gene transfer vectors, antibodies and antibody fragments, antigens, peptides, and any combination thereof. In various embodiments, such molecules can include, but are not limited to, C3a inhibitors, C3b inhibitors, other agents targeting and inhibiting or modulating immunologic pathway molecules, brain derived neurotrophic factor (BDNF), NT-4, ciliary neurotrophic factor (CNTF), Axokine, basic fibroblast growth factor (bFGF), insulin-like growth factor I (IGF I), insulin-like growth factor II (IGF II), acid fibroblast growth factor (aFGF), epidermal growth factor (EGF), transforming growth factor α (TGF α), transforming growth factor β (TGF β), nerve growth factor (NGF), platelet derived growth factor (PDGF), glia-derived neurotrophic factor (GDNF), Midkine, phorbol 12-myristate 13-acetate, tryophotin, activin, thyrotropin releasing hormone, interleukins, bone morphogenic protein, macrophage inflammatory proteins, heparin sulfate, amphiregulin, retinoic acid, tumor necrosis factor α, fibroblast growth factor receptor, epidermal growth factor receptor (EGFR), PEDF, LEDGF, NTN, Neublastin, neurotrophins, lymphokines, VEGF inhibitors, PDGF inhibitors, PIGF inhibitors, Tie2, CD55, C59, bispecific molecules the simultaneously bind VEGF and PDGF, and other agents expected to have therapeutically useful effects on potential target tissues. As used herein, one or more biologically active molecules can target one or more (1, 2, 3 or more) same or different specific sites/targets. In some embodiments, the biologically active molecules can be bi-specific molecules, where one delivered molecule could potentially target two distinct sites/receptors.

The terms "cartridge device" and "cartridge" and "NT-503-3" and "third generation ECT device" and "third generation NT-503 ECT device" and the like are used interchangeably herein to refer to the ECT devices described herein.

The terms "second generation ECT device" and "NT-503-2" and "single chamber device" and the like are used interchangeably herein to refer to the "traditional" one-chambered ECT devices that secrete anti-angiogenic antibody scaffolds or molecules that are known in the relevant art.

Unless otherwise specified, the term "cells" means cells in any form, including but not limited to cells retained in tissue, cell clusters, and individually isolated cells.

As used herein, the term "NTC-203-910 cells" and the like refer to parental NTC-200 cells engineered to produce soluble VEGF-receptor protein As used herein, the term "encapsulated NTC cells" refer to any engineered derivation of the parental NTC-200 (ARPE-19) cells engineered to produce a therapeutic molecule (i.e., NTC-201-6A, which are NTC-200 cells engineered to produce high expression of ciliary neurotrophic factor).

As used herein, the term "encapsulated cells" and the like refer to any therapeutic cell lines capable of encapsulation and survival in a "biocompatible capsule" or biocompatible device".

As used herein a "biocompatible capsule" or "biocompatible device" or "biocompatible vehicle" means that the capsule or device or vehicle, upon implantation in an individual, does not elicit a detrimental host response sufficient to result in the rejection of the capsule or to render it inoperable, for example through degradation.

As used herein an "immunoisolatory capsule" or "immunoprotective capsule" or "immunoisolatory device" or "immunoprotective device" or "immunoisolatory vehicle" or "immunoprotective vehicle" means that the capsule upon implantation into an individual, favorably partitions the device cellular contents and minimizes the deleterious effects of the host's immune system on the cells within its core.

As used herein "long-term, stable expression of a biologically active molecule" means the continued production of a biologically active molecule at a level sufficient to maintain its useful biological activity for periods greater than one month, for example greater than three months or greater than six months. Implants of the devices and the contents thereof are able to retain functionality for greater than three months in vivo and in many cases for longer than a year, and in some cases longer than two years or more.

The term "internal scaffold" is one example of a "matrix" that can be used in the devices described herein.

The "semi-permeable" nature of the jacket membrane surrounding the core permits molecules produced by the cells (e.g., metabolites, nutrients and/or therapeutic substances) to diffuse from the device into the surrounding host eye tissue, but is sufficiently impermeable to protect the cells in the core from detrimental immunological attack by the host.

The terms "encapsulated cell therapy" or "ECT" are used interchangeably herein to refer to any device capable of isolating cells from the recipient host's immune system by surrounding the cells with a semipermeable biocompatible material before implantation within the host. Those skilled in the art will recognize that in any of the devices, methods, and/or uses presented herein, elements of any ECT devices known in the art can be employed.

The term "treatment" or "treating" refers to reducing or alleviating symptoms in a subject, preventing symptoms from worsening or progressing, and/or preventing disease in a subject who is free therefrom. For a given subject, improvement in a symptom, its worsening, regression, or progression may be determined by any objective or subjective measure. Efficacy of the treatment may be measured as an improvement in morbidity or mortality (e.g., lengthening of survival curve for a selected population). Thus, effective treatment would include therapy of existing disease, control of disease by slowing or stopping its progression, prevention of disease occurrence, reduction in the number or severity of symptoms, or a combination thereof. The effect may be shown in a controlled study using one or more statistically significant criteria. For example, in some embodiments, treatment refers to inhibiting endothelial cell proliferation or vascularization.

EXAMPLES

Example 1: Multi-Chamber Cartridge Compared to Single Encapsulation Chamber of Equivalent Volume Retinal pigment epithelial cells engineered to produce a soluble VEGF antagonist were cultured and prepared at a density of 50,000 per microliter in a serum-free media. Cells were encapsulated in a cartridge device manufactured with seven chambers each 400 microns inner diameter and 50 micron wall thickness and total length of 8.5 mm. Cells were also encapsulated in a 1.3 mm single chamber device, 8.5 mm in length with an approximate equivalent volume to the chambered device. Both device groups were encapsulated with equivalent cell number, cell volume and rate of cell infusion. Devices were conditioned in culture media for 1 week prior to implant in eyes of New Zealand White rabbits. Cohorts were evaluated prior to implant to determine VEGF antagonist expression using ELISA specific for the soluble VEGF antagonist and viability of the encapsulated cells following histological processing (plastic embedding followed by H&E staining) Both encapsulation device designs resulted in equivalent in vitro release kinetics and cell viability. Expression of VEGF antagonist was between 4000 and 5000 µg/device/day while viability was between 4 and 5 over a scale range of 0 to 5 (0=poor viability and distribution, 5=excellent viability and distribution).

Retinal pigment epithelial cells engineered to produce a soluble VEGF antagonist were cultured and prepared at a density of 50,000 per microliter in a serum-free media. Cells were encapsulated in a cartridge device manufactured with seven chambers each 400 microns inner diameter and 50 micron wall thickness and total length of 8.5 mm. Cells were also encapsulated in a 1.3 mm single chamber device, 8.5 mm in length with an approximate equivalent volume to the chambered device. Both device groups were encapsulated with equivalent cell number, cell volume and rate of cell infusion. Devices were conditioned in culture media for 1 week prior to implant in eyes of New Zealand White rabbits. Cohorts were evaluated prior to implant to determine VEGF antagonist expression using ELISA specific for the soluble VEGF antagonist and viability of the encapsulated cells following histological processing (plastic embedding followed by H&E staining) Both encapsulation device designs resulted in equivalent in vitro release kinetics and cell viability. Expression of VEGF antagonist was between 4000 and 5000 µg/device/day while viability was between 4 and 5 over a scale range of 0 to 5 (0=poor viability and distribution, 5=excellent viability and distribution).

Both groups were implanted over the course of two-week in the rabbit eye, explanted and evaluated again for VEGF antagonist expression and encapsulated cell viability. The results at two-week demonstrated the superiority of the cartridge implant design compared to the single increased diameter design. Expression of VEGF antagonist at 2-week is found in Table 1.

TABLE 1

Expression of VEGF antagonist at 2-week

| Timepoint | VEGF antagonist expression (ng/device/day) | |
|---|---|---|
| | Single chamber device (1.3 mm diameter) | Cartridge (7 × 400 micron) |
| Pre-implant (day 7 in vitro) | 7810 ± 900 | 8883 ± 773 |
| Explant (2 week implant) | 2200 ± 621 | 4136 ± 573 |

Cell viability for the single chamber device following 2-weeks intraocular implant was 2.5 while the rating for the cartridge implant was 5.0. Representative histological examples of the 2-week explanted cells for the single chamber or multi-chamber cartridge implants are shown in FIGS. 5 and 6, respectively.

Example 2: Cell Efficiency as a Function of Decreasing Diffusion Distance

Individual chambers with varying internal diameters were cell encapsulated at the following volumes: 3, 4, 6 and 10 microliters. Devices were evaluated prior to implant at again following both 2 and 4 week implant periods in the rabbit vitreous. Expression of VEGF antagonist and histology was assessed for each group at the pre-implant and explant periods. Expression levels were compared and an efficiency of VEGF antagonist expression as a function of cell number was determined.

Figure 7:
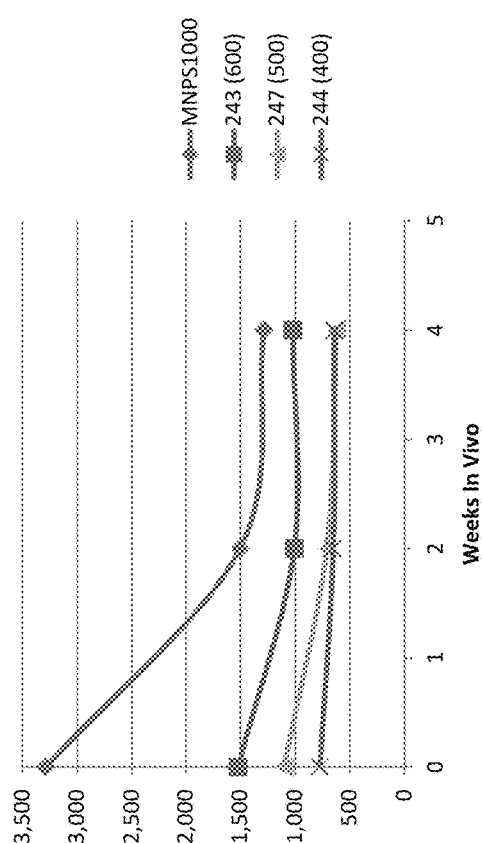
FIG. 7 is a graph showing the expression level of VEGF antagonist over time for each group with different device configuration, cell density and/or cell volume.
Figure 8:
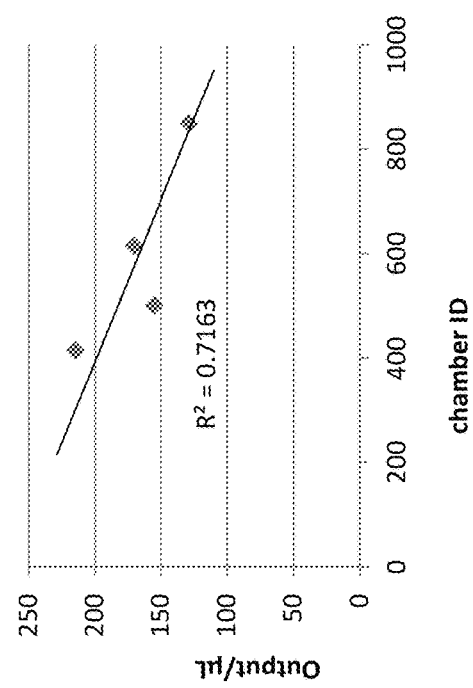
FIG. 8 is a graph showing an efficiency of VEGF antagonist expression as a function of chamber inner diameter.

FIG. 7 shows the expression level of VEGF antagonist over time for each group. It is apparent that the greatest change in expression occurs from the chamber device with the greatest internal diameter. As the diameters decrease the change in expression of VEGF antagonist decreases. An efficiency of VEGF antagonist expression as a function of chamber inner diameter is shown in FIG. 8.

Example 3: Cartridge Shelf-Life Stability

Figure 9:
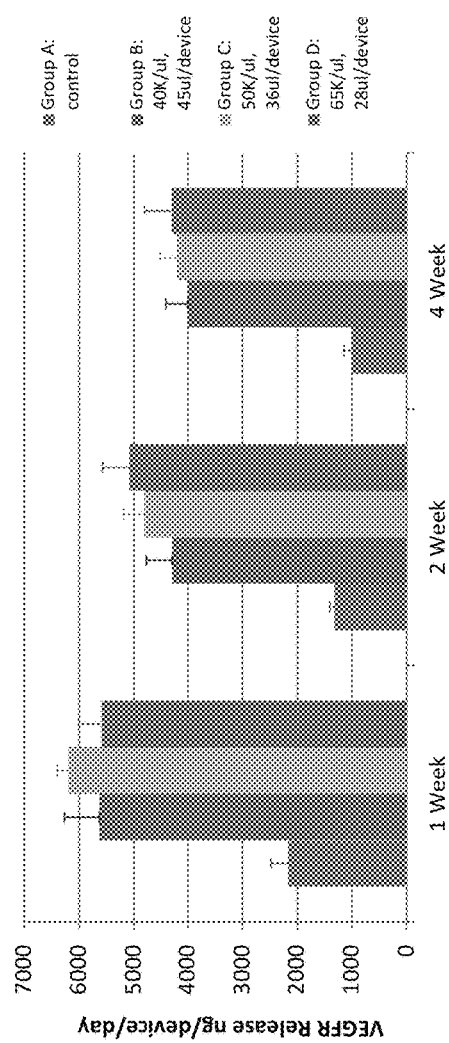
FIG. 9 is a bar graph showing VEGFR release from devices with different configurations.

Cartridge devices were manufactured with 5 individual chambers each having an internal diameter of 600 microns. Devices were encapsulated at various conditions of cell density and volume (B, C, D group as shown in FIG. 9) with ARPE-19 cell engineered to express VEGF antagonist and compared to a single chamber device (i.e., the control group in FIG. 9). Following encapsulation devices were placed in packages containing serum-free culture media and sealed. Device expression of VEGF antagonist was evaluated over time and the results are found in FIG. 7. Cartridge expression of VEGF antagonist was approximately 3-4 fold greater than the control group at all time points and irrespective of the individual loading conditions. Cartridge expression remained stable over the evaluation period.

Example 4: 5-Chamber Cartridge Device

NTC-203-910 cells were encapsulated in a 5-chamber cartridge device (Generation 3) at a cell density of 50,000 cells per microliter and maintained in 37 milliliters of culture media without exchange for 2 weeks. Expression of soluble VEGFR-receptor was evaluated in culture media at 2-weeks post encapsulation and then a cohort of devices were implanted bilaterally in the temporal inferior quadrant of New Zealand White rabbits and compared to implants of two single encapsulation devices (Generation 2) placed in the temporal and nasal inferior quadrant.

In this preliminary evaluation of a single cartridge geometry compared to two encapsulation implants, which had previously demonstrated functional and structural preservation of function in human wet AMD patients, all devices were explanted at 1-month to determine potential clinical efficacy.

Explant device VEGFR expression and histology as well as accumulated vitreous levels of VEGFR from both implant groups were evaluated. The results of device explants and vitreous levels are found in Table 2 below. Explanted devices were histologically sectioned by performing radial 4 micron cuts from the distal end of the device to the proximal end and the cells stained with eosin and hemotoxylin. Single devices implanted two per eye resulted in poor cell viability and distribution of cells particularly demonstrating cell death at the core of each device compared to cartridge devices, which resulted in a good distribution and viability of cells both at the periphery and core of each individual chamber of the cartridge. Presumably, the reduced diffusion distance and greater surface to volume ratio of each individual chamber compared to the single implant devices was a main contributor to improved cell viability.

TABLE 2

Implant VEGFR levels comparing Generation 3 5-Cartridge and double Generation 2 devices

| Implant Group | Explant VEGFR | Vitreous VEGFR |
|---|---|---|
| Generation 2 Double Implant | 1500 +/− 900 ng/24 hrs | 2800 +/− 300 ng/eye |
| Generation 3 Single Cartridge Implant | 2200 +/− 800 ng/24 hrs | 8100 +/− 930 ng/eye |

Example 5: Design Considerations and Performance of a Next-Generation Encapsulated Cell Technology (ECT) Intraocular Implant Delivering Soluble VEGF-Receptor Objective Early generation ECT products delivering soluble VEGF-receptor (VEGF-R) (e.g., single chambered ECT devices) for over 12 months have demonstrated clinically meaningful improvements in BCVA and reductions in macular thickening in patients with active neovascular AMD. Higher dose levels are expected to achieve efficacy comparable or greater than standard-of-care treatments.

Figure 10:
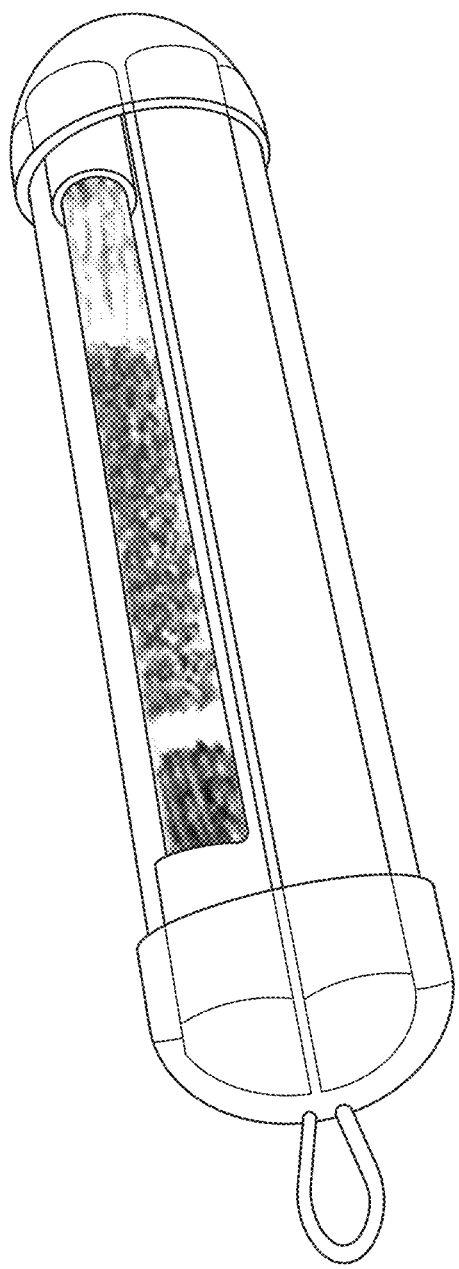
FIG. 10 is a schematic of the NT-503-3 (Generation 3) Multi-Chamber Implant.

A new ECT device, NT-503-3, incorporating multiple (e.g., more than 1) optimized cell encapsulation chambers into a single cartridge implant was designed to substantially increase VEGF-R by increasing the total number of encapsulated cells, and by improving cell viability and protein expression efficiency. This design also supports combination therapy from a single device by allowing discrete encapsulations of different therapeutic cell lines in a single intraocular implant product. A schematic of the NT-503-3 (Generation 3) Multi-Chamber Implant is shown in FIG. 10.

Methods and Materials

The performance of NT-503-3 was evaluated following encapsulation of a human RPE cell line transfected to produce VEGF-R. Dose levels of VEGF-R were characterized by ELISA. Binding efficiency and bioactivity were quantified by a VEGF-binding and HUVEC assay, respectively. GLP toxicology studies, which include clinical examination, ERG, IOP, ocular histopathology, clinical chemistry and detection of serum antibodies to VEGF-R and the encapsulated cell line are ongoing.

Results

A single NT-503-3 implant increased VEGF-R dose 5-fold compared to the previous ECT single implant (NT-503-2), which had demonstrated clinical efficacy in wet-AMD patients when implanted with two devices. VEGF-R produced by NT-503-3 results in high binding affinity to VEGF with a Kd of 0.7 pM and inhibits VEGF with an IC50 of 20-30 pM. Intraocular implants investigated in rabbits through 3-months of a 9-month GLP toxicology study demonstrate that the NT-503-3 product is safe and well tolerated.

Figure 11:
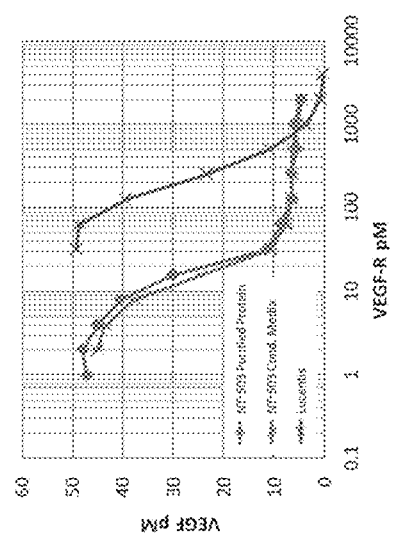
FIG. 11 shows VEGF binding of ECT produced VEGF-R.

In FIG. 11, VEGF binding of ECT produced VEGF-R was evaluated by the ability to neutralize recombinant human VEGF following co-incubation and detection of remaining free (unbound) VEGF using ELISA assay. Inhibitory activity of both purified VEGF-R protein and ECT device secreted VEGF-R (conditioned media, CM) indicate IC50=12 pM compared to Lucentis drug with IC50=250 pM. In a direct comparison to Lucentis, ECT secreted VEGF-R demonstrates a 20-fold increase in binding neutralization of human VEGF.

Figure 12:
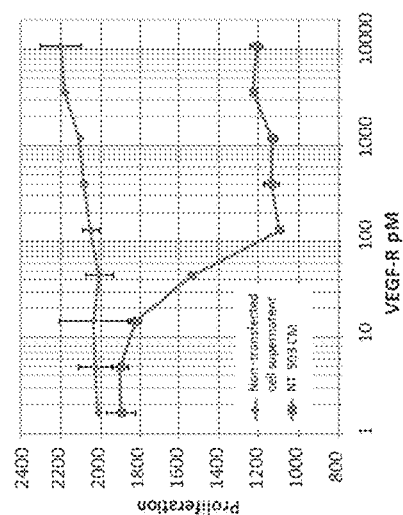
FIG. 12 shows measurement of the ability of the ECT produced VEGF-R to neutralize the bioactivity of rhVEGF on human umbilical vein endothelial cell proliferation. HUVEC cells.

FIG. 12 shows measurement of the ability of the ECT produced VEGF-R to neutralize the bioactivity of rhVEGF on human umbilical vein endothelial cell proliferation. HUVEC cells were incubated with various concentrations of ECT produced VEGF-R and compared to supernatant of non-transfected parental cells. The EC50 for the ECT produced VEGF R was approximately 40-50 pM with complete inhibition observed at 100 pM.

Figure 13A:
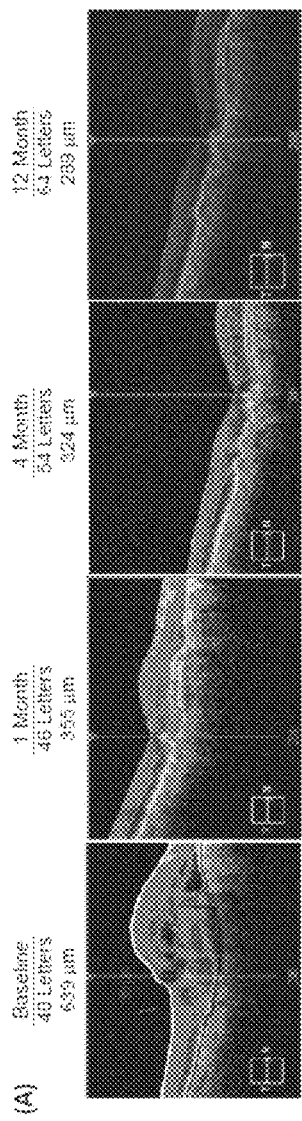
FIGS. 13A and 13B show the efficacy observed following intraocular delivery of VEGF-R over course of 12 months in human patients with wet-AMD. NT-503 is currently being studied in wet AMD patients receiving two early generation (NT-503-2) implant devices in one eye. Results observed thus far in the double-implant NT 503-2 study have been encouraging. The top panel (A) shows a study patient with marked reduction in intraretinal fluid and subretinal hyper-reflective material and improvement in visual acuity as early as one month. Improvements in OCT and VA thickness continue and remain at month 12. The bottom panel (B) graphically demonstrates robust reductions in central macular thickness occurring within the first month and persisting out to at least 12 months. As the study is on-going, the data presented in the figure are a "snap shot" of OCT response as not all patients have completed 12 months of follow-up.
Figure 13B:
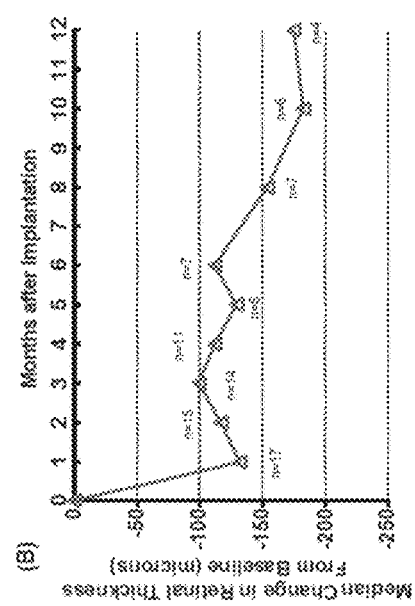
Figure 14A:
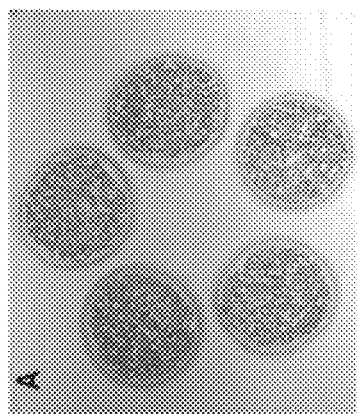
FIGS. 14A and 14B show representative histologic (H&E) section of encapsulated NT-503 cells arranged in 5-chamber cartridge format following 2-weeks incubation in culture media (A). VEGF-R concentration quantified in rabbit vitreous following 1-month intraocular implant comparing single NT-503-3 and double earlier Generation NT-503-2 (B).
Figure 14B:
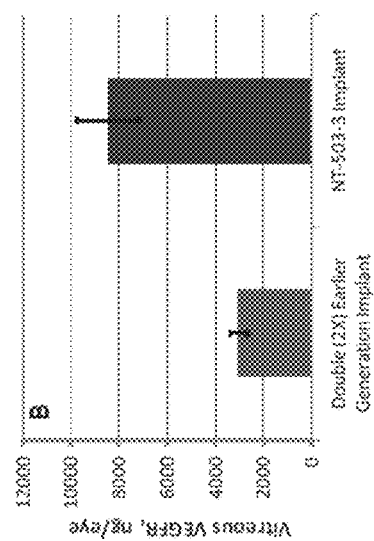

The efficacy observed following intraocular delivery of VEGF-R over the course of 12 months in human patients is shown in FIGS. 13A-B. A representative histologic section of encapsulated NT-503 cells arranged in a 5-chamber cartridge format is shown in FIGS. 14A-B.

Table 3 shows the ocular examination results following scheduled 6-month evaluation.

TABLE 3

| Toxicology Group | Aqueous Flare/Cell (0.5-4+) | Lens: Cataract | Lens Inflammatory Cells Posterior | Vitreous Haze (trace-4) | Vitreous Cell (trace-4+) |
|---|---|---|---|---|---|
| Naïve rabbits | 0/8 | 0/8 | 0/8 | 0/8 | 0/8 |
| NT-503-3 Implant | 0/6 | 0/6 | 0/6 | 0/6 | 1/6 (1+) |
| Empty NT-503-3 Implant | 0/6 | 0/6 | 0/6 | 0/6 | 0/6 |
| Injected NT-503-3 cells | 0/6 | 06 | 0/6 | 0/6 | 0/6 |

Compared to naïve controls, no changes in body weights, body temperature, IOP, ERG, hematology, clinical chemistry parameters, organ weight or macroscopic changes were attributable to NT-503-3 single implant with or without encapsulated cells or NT-503-3 cells directly injected into the eye. No increases in antibody titers to the cell line or to VEGF-R have been detected in any group.

Conclusions

Clinically relevant VEGF-R expression and a safe toxicology profile have been achieved with the NT-503-3 design. A single, intraocular NT-503-3 implant is expected to provide equivalent or improved efficacy compared to standard-of-care therapy while eliminating the burden of frequent injections in patients with active neovascular AMD. The multi-platform cartridge design also supports ongoing combination therapy development.

Devices and hold media (Endo-SFM) from three lots of NT-503-3 Investigational Cartridge Product were tested by USP <85> for endotoxin inhibition/enhancement to qualify the product for endotoxin testing by the Gel-Clot method. Three devices from each of 3 manufactured lots were divided in half and placed into 10-mL of endotoxin-free water (limulus amoebocyte lysate reagent water or LRW) for 1 hour at 37° C. prior to testing. The water sample from the device was tested undiluted. The hold media from each device was tested directly, undiluted.

Each device and hold media sample was tested "as is" and also spiked to an endotoxin concentration of approximately 0.03 EU/mL. Each sample was titered to endpoint along with the spiked water control. An endotoxin value between 0.016 and 0.063 EU/mL indicates no inhibition or enhancement of the assay by the sample.

When NT-503-3 Investigational Product and hold media were spiked with endotoxin control standard at the assay limit of detection, no enhancement or inhibition of the assay results were observed. The results from the devices are summarized below in Table 4 and the results for the corresponding device hold media (Endo-SFM) are found in Table 5.

TABLE 4

Endotoxin inhibition/enhancement qualification results for Cartridge device lots VD-031814, D07-14-014DEV, and D07-14-015DEV

| Lot | Device # | Sample "As Is" (No Endotoxin) | Sample + Endotoxin | Negative Control (Water only) | Positive Control (Water + Endotoxin) |
|---|---|---|---|---|---|
| VD-031814 | #1 | Negative | 0.016 EU/mL | Negative | 0.016 EU/mL |
| | #20 | Negative | 0.016 EU/mL | Negative | 0.016 EU/mL |
| | #34 | Negative | 0.016 EU/mL | Negative | 0.016 EU/mL |
| D07-14-014DEV | #8 | Negative | 0.016 EU/mL | Negative | 0.016 EU/mL |
| | #25 | Negative | 0.016 EU/mL | Negative | 0.016 EU/mL |
| | #40 | Negative | 0.016 EU/mL | Negative | 0.016 EU/mL |
| D07-14-015DEV | #3 | Negative | 0.016 EU/mL | Negative | 0.016 EU/mL |
| | #24 | Negative | 0.016 EU/mL | Negative | 0.016 EU/mL |
| | #42 | Negative | 0.016 EU/mL | Negative | 0.016 EU/mL |

TABLE 5

Endotoxin inhibition/enhancement qualification results for hold media (Endo-SFM) from Cartridge device lots VD-031814, D07-14-014DEV, and D07-14-015DEV

| Lot | Device # | Sample "As Is" (No Endotoxin) | Sample + Endotoxin | Negative Control (Water only) | Positive Control (Water + Endotoxin) |
|---|---|---|---|---|---|
| VD-031814 | #1 | Negative | 0.016 EU/mL | Negative | 0.016 EU/mL |
| | #20 | Negative | 0.016 EU/mL | Negative | 0.016 EU/mL |
| | #34 | Negative | 0.016 EU/mL | Negative | 0.016 EU/mL |
| D07-14-014DEV | #8 | Negative | 0.016 EU/mL | Negative | 0.016 EU/mL |
| | #25 | Negative | 0.016 EU/mL | Negative | 0.016 EU/mL |
| | #40 | Negative | 0.016 EU/mL | Negative | 0.016 EU/mL |

TABLE 5-continued

Endotoxin inhibition/enhancement qualification results for hold media (Endo-SFM) from Cartridge device lots VD-031814, D07-14-014DEV, and D07-14-015DEV

| Lot | Device # | Sample "As Is" (No Endotoxin) | Sample + Endotoxin | Negative Control (Water only) | Positive Control (Water + Endotoxin) |
|---|---|---|---|---|---|
| D07-14-015DEV | #3 | Negative | 0.016 EU/mL | Negative | 0.016 EU/mL |
| | #24 | Negative | 0.016 EU/mL | Negative | 0.016 EU/mL |
| | #42 | Negative | 0.016 EU/mL | Negative | 0.016 EU/mL |

Example 6: NT503 Analytical Results Including Establishment of Product Purity Specifications from Three Consecutive Manufacturing Lots Preliminary product purity was established for all detectable proteins continuously secreted and analyzed over a 24 hour period from NT-503 cartridge devices. Proteomic mass spectroscopy analysis was used to evaluate the protein profile of 20 device samples from 2 engineering and 3 consistency lots establishing repeatable detection of the most abundant proteins, quantifying NT-503 VEGFR plus 49 additional proteins. A direct mass purity index of cell produced proteins ratio to total proteins was established and a Pearson's moment correlation of all detected proteins based upon the relative percentage of each individual protein mass to total mass established a separate standard purity profile reference. A combination of analysis specifications including a mass purity index plus a total protein correlation provides a complementary product profile for purity evaluation. Product acceptance specifications require manufactured clinical lot samples to demonstrate both a purity index relating NT-503 produced protein to all pre-defined proteins detected >70% and a coefficient of determination, or $R^2$, greater than 0.70 correlations for all pre-defined 50 proteins in each tested sample compared to the reference standard. Acceptance criteria for both specifications for all samples from three subsequent manufacture lots of Generation 3 Cartridge devices meet or exceed the lower limit of specification for purity. Included in Table 1 are the results for ELISA VEGFR release as well as metabolic cell activity expressed absorbance of converted tetrazolium salt to a formazen dye (CCK-8 assay).

The majority of proteins other than the product NT-503 VEGFR are ubiquitous cytoskeleton, extracellular matrix or metabolic human proteins consistent with hRPE and hRPE-19 proteome MS profile.

Figure 15:
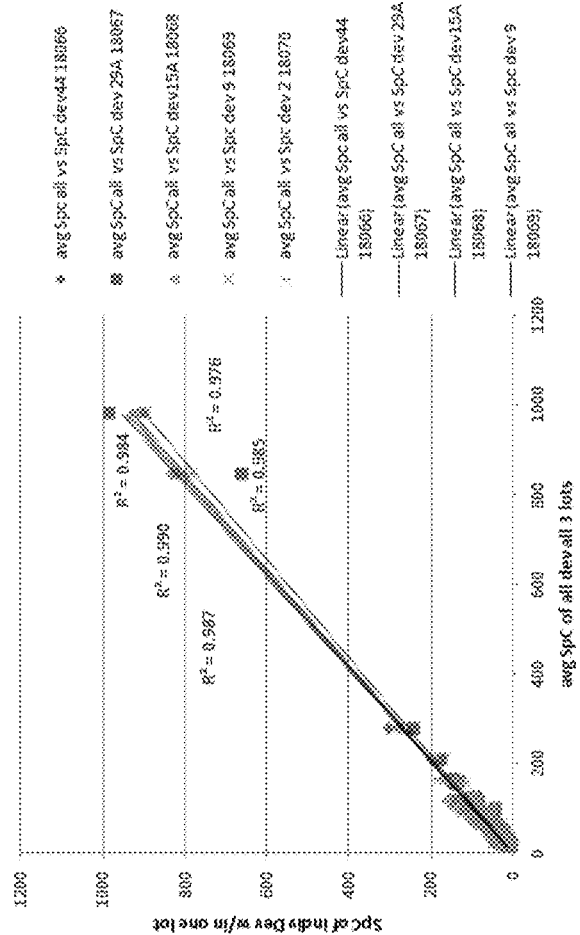
FIG. 15 shows protein profile secretion of ubiquitous proteins from multiple lots of Generation 3 cartridge devices. All lots demonstrate a correlation coefficient of greater than 90%. The purity index of therapeutic proteins was greater than 80% relative to non-therapeutic or excipient protein.

FIG. 15 shows protein profile secretion of ubiquitous proteins from multiple lots of Generation 3 cartridge devices. Table 6 shows analytical test results from three consecutive NT-503 cartridge device manufacturing lots.

TABLE 6

| | | | | Mass Spec Results | |
|---|---|---|---|---|---|
| Manufactured Lot | Device # | VEGFR Output, ng/day | CCK-8 | Mass Purity Index | Pearson Moment Correlation |
| D07-14-013DEV | 2 | 11,616 | 0.882 | 88.9 | 0.96 |
| | 9 | 10,046 | 0.930 | 88.6 | 0.96 |
| | 15 | 10,768 | 0.936 | 88.9 | 0.97 |
| | 29 | 11,217 | 0.984 | 87.3 | 0.95 |
| | 44 | 10,508 | 0.938 | 89.0 | 0.96 |
| | Average ± SD | 10,831 ± 315 | 0.934 ± 0.036 | 88.6 ± 0.7 | 0.96 ± 0.01 |
| D07-14-014DEV | 9 | 8,138 | 1.088 | 86.9 | 0.98 |
| | 18 | 7,588 | 1.129 | 81.8 | 0.97 |
| | 24 | 10,635 | 1.110 | 86.9 | 0.98 |
| | 32 | 9,631 | 1.054 | 84.4 | 0.99 |
| | 41 | 10,782 | 1.208 | 87.3 | 0.98 |
| | Average ± SD | 9,355 ± 508 | 1.118 ± 0.058 | 85.5 ± 2.4 | 0.98 ± 0.01 |
| D07-14-015DEV | 6 | 8,532 | 0.915 | 86.5 | 0.99 |
| | 14 | 11,026 | 1.042 | 90.0 | 0.95 |
| | 26 | 12,301 | 1.070 | 88.6 | 0.95 |
| | 39 | 11,.898 | 1.049 | 86.5 | 0.99 |
| | 44 | 11,749 | 1.183 | 89.9 | 0.95 |
| | Average ± SD | 11,1101 ± 281 | 1.052 ± 0.095 | 88.3 ± 1.7 | 0.97 ± 0.02 |

Example 7: Shelf Life and Shipping Qualification of NT-503-3 Implants Purpose

The purpose of this study was to verify performance of Generation 3 NT-503 (NT-503-3) devices following exposure to temperature ranges and durations representative of qualified shipping conditions. NT-503-3 devices contain VEGFR secreting cell line NTC-203-910 encapsulated in 5 individual hollow fiber chambers assembled as a cartridge, and held in primary packages containing Endo-SFM culture media.

In vitro performance was evaluated weekly over the course of 6 weeks for devices held at standard 37° C. incubation. Additionally, an extension of product shipment period from standard 1 week to 2 weeks was evaluated at temperature ranges between 16° C. and 37° C. representing potential clinical shipment using a qualified shipping system. Verification of shelf-life and shipment period stability was established for NT-503-3 devices following bi-lateral intraocular implants for 1 month in New Zealand white (NZW) rabbits.

Summary

NT-503-3 implants were manufactured under development protocol for the evaluation of device expression and cell viability over the course of a 6 week shelf life period (post manufacture). Three lots of implants were manufactured utilizing the NTC-203 cell line, VEGFR-910(834-10-5)-4-47, and sterile Generation 3 cartridge devices.

A critical component of the current study was the ability of NT-503-3 implants to "recover" when removed from the packaging and placed into fresh Endo-SFM. It is characteristic for the NT-503-3 packaging system (primary jar with Endo), that expression of VEGFR-910 reduces over time as the environment within the jar becomes metabolized. This reduction in 910 has proven to be transient though, whereby aged devices will demonstrate a robust recovery in expression once returned to a fresh media environment. The ability of all devices at all time points, and at all temperatures, to recover in their expression of 910 provides support that when implanted, the NT-503-3 product will perform as intended.

Surprisingly the decline in VEGFR expression over time was less acute than that recorded previously with single Generation 2 devices over a similar shelf-life period. The percentage loss of VEGFR for the Cartridge devices was 84% at 6 weeks relative to the initial VEGFR levels compared to a percentage loss of 97% for Generation 2. The slower decline in VEGFR is likely a function of the improvement in the design and the increased surface to volume ratio and decreased diffusion distance of cells to a nutrient source due to the thinner individual chambers of the cartridge compared to the single wider Generation 2 device.

In addition, the current study evaluated NT-503-3 devices in vivo to further confirm optimal performance even when implanted at the end of product shelf-life, or after exposure to the limits of shipping temperatures. Following 4 and 6 week holds in primary packaging, at all temperatures tested in the range of 16-37° C., NT-503-3 devices were implanted in New Zealand White (NZW) rabbits for 1 month. At the 1 month time point, all animals were examined by a veterinary ophthalmologist, and all devices and eyes were sampled for their concentrations of VEGFR-910.

For both the in vitro and in vivo arms of the current study, NT-503-3 implants demonstrated the ability to express optimal levels of 910 when packaged for up to 6 weeks. Furthermore, the data confirmed that shipment for up to 2 weeks, within a maintained temperature range of 16-37° C., is acceptable for NT-503-3 implants. Key results in support of those conclusions include:

- The 37° C. control arm of the current study met the NT-503-3 1 week release specification for VEGFR-910 expression.
- All NT-503-3 devices at all time points, and for all simulated shipping groups, demonstrated the ability to recover their expression of 910 once removed from packaging and returned to a fresh media environment. The down-regulation of 910 production is a known, transient phenomenon due to the gradual metabolization of packaging nutrients.
- The percentage of decline in VEGFR over a shelf-life period for the Generation 3 cartridge device was 84% compared to a more severe decline of 97% for the earlier Generation 2 single device design.
- NT-503-3 devices implanted after 4 and 6 weeks post-manufacture, whether held at 37° C. or in simulated shipping conditions, exhibited comparable levels of 910 in the vitreous and explant sampling confirming that no loss in functionality occurs over the course of the proposed NT-503-3 product shelf life.
- At all shelf-life and shipment conditions tested in the current study the subsequent 1-month device explant and vitreous levels of VEGFR protein as well as encapsulated cell viability were equivalent or exceeded the 1-month levels demonstrated in all previous NT-503 device evaluations.

Figure 16:
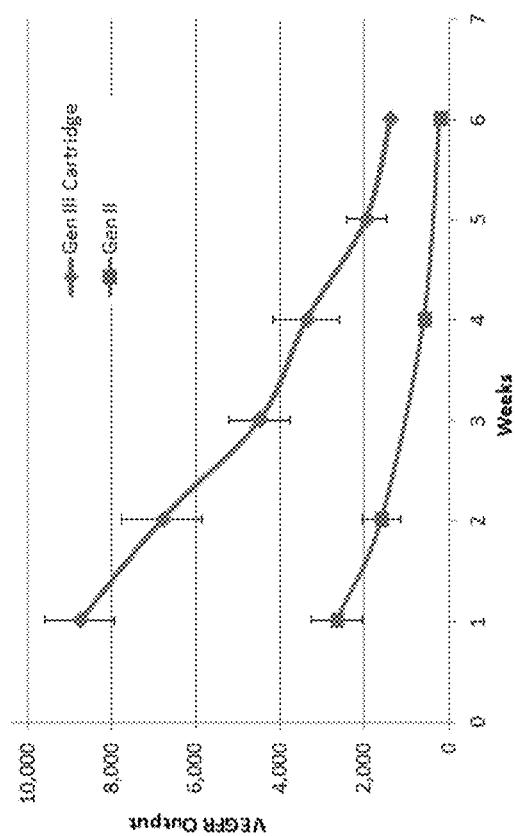
FIG. 16 shows the NT-503-3 shelf life comparison for Generation 2 and Generation 3 ECT devices.
Figure 17:
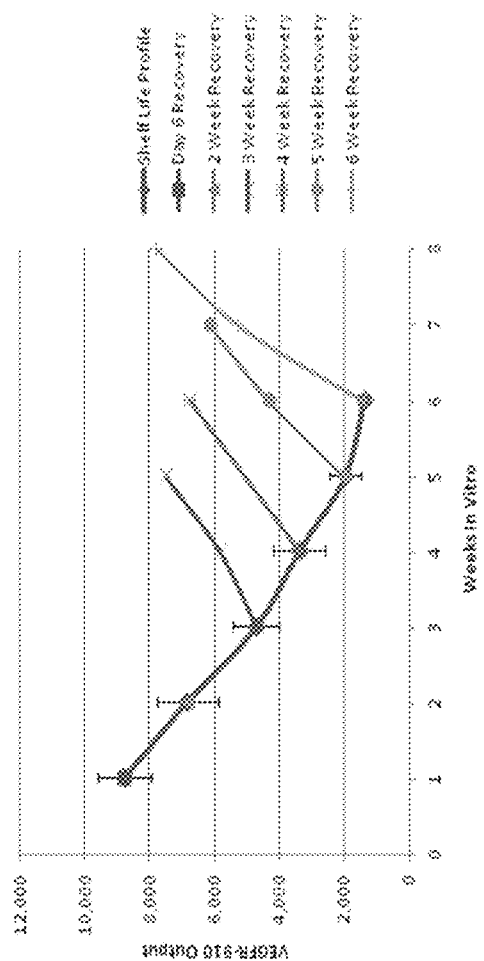
FIG. 17 shows NT-503-3 cartridge shelf life and recovery profiles.

The results of the Generation 2 and Generation 3 (i.e., NT-503-3) shelf life comparison are shown in FIG. 16. NT-503-3 cartridge shelf life and recovery profiles are shown in FIG. 17.

Figure 18:
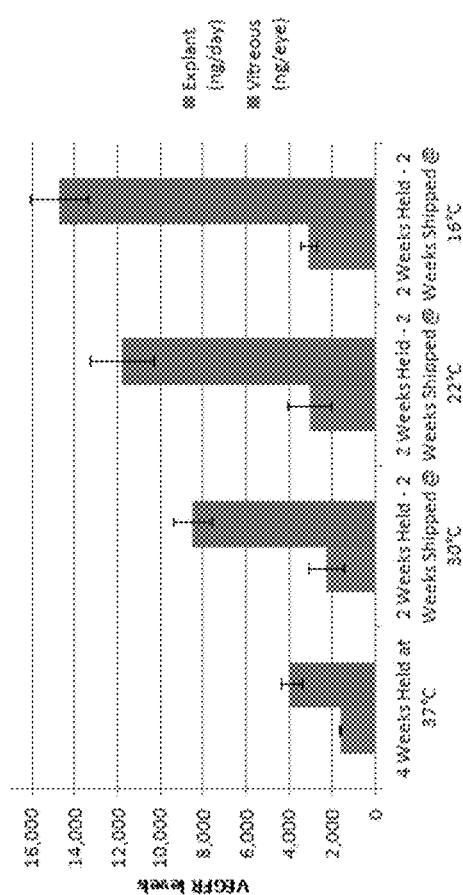
FIG. 18 shows NT-503-3 explant expression and corresponding vitreous concentrations following 4 week hold in packaging and 1 month implantation in rabbits.
Figure 19:
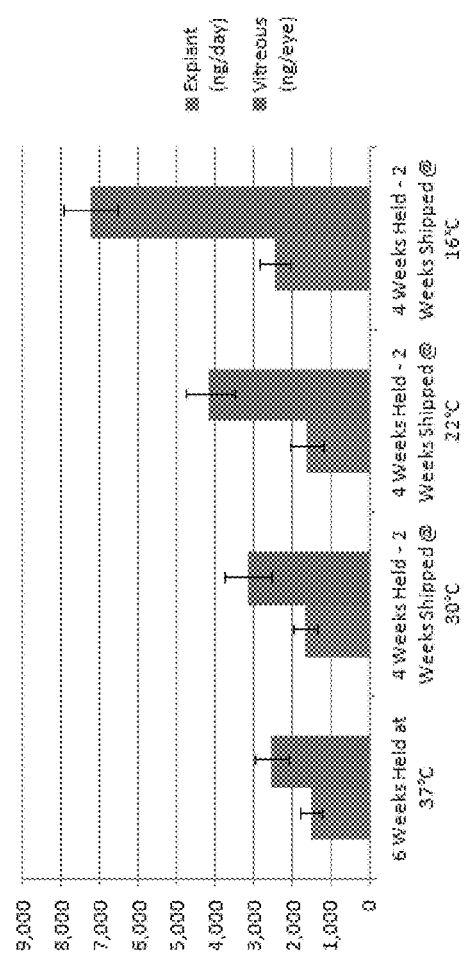
FIG. 19 shows NT-503-3 explant expression and corresponding vitreous concentrations following 6 week hold in packaging and 1 month implantation in rabbits.
Figure 20:
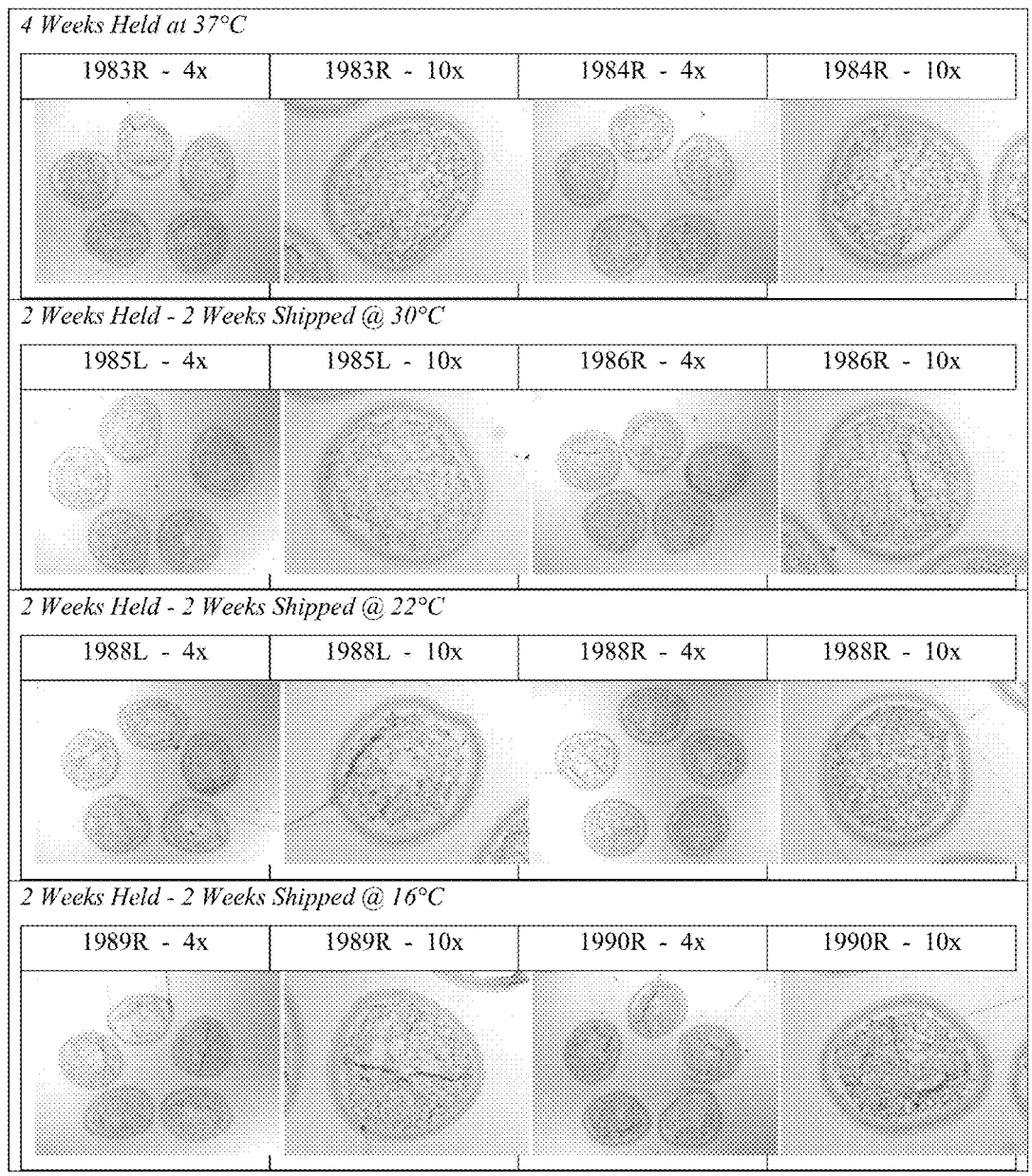
FIG. 20 shows in vivo encapsulated cell histology for 1 month explants

FIG. 18 shows NT-503-3 explant expression and corresponding vitreous concentrations following 4 week hold in packaging and 1 month implantation in rabbits, and FIG. 19 shows NT-503-3 explant expression and corresponding vitreous concentrations following 6 week hold in packaging and 1 month implantation in rabbits.

Example 8: Methods for Optimal Cell Filling of a Cartridge Device

Cell filling (encapsulation) of cartridges composed of 5 individual chambers and presumably any composition greater than 2 chambers requires a degassing and pre-wetting stage to ensure optimal distribution of cell mass within all chambers of the cartridge. Cell encapsulation without this step results in unacceptable variability of cell filling in all chambers and potentially no filling in some chambers.

Those skilled in the art will recognize that the sub-optimal cell-filling phenomenon may be explained by reference to the Laplace equation and bubble point method used to determine pore size of a membrane. The bubble point method utilizes the surface tension at the liquid-air interface of the membrane surface as means to prevent passage of air from the inside to outside of the membrane at a given pressure. Eventual penetration at increased pressure allows for pore size determination using the Laplace relationship.

The use of a system to equilibrate filling of all chambers of a cartridge is critical to develop and employ in the multi-chamber filling process for ECT cartridge devices.

FIG. 21 shows representative examples of cartridge devices without degassing/pre-wetting procedure.

The solution to ensure all chambers were be equally filled and distributed with encapsulated cells was to evacuate all air from the internal volume of the device and filling port and, importantly, completely fill all surfaces, particularly each chamber membrane surface and interconnecting pores with a wetting liquid. The present devices utilized an enclosed aseptic vacuum system that removes entrapped air in a pre-filled multi-chamber ECT device at a vacuum range of between 18 and 29.5 in Hg-gauge but preferably at 28.5 in Hg-gauge. Following vacuum degassing, the inner surfaces of the entire cartridge and filling system are completely filled with a liquid such as Hanks Balanced Salt Solution or other isotonic solution (saline, DMEM, etc.) for a defined period of vacuum immediately following termination of the degassing stage but just prior to development of subsequent liquid boiling.

Following degassing and liquid filling of the cartridge and cell-filling system, the cartridge device can be successfully loaded with cells per established encapsulation methods.

FIG. 22 shows representative examples of cartridge devices following implementation of a degassing/pre-wetting step.

Example 9: ECT Cartridge Devices Use to Evaluate a Combined PDGFR and VEGFR Product Separate cell lines expressing VEGFR (NTC-203-910) and those expressing PDGFR (NTC-206-999) were individually formulated at densities of 50,000 cells/microliter and encapsulated as individual cell lines in a Generation 3 cartridge device or encapsulated as a mixed suspension in a 50:50 ratio. Generation 3 devices with either VEFGFR secreting cells alone, PDGFR alone or as a combination were maintained in Endothelial SFM culture media in a closed package for 2 weeks. Levels of protein from each device group were evaluated at 2 weeks. VEGFR and PDGFR protein expression was within the expected range of between 10 and 18 micrograms per day.

Figure 23:
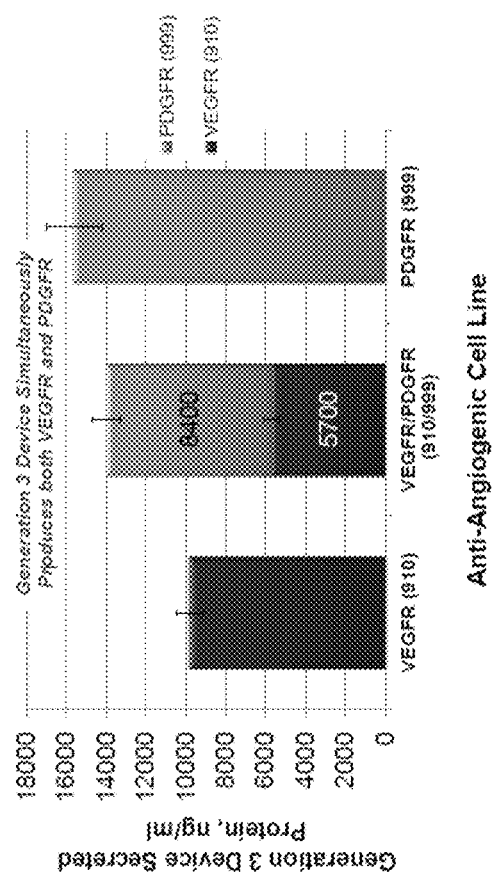
FIG. 23 shows Generation 3 cartridge device protein levels following encapsulation of PDGFR, VEGFR and their combination at 50:50 ratio.

Interestingly and unexpectedly the ratio of the combined VEGFR/PDGFR cell lines encapsulated in the Generation 3 cartridge device did not significantly vary and continued to maintain a 50:50 protein secretion ratio consistent with the initial cell loading ratio. (See FIG. 23).

EQUIVALENTS

The details of one or more embodiments of the invention are set forth in the accompanying description above. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

The foregoing description has been presented only for the purposes of illustration and is not intended to limit the invention to the precise form disclosed, but by the claims appended hereto.

We claim:

1. An implantable cell culture device comprising two or more individual chambers each having an inner diameter of between 100 μm and 900 μm, wherein each individual chamber comprises
   a) a core comprising between $1 \times 10^4$ and $7.5 \times 10^5$ genetically engineered ARPE-19 cells that produce a therapeutically effective amount of one or more biologically active molecules,
   b) a semi-permeable membrane surrounding the core that permits the diffusion of the biologically active molecules there through, and
   c) one or more access ports,
wherein the total diameter of the cell culture device is between 0.5 mm and 5.0 mm and the total internal volume of the cell culture device is between 2 μl and 100 μl.

2. The device of claim 1, wherein said one or more biologically active molecules are introduced into the ARPE-19 cells by an iterative transfection process, wherein the iterative transfection comprises one transfection, two transfections, or three transfections.

3. The device of claim 1, wherein said device is cryopreserved.

4. The device of claim 3, wherein the core comprises a cryoprotectant agent.

5. The device of claim 4, wherein the device is placed in a cryogenic storage vial, frozen under controlled rate freezing, and finally stored in vapor phase liquid nitrogen (−190° C.) conditions.

6. The device of claim 5, wherein the device is transported under vapor phase liquid nitrogen (−190° C.) conditions, under dry ice (−70° C.) conditions, or a combination thereof.

7. The device of claim 1, wherein the one or more biologically active molecules are selected from the group consisting of anti-angiogenic antibodies and molecules, anti-angiogenic antibody scaffolds, soluble receptors, agents targeting and inhibiting or modulating immunologic pathway molecules, growth factor inhibitors, cytokines, growth factors, neurotrophic factors, angiogenic factors, neurotransmitters, hormones, enzymes, anti-inflammatory factors, therapeutic proteins, gene transfer vectors, antibodies and antibody fragments, antigens, and any combination thereof.

8. The device of claim 1, wherein the one or more biologically active molecules are selected from the group consisting of C3a inhibitors, C3b inhibitors, other agents targeting and inhibiting or modulating immunologic pathway molecules, brain derived neurotrophic factor (BDNF), NT-4, ciliary neurotrophic factor (CNTF), Axokine, basic fibroblast growth factor (bFGF), insulin-like growth factor I (IGF I), insulin-like growth factor II (IGF II), acid fibroblast growth factor (aFGF), epidermal growth factor (EGF), transforming growth factor α (TGF α), transforming growth factor β (TGF β), nerve growth factor (NGF), platelet derived growth factor (PDGF), glia-derived neurotrophic factor (GDNF), Midkine, phorbol 12-myristate 13-acetate, tryophotin, activin, thyrotropin releasing hormone, interleukins, bone morphogenic protein, macrophage inflammatory proteins, heparin sulfate, amphiregulin, retinoic acid, tumor necrosis factor α, fibroblast growth factor receptor, epidermal growth factor receptor (EGFR), PEDF, LEDGF, NTN, Neublastin, neurotrophins, lymphokines, VEGF inhibitors, PDGF inhibitors, placental growth factor (PIGF) inhibitors, and other agents expected to have therapeutically useful effects on potential target tissues.

9. The device of claim 1, wherein said device comprises 2-20 chambers.

10. The device of claim 1, wherein the nominal ratio of inner diameter to wall thickness of each chamber is about 5:1 to 20:1 in scale.

11. The device of claim 1, wherein the length of the device is between 0.4 mm and 11 mm.

12. The device of claim 1, wherein the core of each chamber further comprises a matrix disposed within the semi-permeable membrane.

13. The device of claim 12, wherein the matrix comprises a plurality of monofilaments, wherein said monofilaments are
a) twisted into a yarn or woven into a mesh, or
b) twisted into a yarn that is in non-woven stands, and wherein the cells are distributed thereon.

14. The device of claim 13, wherein the monofilaments comprise a biocompatible material selected from the group consisting of acrylic, polyester, polyethylene, polypropylene polyacetonitrile, polyethylene terephthalate, nylon, polyamides, polyurethanes, polybutester, silk, cotton, chitin, carbon, and biocompatible metals.

15. The device of claim 13, wherein the monofilaments comprise polyethylene terephthalate (PET) fibers that comprise between 1-85% of the internal volume of each chamber of the device.

16. The device of claim 1, wherein the device further comprises a tether anchor.

17. The device of claim 16, wherein the tether anchor comprises an anchor loop.

18. The device of claim 17, wherein the anchor loop is adapted for anchoring the device to an ocular structure.

19. The device of claim 1, wherein the device is implanted into the eye or another target region selected from the group consisting of spleen, ear, heart, colon, liver, kidney, breast, joint, bone marrow, subcutaneous, and peritoneal spaces.

20. The device of claim 19, wherein the device is implanted in the vitreous, the aqueous humor, the Subtenon's space, the periocular space, the posterior chamber, or the anterior chamber of the eye.

21. The device of claim 1, wherein the semi-permeable membrane comprises a permselective, immunoprotective membrane.

22. The device of claim 1, wherein the semi-permeable membrane comprises an ultrafiltration membrane or a microfiltration membrane.

23. The device of claim 21 or 22, wherein the semi-permeable membrane has a median pore size of 1-500 nm.

24. The device of claim 1, wherein the semi-permeable membrane is formed into a porous structure.

25. The device of claim 1, wherein the semi-permeable membrane is made from biocompatible material selected from the group consisting of polyacrylates, polyvinylidenes, polyvinyl chloride copolymers, polyurethanes, polystyrenes, polyamides, cellulose acetates, cellulose nitrates, polysulfones, polyether sulfones, polyphosphazenes, polyacrylonitriles, poly(acrylonitrile/covinyl chloride), and derivatives, copolymers and mixtures thereof.

26. The device of claim 1, wherein the nominal molecular weight cut off (MWCO) of the semi-permeable membrane is between 10 and 1000 kD.

27. The device of claim 1, wherein the semi-permeable membrane wall thickness is between 10 μm and 200 μm thick.

28. The device of claim 1, wherein the ends of the device are sealed using methyl methacrylate or another medical-grade, biocompatible material formulated or manufactured to form a hermetic seal integrating all components of the device at each end of the device.

29. Use of the device of claim 1 to deliver an appropriate therapeutic dose of the one or more biologically active molecules to a target region of a subject, wherein the therapeutic dose is at least 0.1 pg/day.

30. A method for treating a disorder, comprising
a) implanting the implantable cell culture device of claim 7 into a target region of a patient, and
b) allowing the one or more soluble receptors or anti-angiogenic antibodies and molecules to diffuse from the device and bind to VEGF, PDGF, or both VEGF and PDGF in the target region, thereby treating the disorder.

31. A method for treating a disorder, comprising
a) implanting the implantable cell culture device of claim 1 into a target region of a patient, and
b) allowing the one or more biologically active molecules to diffuse from the device, thereby treating the disorder.

32. The method of claim 30 or claim 31, wherein the disorder is selected from the group consisting of ophthalmic disorders, endothelial cell proliferation or vascularization related disorders, cancer, infectious disorders, inflammatory disorders, immunologic disorders, digestive disorders, vascular disorders, lung disorders, oral disorders, blood disorders, liver disorders, skin disorders, prostate disorders, kidney disorders, metabolic disorders, endocrine disorders, neurologic disorders, and neurodegenerative disorders.

33. The method of claim 32, wherein the ophthalmic disorder is selected from the group consisting of branch or central retinal vein occlusion (BRVO or CRVO), uveitis, macular telangiectasia, retinopathy of prematurity, diabetic macular edema, diabetic retinopathy, age-related macular degeneration, glaucoma, retinitis pigmentosa, cataract formation, retinoblastoma and retinal ischemia.

34. The method of claim 33, wherein age-related macular degeneration is the wet form age-related macular degeneration (AMD) or atrophic AMD.

35. The method of claim 32, wherein the ophthalmic disorder is BRVO or CRVO.

36. The method of claim 32, wherein the endothelial cell proliferation or vascularization related disorders are selected from the group consisting of hematologic disorders, atherosclerosis, inflammation, increased vascular permeability and malignancy.

37. The method of claim 30, wherein between 0.1 pg and 10000 μg per patient per day of the soluble receptors or anti-angiogenic antibodies and molecules diffuse into the target region, wherein the soluble receptor is a soluble VEGF receptor or a soluble PDGF receptor.

38. The method of claim 31, wherein between 0.1 pg and 10000 μg per patient per day of the biologically active molecules diffuses into the target region.

39. A method of delivering biologically active molecules to a recipient host, comprising implanting the implantable cell culture device of claim 1 into a target region of the recipient host, wherein the one or more encapsulated ARPE-19 cells secrete the biologically active molecules at the target region.

40. The method of claim 30, 31 or 39, wherein the target region is selected from the group consisting of the aqueous and vitreous humors of the eye, spleen, ear, heart, colon, liver, kidney, breast, joint, bone marrow, subcutaneous, and peritoneal spaces.

41. The method of claim 39, wherein a therapeutically effective amount per patient per day of the biologically active molecules diffuses into the target region.

42. A method of making the implantable cell culture device of claim 1, comprising
   a) genetically engineering at least one ARPE-19 cell to secrete one or more biologically active molecules;
   b) producing an individual chamber; and
   c) assembling two or more individual chambers to form said device.

43. The method of claim 42, further comprising encapsulating said genetically modified ARPE-19 cells within a semi-permeable membrane of the individual chamber, wherein said membrane allows the diffusion of the one or more biologically active molecules there through.

44. The method of claim 43, wherein said two or more individual chambers each comprises genetically engineered ARPE-19 cells that secrete the same one or more biologically active molecules or each comprises genetically engineered ARPE-19 cells that secrete different one or more biologically active molecules.

45. The method of claim 42, wherein the one or more biologically active molecules are selected from the group consisting of anti-angiogenic antibodies and molecules, anti-angiogenic antibody scaffolds, soluble receptors, agents targeting and inhibiting or modulating immunologic pathway molecules, immunologic factors or targets, growth factor inhibitors, cytokines, growth factors, neurotrophic factors, angiogenic factors, neurotransmitters, hormones, enzymes, anti-inflammatory factors, therapeutic proteins, gene transfer vectors, and any combination thereof.

46. The method of claim 45, wherein the one or more biologically active molecules are selected from the group consisting of C3a inhibitors, C3b inhibitors, other agents targeting and inhibiting or modulating immunologic pathway molecules, brain derived neurotrophic factor (BDNF), NT-4, ciliary neurotrophic factor (CNTF), Axokine, basic fibroblast growth factor (bFGF), insulin-like growth factor I (IGF I), insulin-like growth factor II (IGF II), acid fibroblast growth factor (aFGF), epidermal growth factor (EGF), transforming growth factor α (TGF α), transforming growth factor β (TGF β), nerve growth factor (NGF), platelet derived growth factor (PDGF), glia-derived neurotrophic factor (GDNF), Midkine, phorbol 12-myristate 13-acetate, tryophotin, activin, thyrotropin releasing hormone, interleukins, bone morphogenic protein, macrophage inflammatory proteins, heparin sulfate, amphiregulin, retinoic acid, tumor necrosis factor α, fibroblast growth factor receptor, epidermal growth factor receptor (EGFR), PEDF, LEDGF, NTN, Neublastin, neurotrophins, lymphokines, VEGF inhibitors, PDGF inhibitors, PlGF inhibitors, Tie2, CD55, C59, a bispecific molecule that simultaneously binds VEGF and PDGF, and other agents expected to have therapeutically useful effects on potential target tissues.

47. The method of claim 42, the two or more individual chambers are formed prior to the addition of the genetically engineered at least one ARPE-19 cell.

48. The method of claim 47, wherein the method comprises a degassing/prewetting step prior to the addition of the genetically engineered at least one ARPE-19 cell.

* * * * *